(12) United States Patent
Marchand et al.

(10) Patent No.: US 11,001,846 B2
(45) Date of Patent: May 11, 2021

(54) APTAMERS, NUCLEIC ACID MOLECULES, POLYNUCLEOTIDES, SYNTHETIC ANTIBODIES COMPOSITIONS FOR DETECTING PRRS VIRUSES AND TREATING PRRS VIRUS INFECTION

(71) Applicant: AEROVIRUS TECHNOLOGIES INC., Québec (CA)

(72) Inventors: Norman Marchand, Québec (CA); Thomas Caltagirone, Jacobus, PA (US); Albert Liao, Jacobus, PA (US)

(73) Assignee: AEROVIRUS TECHNOLOGIES INC., Quebec (CA)

( * ) Notice: Subject to any disclaimer, the term of this patent is extended or adjusted under 35 U.S.C. 154(b) by 322 days.

(21) Appl. No.: 16/060,001

(22) PCT Filed: Dec. 1, 2016

(86) PCT No.: PCT/CA2016/051411
§ 371 (c)(1),
(2) Date: Jun. 6, 2018

(87) PCT Pub. No.: WO2017/096468
PCT Pub. Date: Jun. 15, 2017

(65) Prior Publication Data
US 2018/0371461 A1    Dec. 27, 2018

(30) Foreign Application Priority Data

Dec. 10, 2015 (CA) ..................... 2914337

(51) Int. Cl.
| | |
|---|---|
| *C12N 15/11* | (2006.01) |
| *C12N 15/115* | (2010.01) |
| *A61K 31/711* | (2006.01) |
| *C12Q 1/70* | (2006.01) |
| *C07K 16/10* | (2006.01) |
| *G01N 33/53* | (2006.01) |
| *C12Q 1/68* | (2018.01) |
| *A61K 31/7088* | (2006.01) |
| *A61P 31/14* | (2006.01) |

(52) U.S. Cl.
CPC ........ *C12N 15/115* (2013.01); *A61K 31/7088* (2013.01); *A61K 31/711* (2013.01); *A61P 31/14* (2018.01); *C07K 16/10* (2013.01); *C12Q 1/68* (2013.01); *C12Q 1/70* (2013.01); *G01N 33/5308* (2013.01); *C12N 2310/16* (2013.01); *G01N 2333/08* (2013.01)

(58) Field of Classification Search
CPC ... C12N 15/115; C12N 2310/16; A61P 31/14; C12Q 1/70; G01N 2333/08
See application file for complete search history.

(56) References Cited

FOREIGN PATENT DOCUMENTS

| KR | 20130032128 A | 4/2013 |
| KR | 20160086478 A | 7/2016 |
| WO | WO2002060924 A2 | 8/2002 |

OTHER PUBLICATIONS

International Search Report and Written Opinion dated Mar. 8, 2017.
Lee S. J. et al "Detection of VR-2332 strain of porcine reproductive and respiratory syndrome virus type II using an aptamer-based sandwich-type assay." Anal Chem. Jan. 2, 2013;85(1):66-74. doi: 10.1021/ac3026866. Epub Dec. 11, 2012.

*Primary Examiner* — Ekaterina Poliakova-Georgantas
(74) *Attorney, Agent, or Firm* — Fresh IP PLC; Clifford D. Hyra; Aubrey Y Chen

(57) ABSTRACT

Aptamers, polynucleotides which participate in preventing the Porcine Respiratory and Reproductive Syndrome virus (PRRSV) infection of cells, and nucleic acid molecules, which include a polynucleotide sequence capable of specifically binding the polypeptides domain of the PRRSV that controls infection, constitute the core of the present invention. Also provided are methods of using such nucleic acid molecules, polynucleotides and synthetic antibodies directed against these, for detection, treating and neutralization of PRRSV infection.

12 Claims, 45 Drawing Sheets

Specification includes a Sequence Listing.

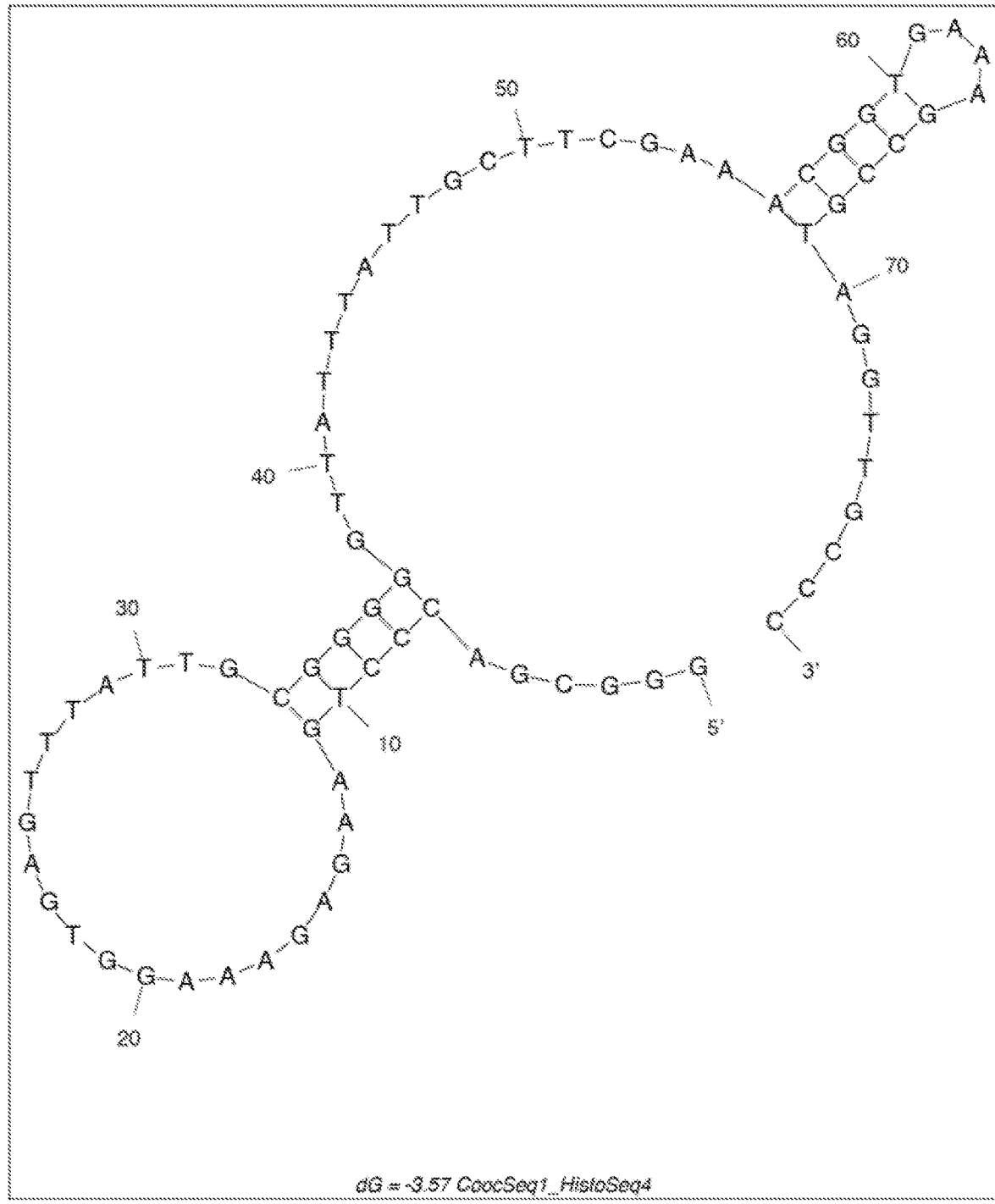
Figure 5a A501

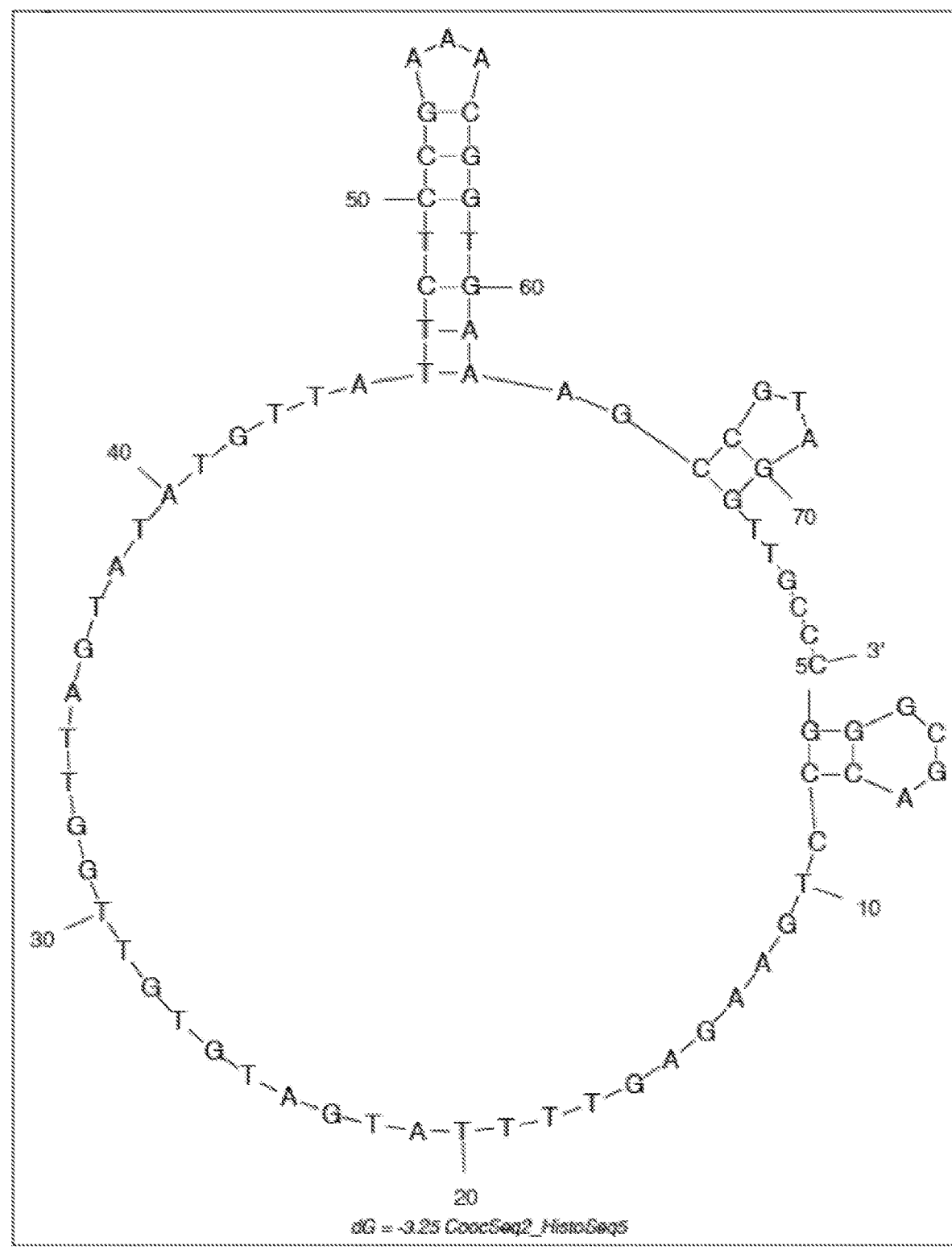
Figure 5b A502

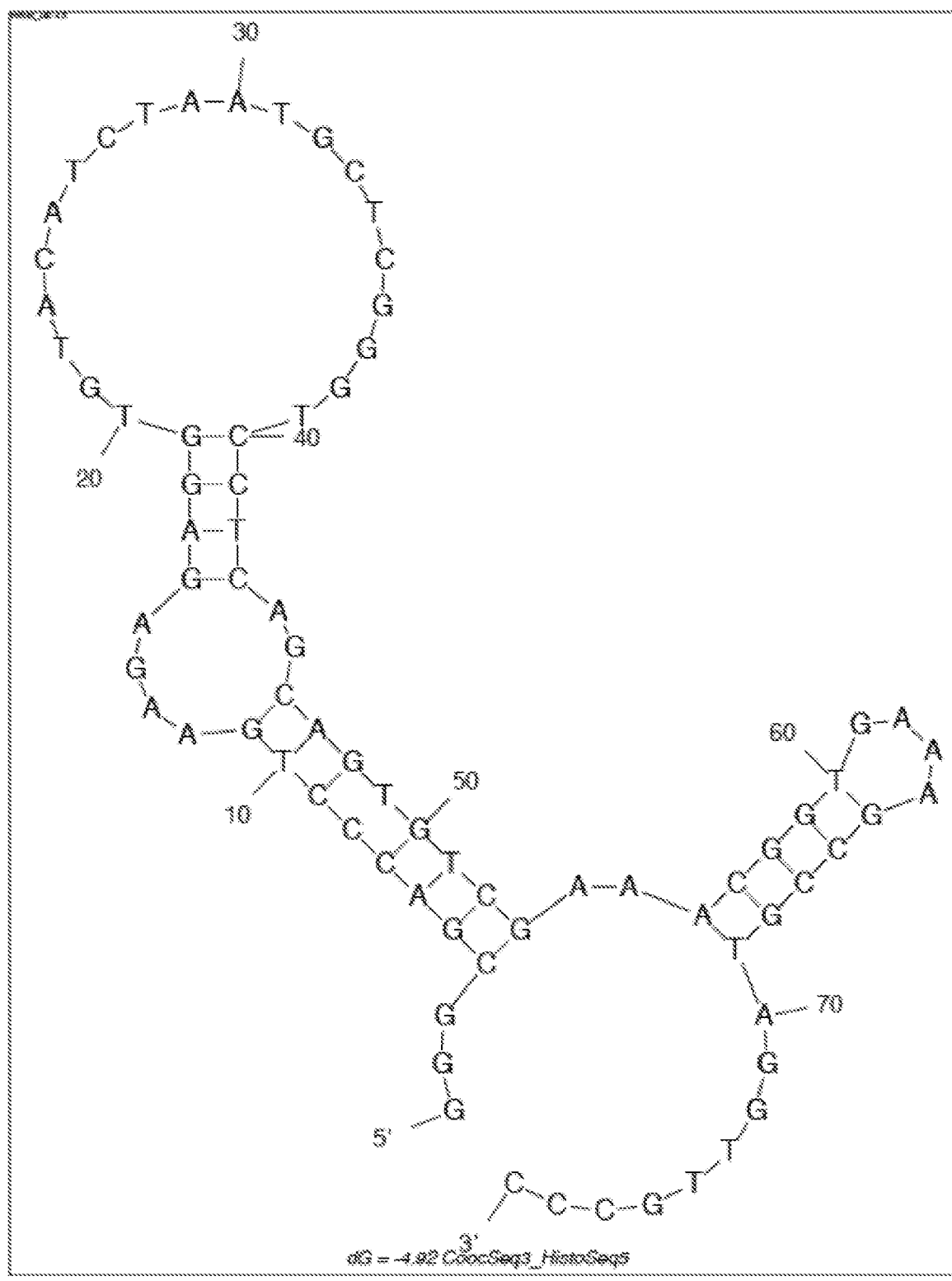
Figure 5c A503

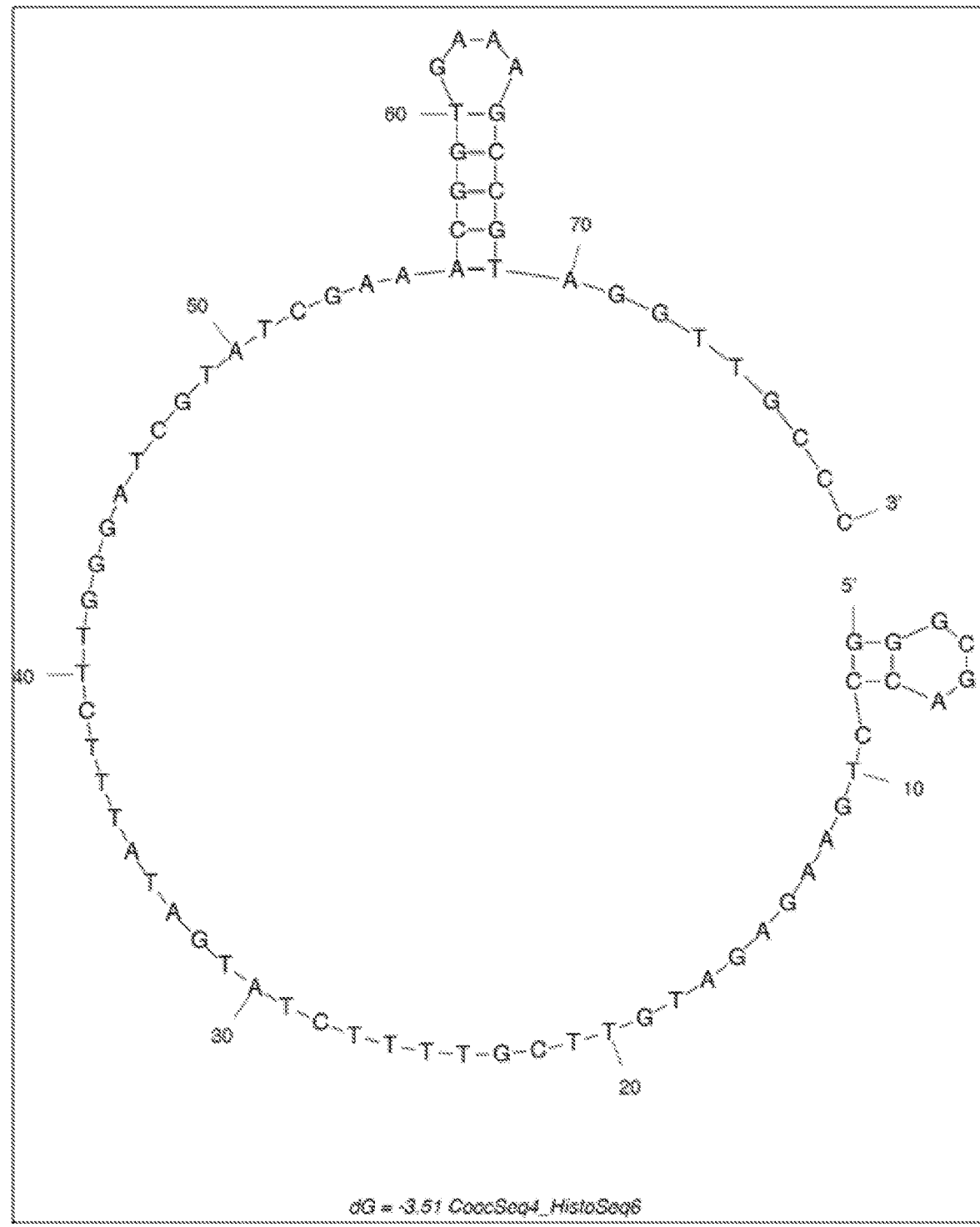
Figure 5d A504

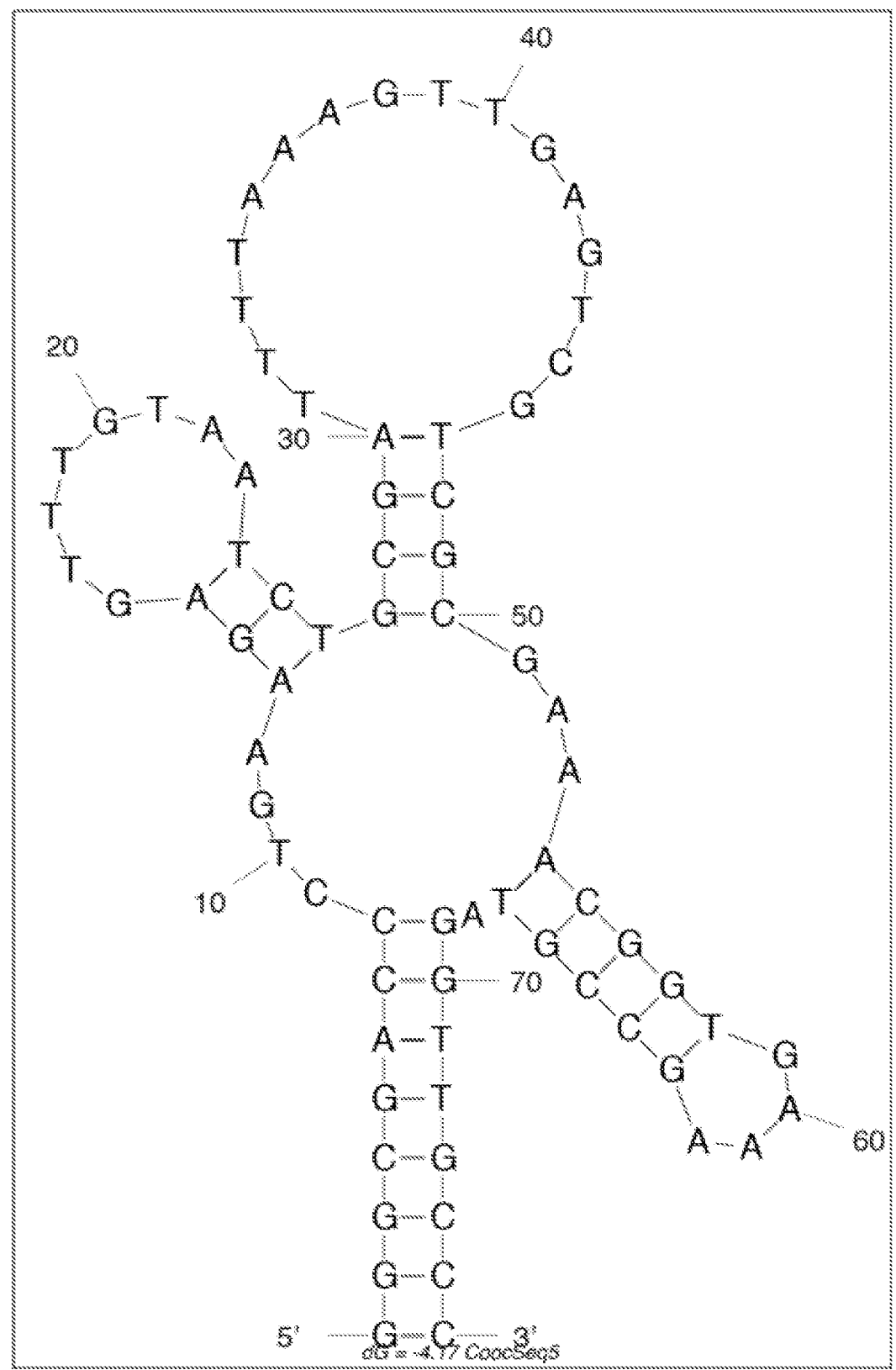
Figure 5e A505

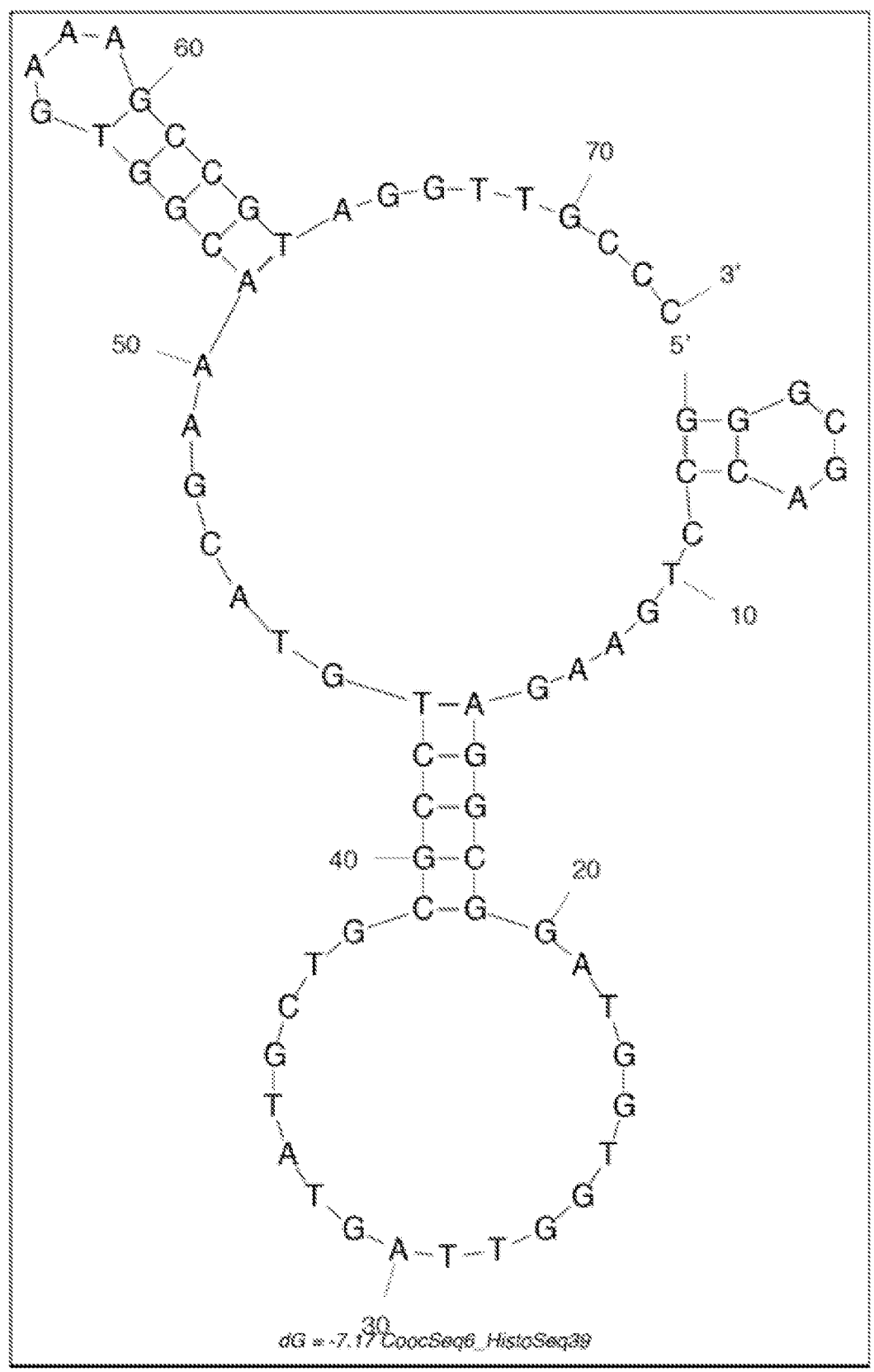
Figure 5f A506

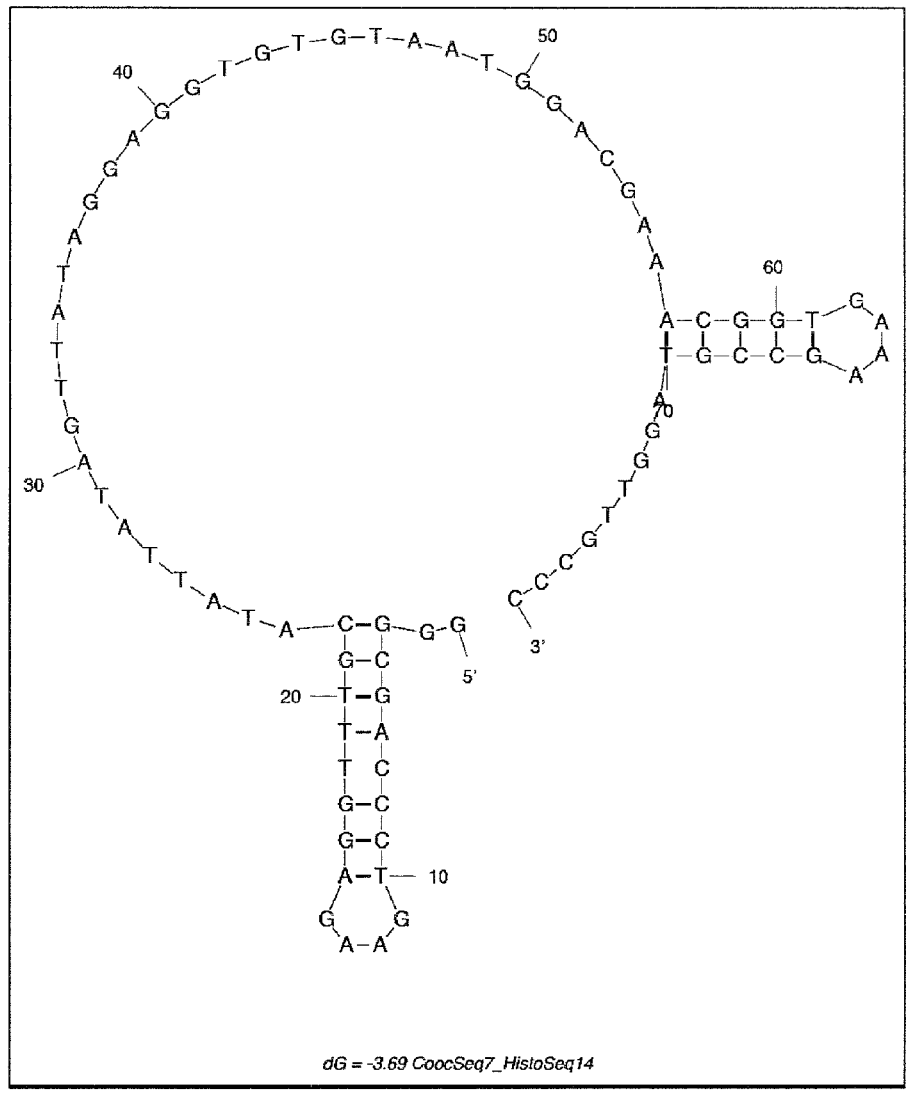
Figure 5g A507

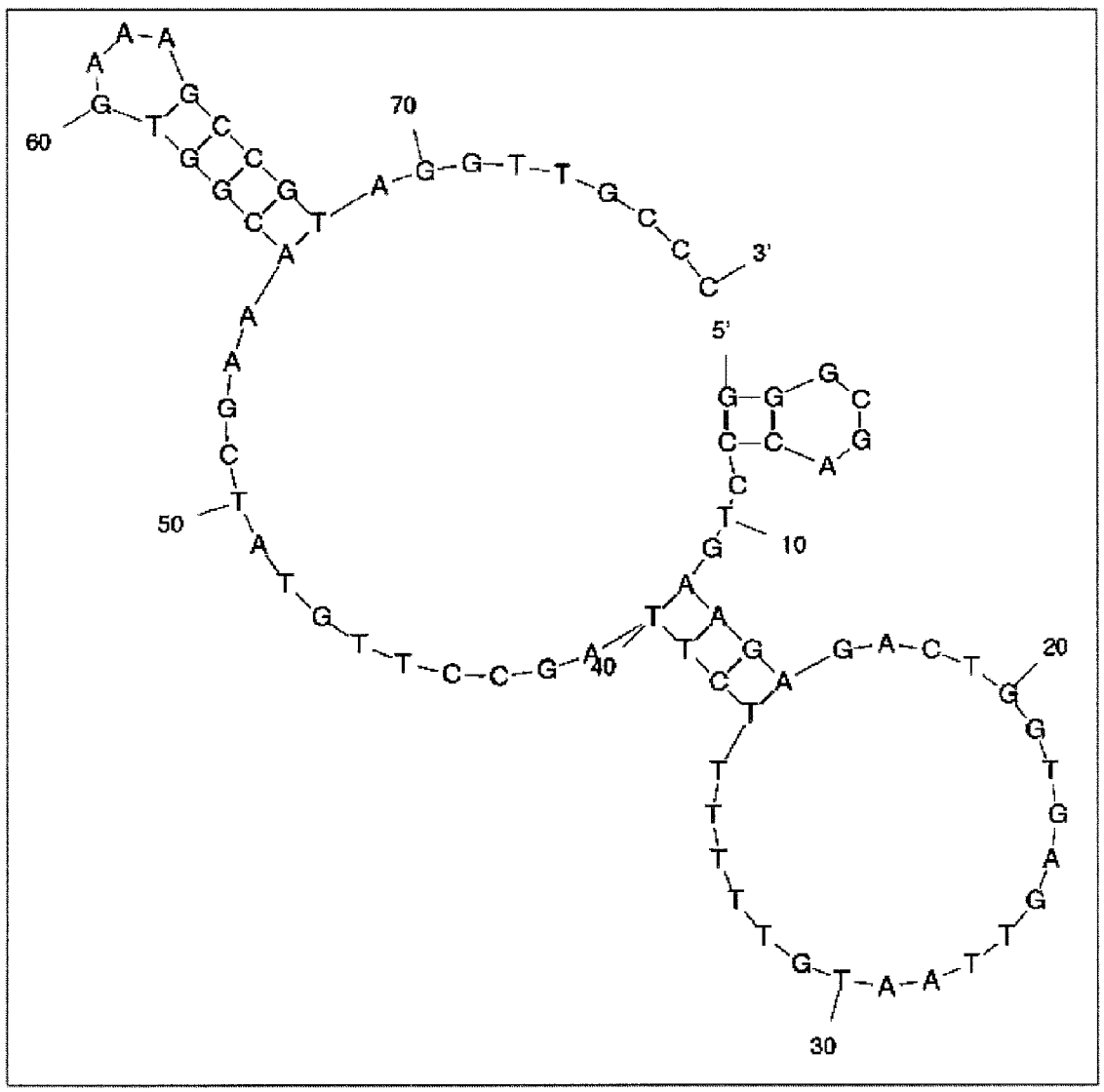
Figure 5h A508

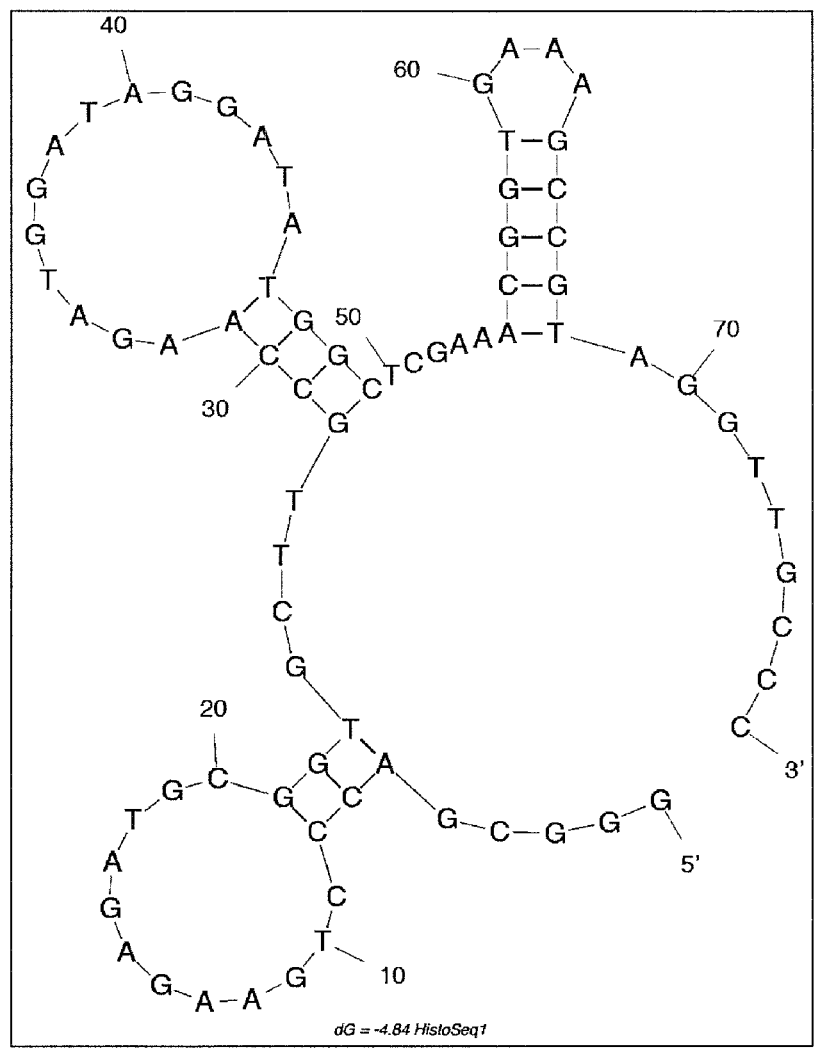
Figure 5i A509

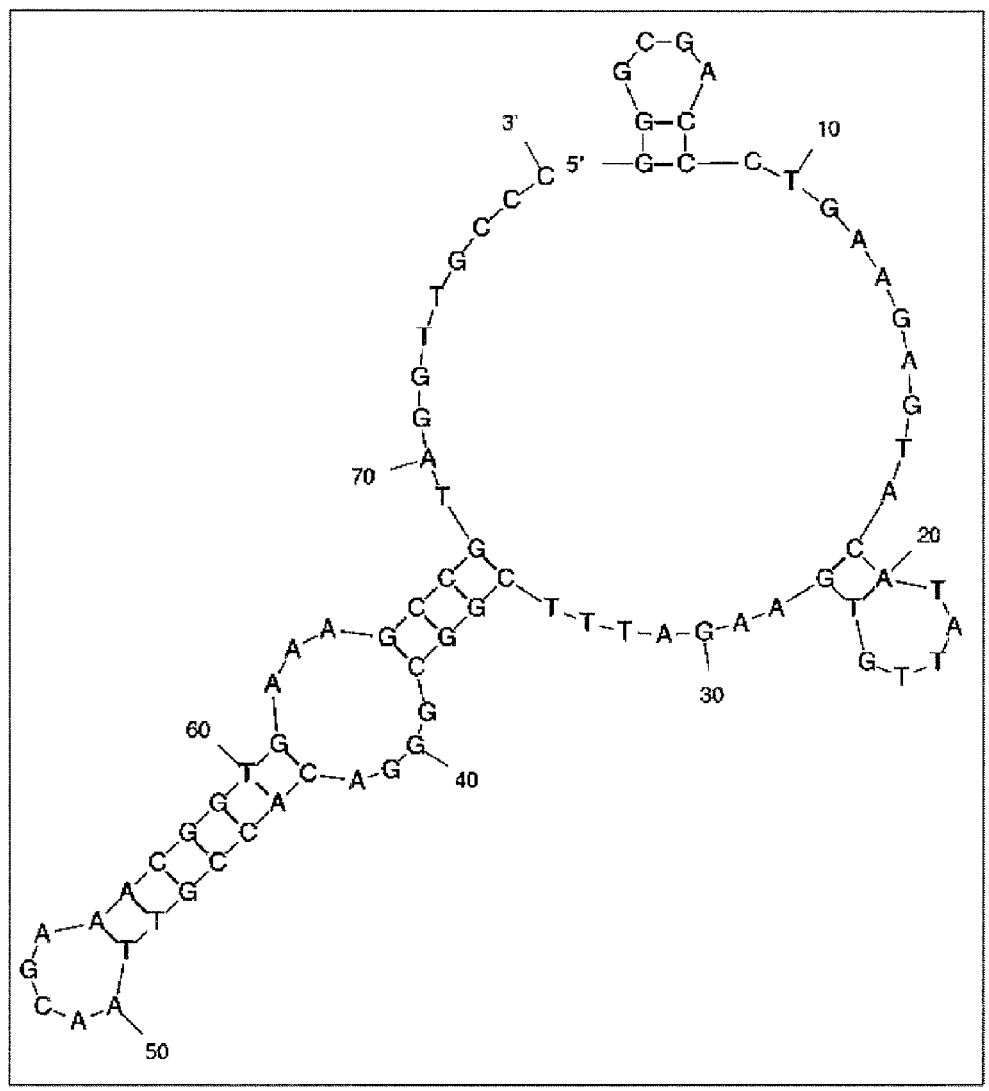
Figure 5j A510

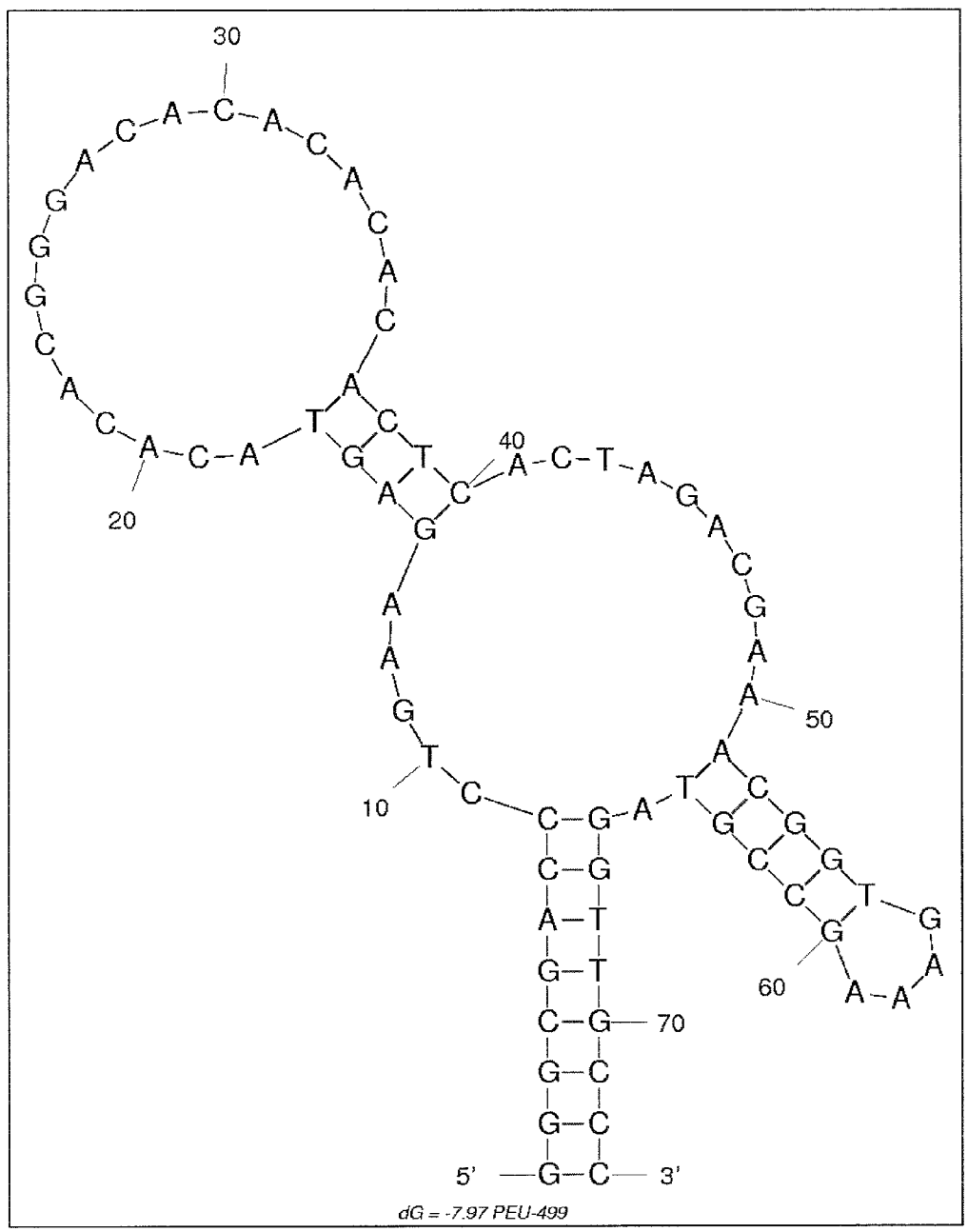
Figure 6a PEU-499

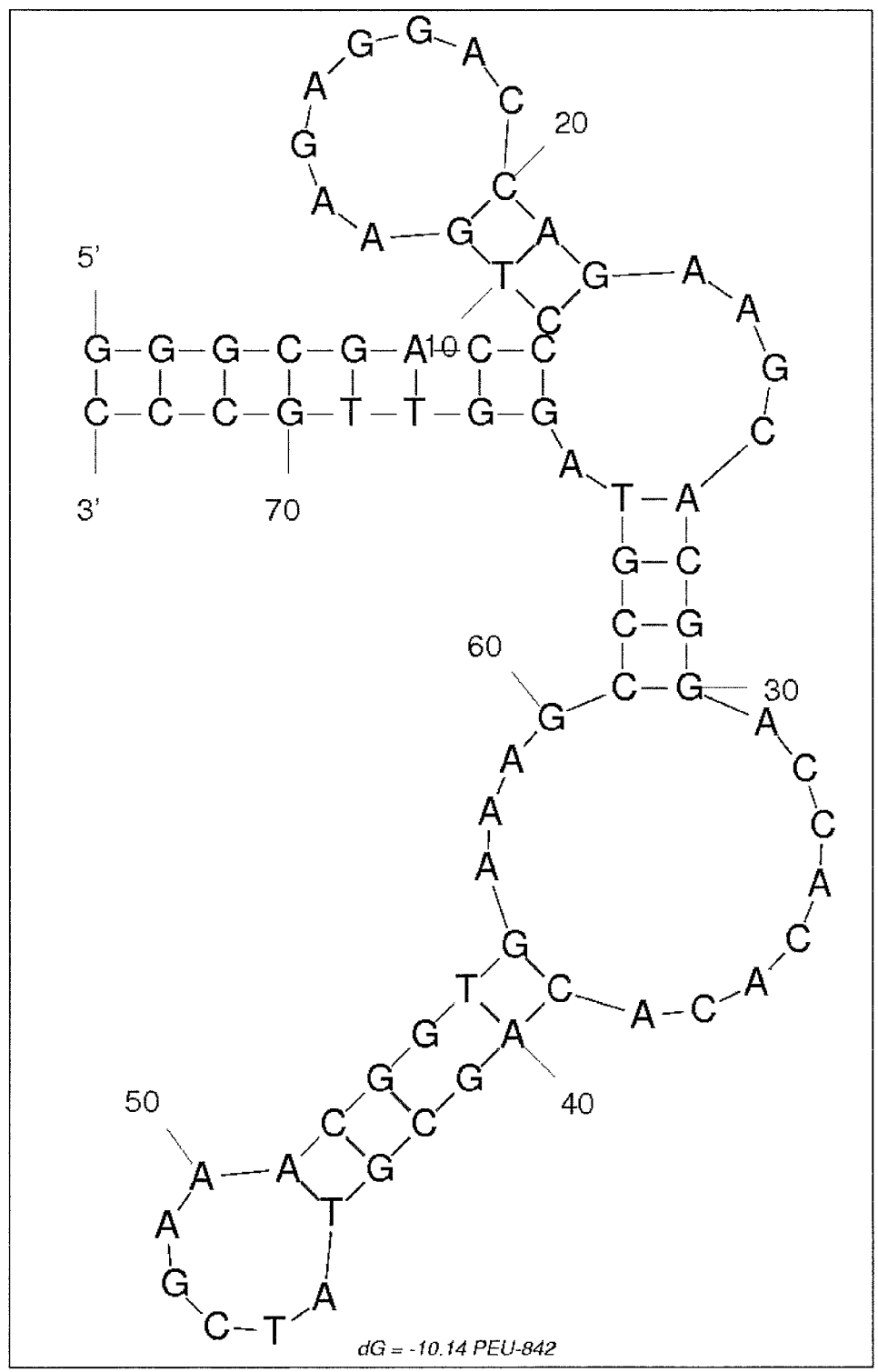
Figure 6b PEU-842

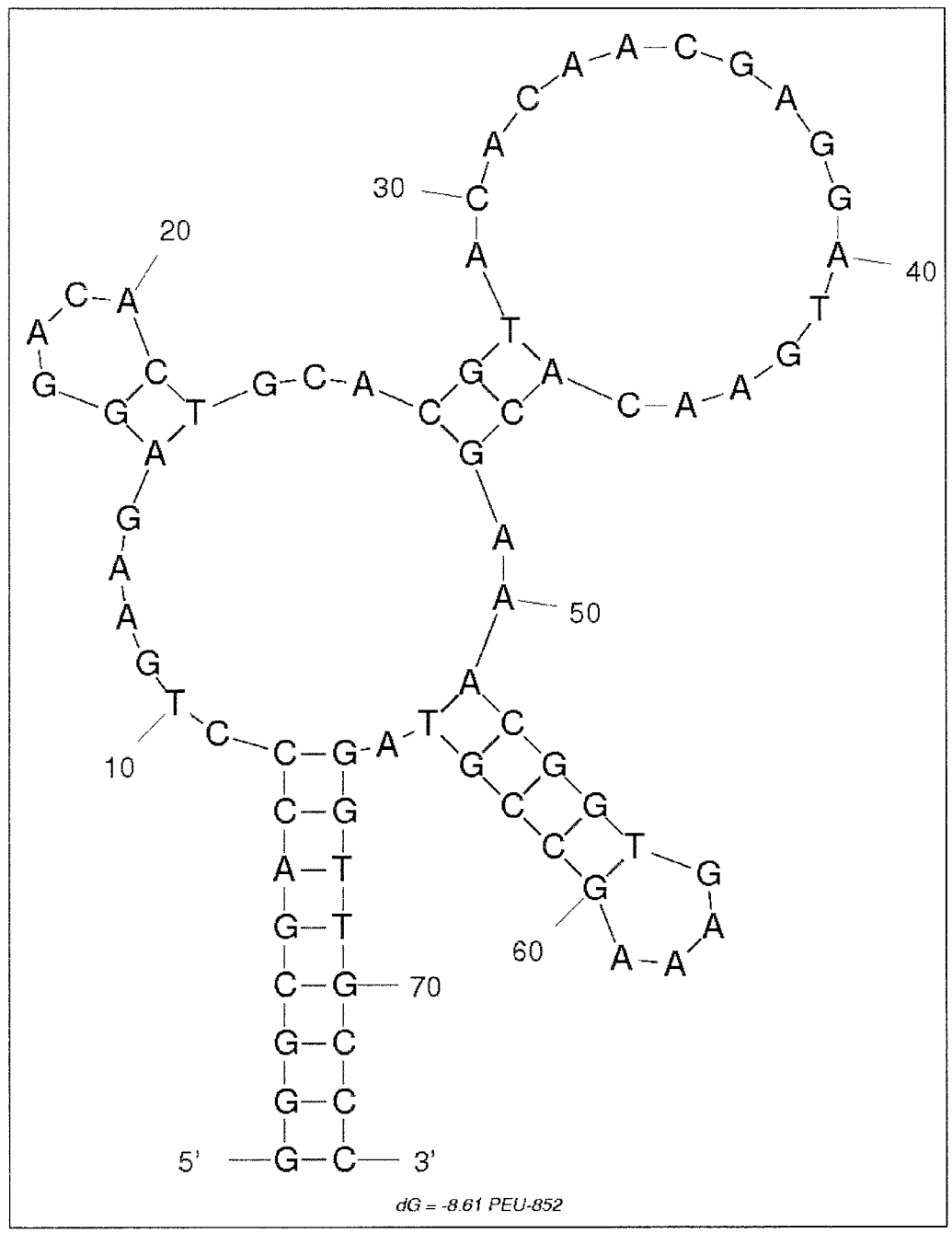
Figure 6c PEU-852

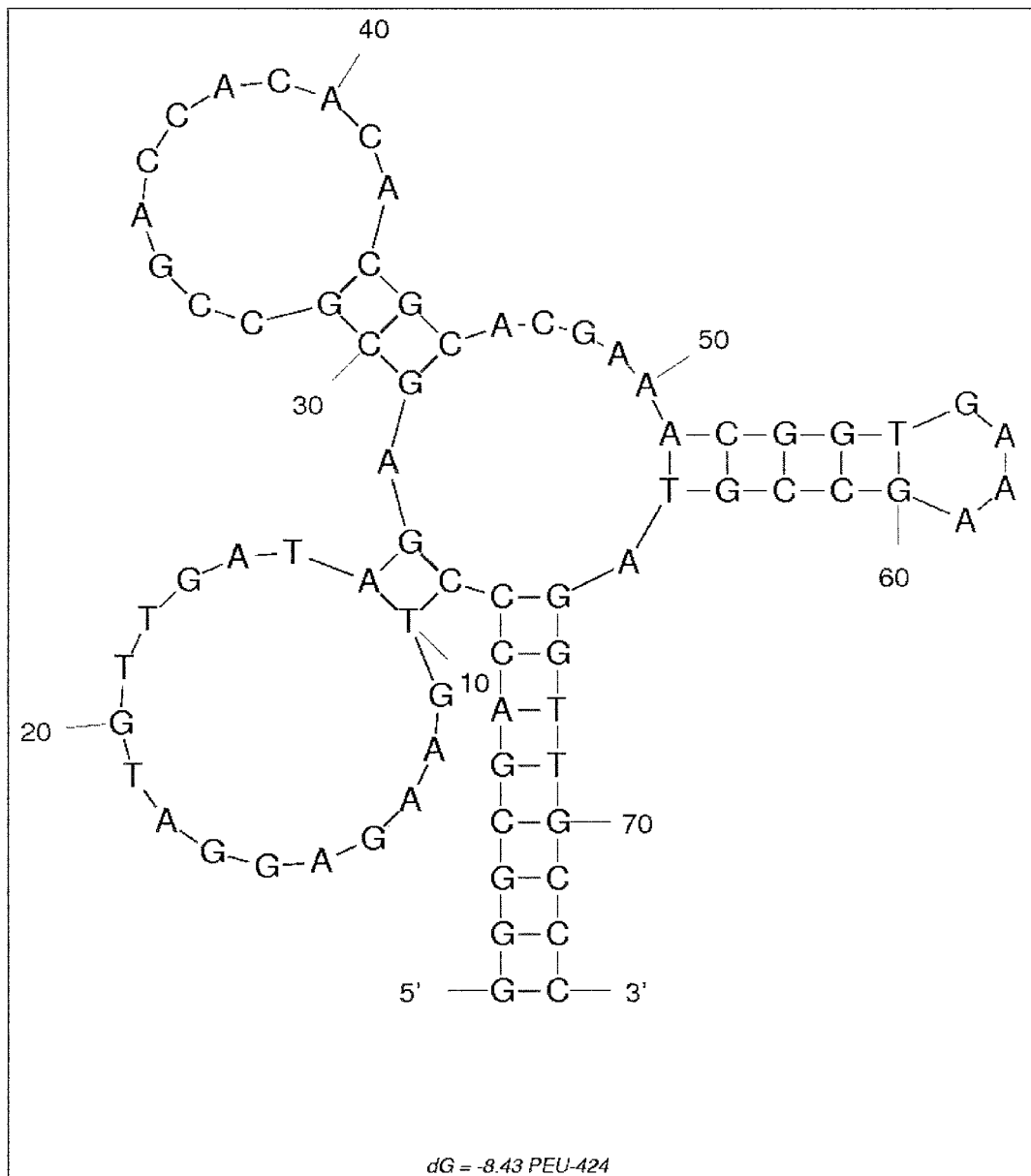
Figure 6d PEU-424

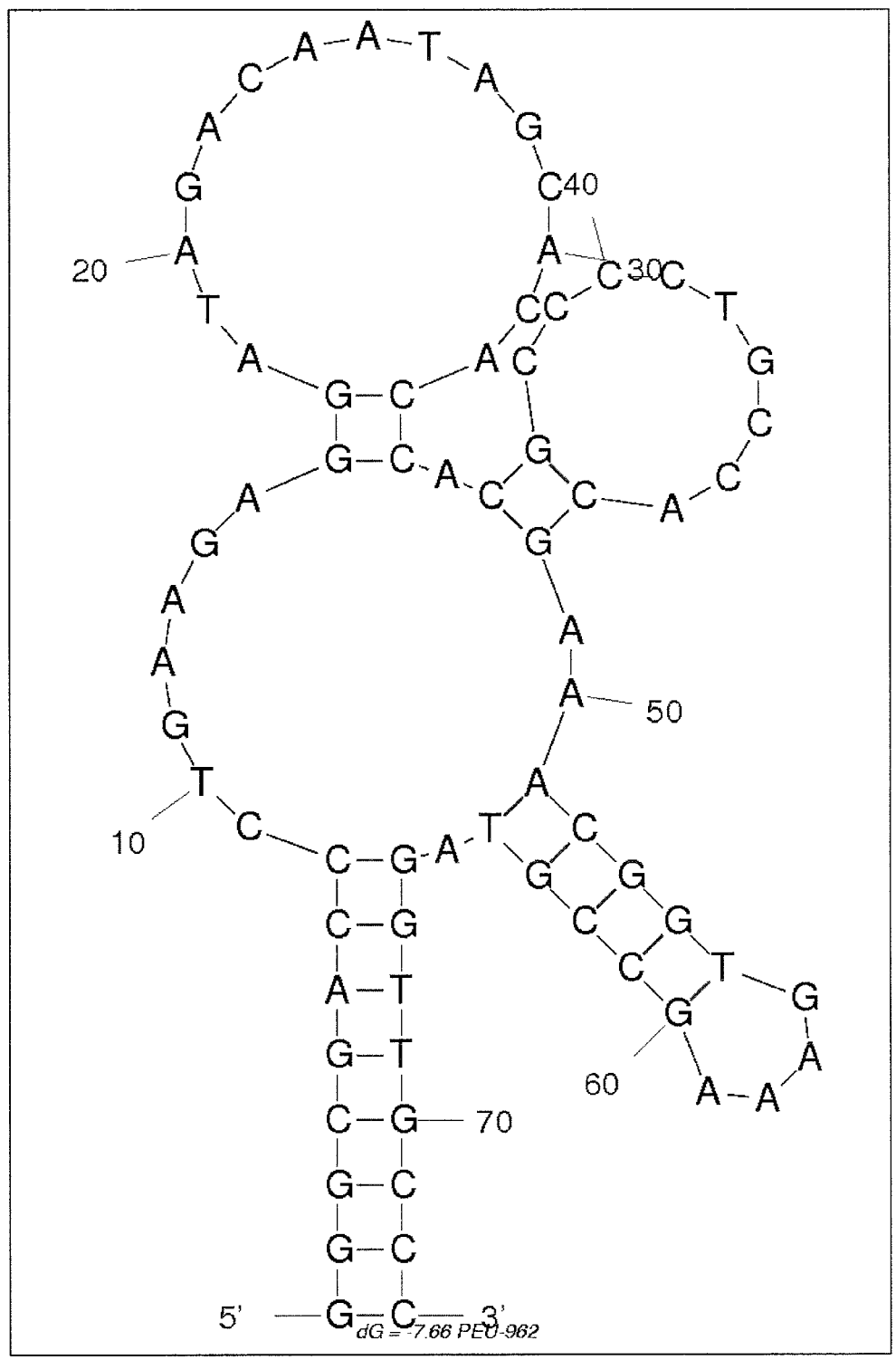
Figure 6e PEU-962

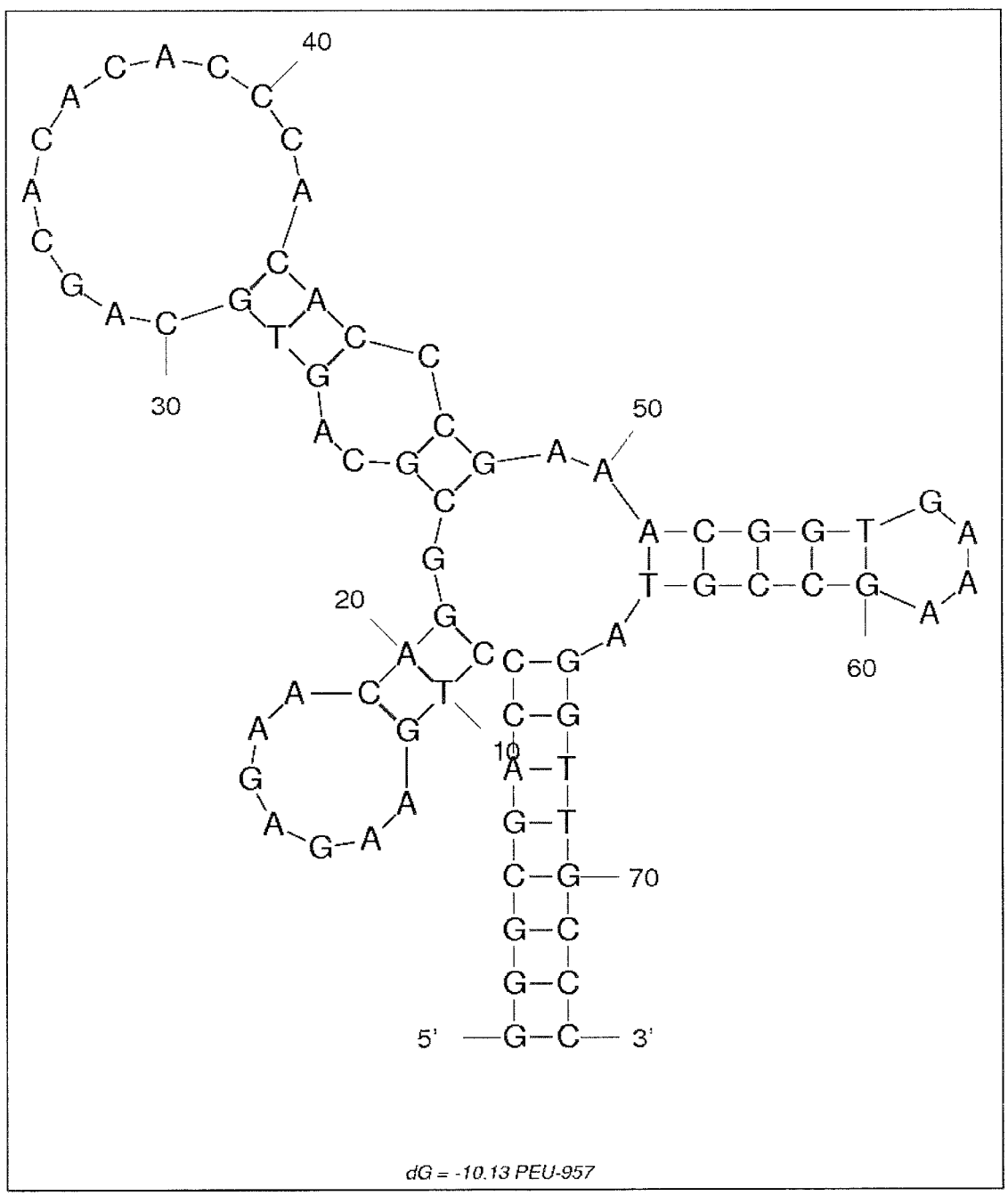
Figure 6f PEU-957

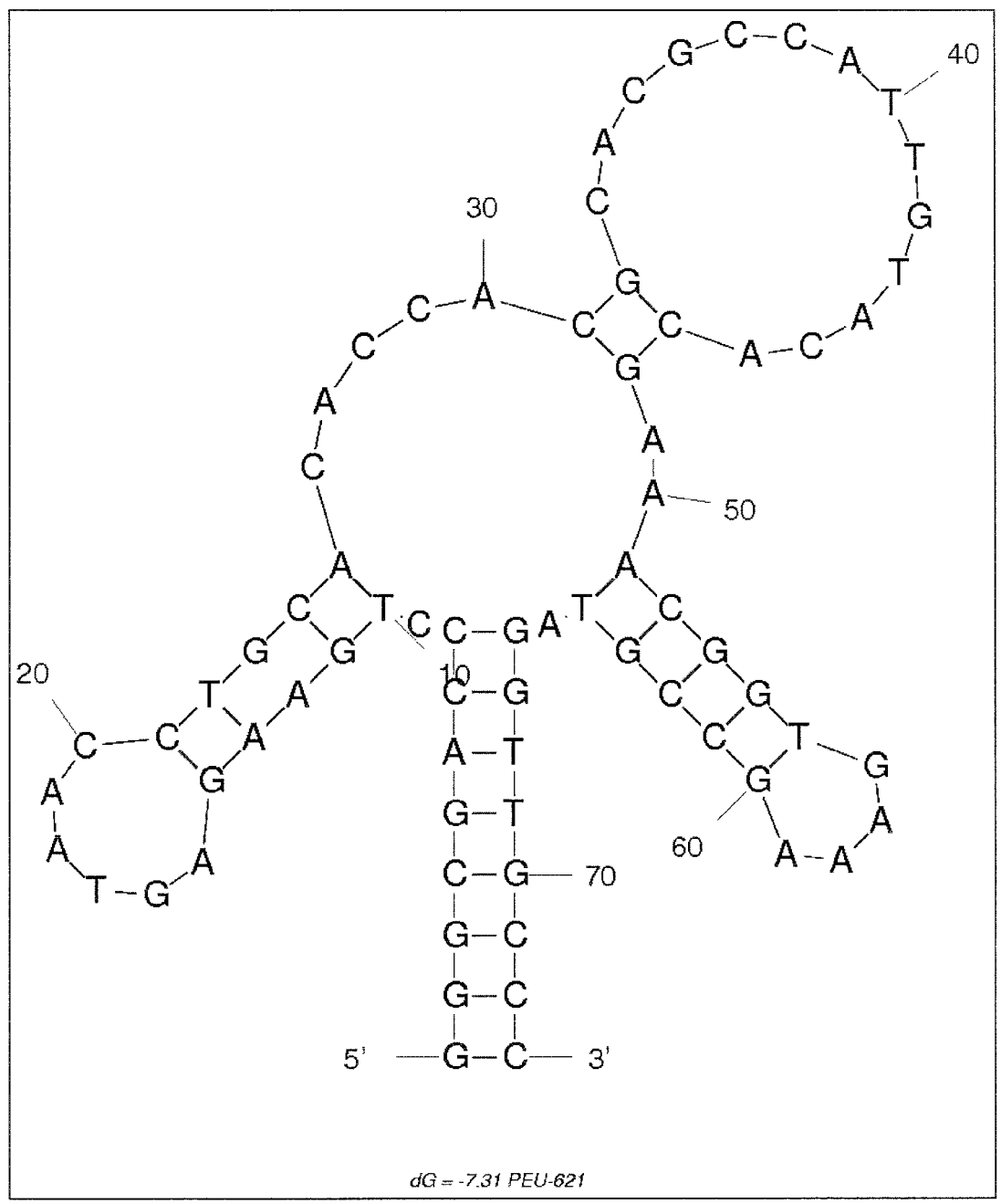
Figure 6g PEU-621

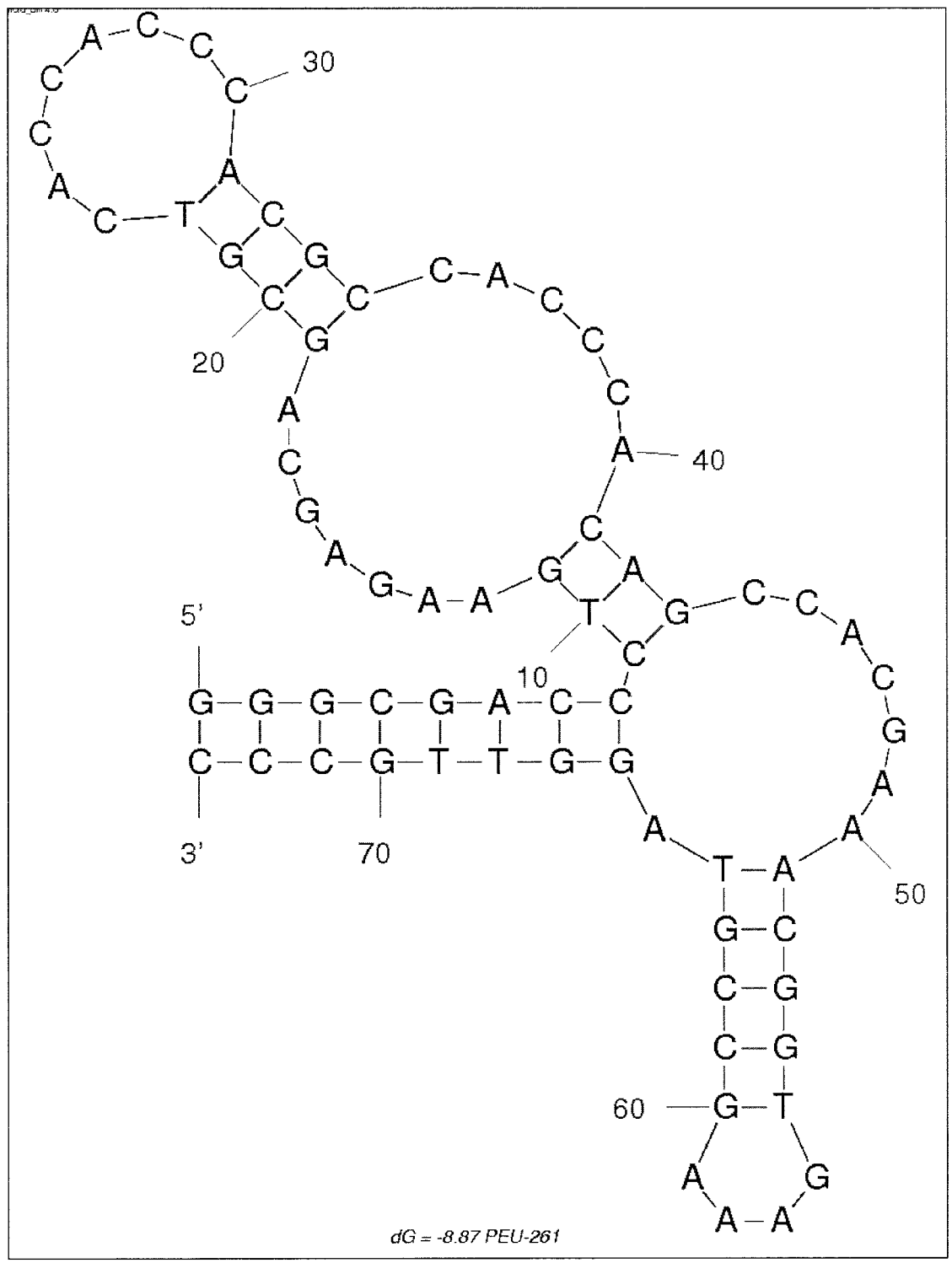
Figure 6h PEU-261

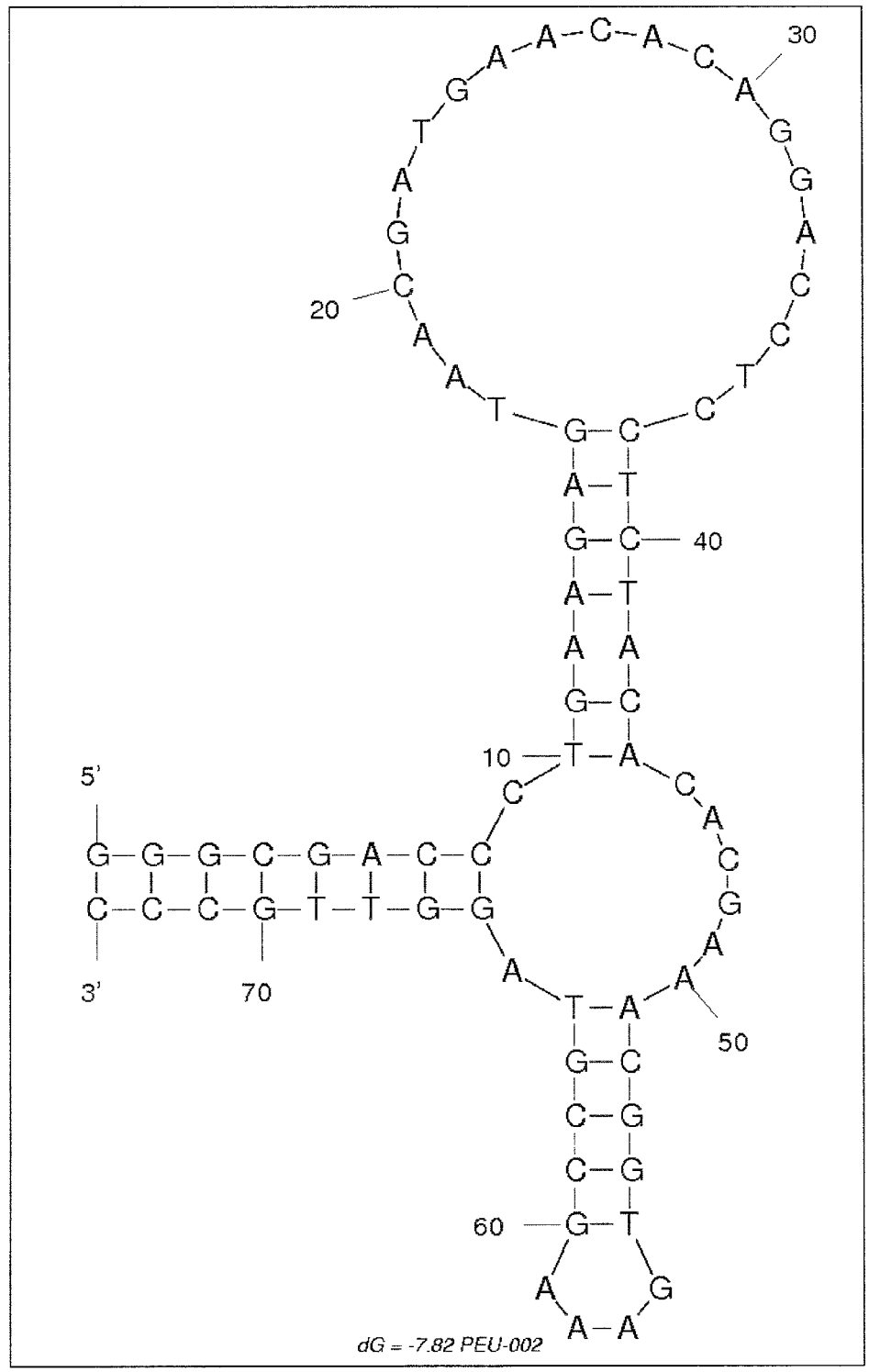
Figure 6i PEU-002

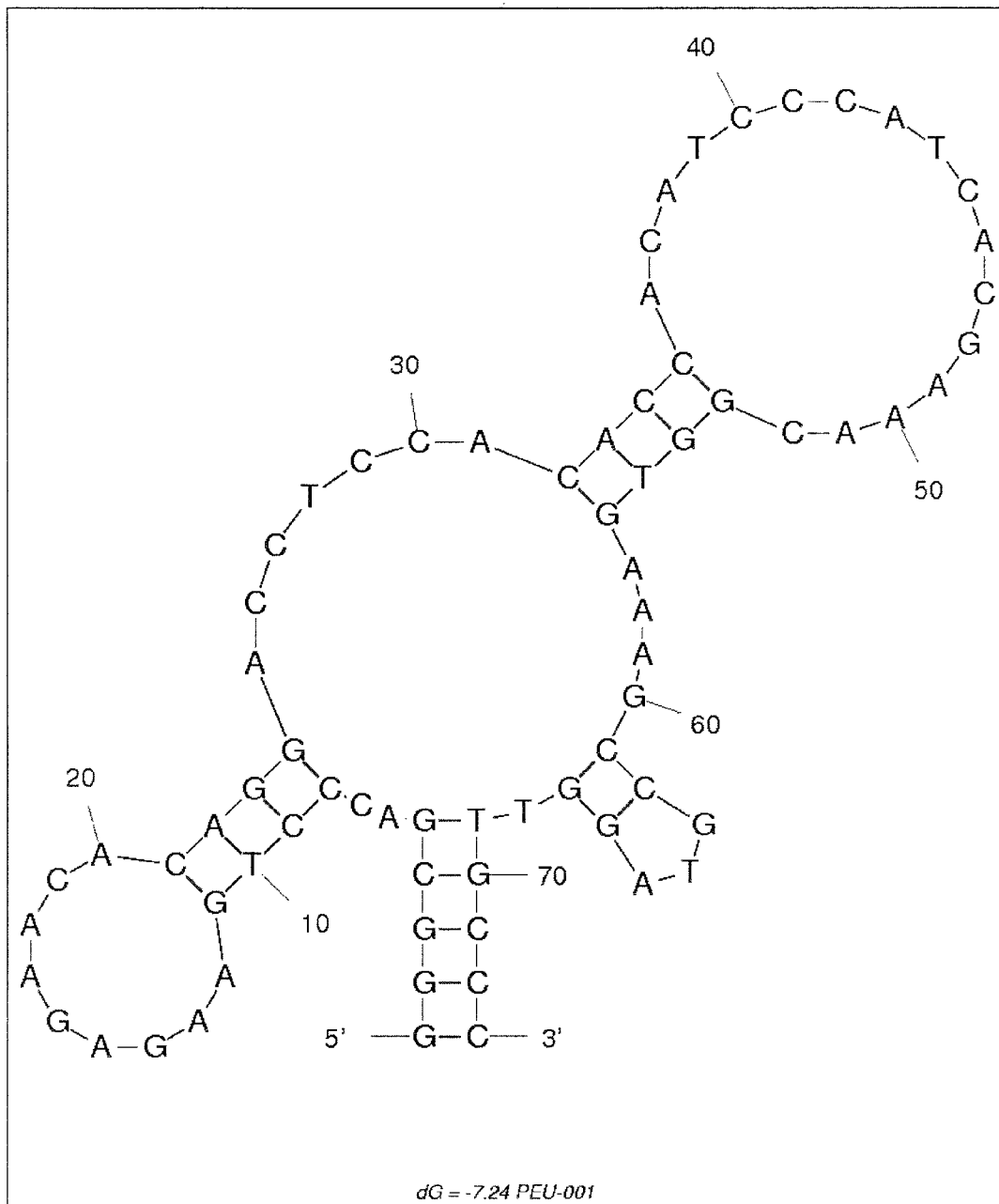
Figure 6j PEU-001

SEQUENCE LISTING

<160> NUMBER OF SEQ ID NOS: 26

<210> SEQ ID NO 1
<211> LENGTH: 200
<212> TYPE: PRT
<213> ORGANISM: PRRS Virus

<400> SEQUENCE: 1

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 2
<211> LENGTH: 173
<212> TYPE: PRT
<213> ORGANISM: PRRS Virus

<400> SEQUENCE: 2

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
    50                  55                  60

Phe Gln Ser Thr Lys Val Ala Leu Thr Met Gly Ala Val Val Ala Leu
65                  70                  75                  80

Leu Trp Gly Val Tyr Ser Ala Ile Glu Thr Trp Lys Phe Ile Thr Ser
                85                  90                  95

Arg Cys Arg Leu Cys Leu Leu Gly Arg Lys Tyr Ile Leu Ala Pro Ala
            100                 105                 110

His His Val Glu Ser Ala Ala Arg Phe His Pro Ile Ala Ala Asn Asp

```
                    115                 120                 125
Asn His Ala Phe Val Val Arg Arg Pro Gly Ser Thr Thr Val Asn Gly
    130                 135                 140

Thr Leu Val Pro Gly Leu Lys Ser Leu Val Leu Gly Arg Lys Ala
145                 150                 155                 160

Val Lys Gln Gly Val Val Asn Leu Val Lys Tyr Ala Lys
                165                 170

<210> SEQ ID NO 3
<211> LENGTH: 16
<212> TYPE: PRT
<213> ORGANISM: Artificial Sequence
<220> FEATURE:
<223> OTHER INFORMATION: M ectodomain

<400> SEQUENCE: 3

Met Gly Ser Ser Leu Asp Asp Phe Cys His Asp Ser Thr Ala Pro Gln
1               5                   10                  15

<210> SEQ ID NO 4
<211> LENGTH: 31
<212> TYPE: PRT
<213> ORGANISM: Artificial Sequence
<220> FEATURE:
<223> OTHER INFORMATION: GP5 ectodomain

<400> SEQUENCE: 4

Ala Ser Asn Asp Ser Ser Ser His Leu Gln Leu Ile Tyr Asn Leu Thr
1               5                   10                  15

Leu Cys Glu Leu Asn Gly Thr Asp Trp Leu Ala Asn Lys Phe Asp
            20                  25                  30

<210> SEQ ID NO 5
<211> LENGTH: 78
<212> TYPE: DNA
<213> ORGANISM: Artificial Sequence
<220> FEATURE:
<223> OTHER INFORMATION: Aptamer

<400> SEQUENCE: 5
gggcgaccct gaagagaaag gtgagtttat tgcggggtt atttattgct cgaaacggt      60 gaaagccgta ggttgccc                                                  78

<210> SEQ ID NO 6
<211> LENGTH: 77
<212> TYPE: DNA
<213> ORGANISM: Artificial Sequence
<220> FEATURE:
<223> OTHER INFORMATION: Aptamer

<400> SEQUENCE: 6
gggcgaccct gaagagtttt atgatgtgtt ggttagtata tgttattctc cgaaacggtg    60
aaagccgtag gttgccc                                                   77

<210> SEQ ID NO 7
<211> LENGTH: 78
<212> TYPE: DNA
<213> ORGANISM: Artificial Sequence
<220> FEATURE:
<223> OTHER INFORMATION: Aptamer

<400> SEQUENCE: 7
gggcgaccct gaagagaggt gtacatctaa tgctcgggtc ctcagcagtg tcgaaacggt    60
```

```
gaaagccgta ggttgccc                                                    78

<210> SEQ ID NO 8
<211> LENGTH: 78
<212> TYPE: DNA
<213> ORGANISM: Artificial Sequence
<220> FEATURE:
<223> OTHER INFORMATION: Aptamer

<400> SEQUENCE: 8
gggcgaccct gaagagatgt tcgttttcta tgatatttct tgggatcgta tcgaaacggt      60
gaaagccgta ggttgccc                                                    78

<210> SEQ ID NO 9
<211> LENGTH: 76
<212> TYPE: DNA
<213> ORGANISM: Artificial Sequence
<220> FEATURE:
<223> OTHER INFORMATION: Aptamer

<400> SEQUENCE: 9
gggcgaccct gaagagtttg taatctgcga ttttaaagtt gagtcgtcgc gaaacggtga      60
aagccgtagg ttgccc                                                      76

<210> SEQ ID NO 10
<211> LENGTH: 73
<212> TYPE: DNA
<213> ORGANISM: Artificial Sequence
<220> FEATURE:
<223> OTHER INFORMATION: Aptamer

<400> SEQUENCE: 10
gggcgaccct gaagaggcgg atggtggtta gtatgctgcg cctgtacgaa acggtgaaag      60
ccgtaggttg ccc                                                         73

<210> SEQ ID NO 11
<211> LENGTH: 79
<212> TYPE: DNA
<213> ORGANISM: Artificial Sequence
<220> FEATURE:
<223> OTHER INFORMATION: Aptamer

<400> SEQUENCE: 11
gggcgaccct gaagaggttt gcatattata gttataggag gtgtgtaatg gacgaaacgg      60
tgaaagccgt aggttgccc                                                   79

<210> SEQ ID NO 12
<211> LENGTH: 77
<212> TYPE: DNA
<213> ORGANISM: Artificial Sequence
<220> FEATURE:
<223> OTHER INFORMATION: Aptamer

<400> SEQUENCE: 12
gggcgaccct gaagagactg gtgagttaat gttttttctt agccttgtat cgaaacggtg      60
aaagccgtag gttgccc                                                     77

<210> SEQ ID NO 13
<211> LENGTH: 77
<212> TYPE: DNA
<213> ORGANISM: Artificial Sequence
<220> FEATURE:
```

```
<223> OTHER INFORMATION: Aptamer

<400> SEQUENCE: 13
gggcgaccct gaagagatgc ggtgcttgcc aagatggata ggatatggct cgaaacggtg      60
aaagccgtag gttgccc                                                    77

<210> SEQ ID NO 14
<211> LENGTH: 78
<212> TYPE: DNA
<213> ORGANISM: Artificial Sequence
<220> FEATURE:
<223> OTHER INFORMATION: Aptamer

<400> SEQUENCE: 14
gggcgaccct gaagagtaca tattgtgaag atttcggcgg gacaccgtta acgaaacggt      60
gaaagccgta ggttgccc                                                   78

<210> SEQ ID NO 15
<211> LENGTH: 73
<212> TYPE: DNA
<213> ORGANISM: Artificial Sequence
<220> FEATURE:
<223> OTHER INFORMATION: Aptamer

<400> SEQUENCE: 15
gggcgaccct gaagagtaca cacgggacac acacacactc actagacgaa acggtgaaag      60
ccgtaggttg ccc                                                        73

<210> SEQ ID NO 16
<211> LENGTH: 73
<212> TYPE: DNA
<213> ORGANISM: Artificial Sequence
<220> FEATURE:
<223> OTHER INFORMATION: Aptamer

<400> SEQUENCE: 16
gggcgaccct gaagaggacc agaagcacgg accacacaca gcgtatcgaa acggtgaaag      60
ccgtaggttg ccc                                                        73

<210> SEQ ID NO 17
<211> LENGTH: 73
<212> TYPE: DNA
<213> ORGANISM: Artificial Sequence
<220> FEATURE:
<223> OTHER INFORMATION: Aptamer

<400> SEQUENCE: 17
gggcgaccct gaagaggaca ctgcacgtac acaacgagga tgaacacgaa acggtgaaag      60
ccgtaggttg ccc                                                        73

<210> SEQ ID NO 18
<211> LENGTH: 73
<212> TYPE: DNA
<213> ORGANISM: Artificial Sequence
<220> FEATURE:
<223> OTHER INFORMATION: Aptamer

<400> SEQUENCE: 18
gggcgaccct gaagaggatg ttgatagagc gccgaccaca cacgcacgaa acggtgaaag      60
ccgtaggttg ccc                                                        73
```

```
<210> SEQ ID NO 19
<211> LENGTH: 73
<212> TYPE: DNA
<213> ORGANISM: Artificial Sequence
<220> FEATURE:
<223> OTHER INFORMATION: Aptamer

<400> SEQUENCE: 19
gggcgaccct gaagaggata gacaatagca caccacgccc ctgccacgaa acggtgaaag    60
ccgtaggttg ccc                                                      73

<210> SEQ ID NO 20
<211> LENGTH: 73
<212> TYPE: DNA
<213> ORGANISM: Artificial Sequence
<220> FEATURE:
<223> OTHER INFORMATION: Aptamer

<400> SEQUENCE: 20
gggcgaccct gaagagaaca ggcgcagtgc agcacacacc cacacccgaa acggtgaaag    60
ccgtaggttg ccc                                                      73

<210> SEQ ID NO 21
<211> LENGTH: 73
<212> TYPE: DNA
<213> ORGANISM: Artificial Sequence
<220> FEATURE:
<223> OTHER INFORMATION: Aptamer

<400> SEQUENCE: 21
gggcgaccct gaagagtaac ctgcacacca cgcacgccat tgtacacgaa acggtgaaag    60
ccgtaggttg ccc                                                      73

<210> SEQ ID NO 22
<211> LENGTH: 73
<212> TYPE: DNA
<213> ORGANISM: Artificial Sequence
<220> FEATURE:
<223> OTHER INFORMATION: Aptamer

<400> SEQUENCE: 22
gggcgaccct gaagagcagc gtcaccaccc acgccaccca cagccacgaa acggtgaaag    60
ccgtaggttg ccc                                                      73

<210> SEQ ID NO 23
<211> LENGTH: 73
<212> TYPE: DNA
<213> ORGANISM: Artificial Sequence
<220> FEATURE:
<223> OTHER INFORMATION: Aptamer

<400> SEQUENCE: 23
gggcgaccct gaagagtaac gatgaacaca ggacctcctc tacacacgaa acggtgaaag    60
ccgtaggttg ccc                                                      73

<210> SEQ ID NO 24
<211> LENGTH: 73
<212> TYPE: DNA
<213> ORGANISM: Artificial Sequence
<220> FEATURE:
<223> OTHER INFORMATION: Aptamer

<400> SEQUENCE: 24
```

```
gggcgaccct gaagagtaac gatgaacaca ggacctcctc tacacacgaa acggtgaaag       60
ccgtaggttg ccc                                                         73

<210> SEQ ID NO 25
<211> LENGTH: 16
<212> TYPE: DNA
<213> ORGANISM: Artificial Sequence
<220> FEATURE:
<223> OTHER INFORMATION: 5'-Primer

<400> SEQUENCE: 25
gggcgaccct gaagag                                                      16

<210> SEQ ID NO 26
<211> LENGTH: 27
<212> TYPE: DNA
<213> ORGANISM: Artificial Sequence
<220> FEATURE:
<223> OTHER INFORMATION: 3'-Primer

<400> SEQUENCE: 26
cgaaacggtg aaagccgtag gttgccc                                          27
```

APTAMERS, NUCLEIC ACID MOLECULES, POLYNUCLEOTIDES, SYNTHETIC ANTIBODIES COMPOSITIONS FOR DETECTING PRRS VIRUSES AND TREATING PRRS VIRUS INFECTION

CROSS-REFERENCE TO RELATED APPLICATION

This application claims priority to Canadian Application No. 2,914,337 filed Dec. 10, 2015, which hereby is incorporated by reference in its entirety.

FIELD

The present invention relates to aptamers, nucleic acid molecules, polynucleotides, synthetic antibodies and pharmaceutical compositions containing same, which can be utilized for detecting and treating PRRSV infection in swines

BACKGROUND

The pork industry in US is a $97B business and is standing to lose hundreds of millions of dollars in the case of mass outbreak from infectious diseases. The recent estimates of the cost of porcine Reproductive and Respiratory Syndrome Virus (PRRSV) to the US and Canadian swine industry have soared beyond $750M million "hard" dollars per year. When the soft costs are added, the total is near to $1.2 billion annually. Even higher costs have been found to prevail for the European swine industry[i]. The ability to detect the PRRSV is thus a fundamental issue in controlling the spread of the disease[ii]. None of the current vaccines (killed-virus and modified-live vaccines) is able to completely prevent respiratory infection, transplacental transmission, as well as pig-to-pig transmission of the virus, especially against heterologous infection[iii].

PRRSV causes a persistent and sometimes severe disease that is characterized by respiratory problems, weight loss and poor growth performance, as well as reproductive failure in pregnant sows[iv]. While the actual vaccines are ineffective against most phenotypes of the PRRS virus and are limited by severe side effects and acquired resistance, the use of Pulmotil® (Tilmicosin) is an antibiotic associated with reduced mortality due to pneumonia and improved performance despite the presence of circulating PRRS[v]. However, Pulmotil is highly priced.

Structure of the PRRS Virus

PRRSV is a member of the Arteriviridae family of enveloped viruses with positive-sense (+) RNA genomes. PRRSV is divided into two genotypes, the European, or type 1 virus, also known as Lelystad virus (LV), and the American, or type 2 virus. There is considerable sequence variability within both groups and only about 50-60% sequence identity between the two subtypes[vi]. Both subtypes now have a worldwide distribution[vii].

Recently, structures of the virion and some of the viral proteins, obtained by electron microscopy (EM) and X-ray crystallography, as well as in vitro and in vivo studies of protein-protein interactions have led to an improved understanding of PRRSV structure, assembly and infection process and shed light on the structural relationships between different nidoviruses. In particular, cryo-electron tomography reveals the pleiomorphic morphology of the PRRSV virions in greater detail and in three dimensions[viii].

FIG. 1a shows schematic view of all the main envelope proteins at the surface of the PRRSV. The envelope proteins of the PRRSV can be divided in two folds; (i) the major proteins that include the M and the GP5, and (ii) the minor proteins that include the GP2, GP3, GP4, and the E.

In FIG. 1a the stippled boxes represent predicted signal peptides while the broken lines indicate the cleavage sites. Glycosylation is indicated by hexagons with the corresponding residues numbered. The disulphide link between M and GP5 is also indicated. E forms homo-oligomers and is shown as a trimmer.

The Major Envelope Proteins M and GP5

The major components of the PRRSV envelope are GP5 and M, which together comprise at least half of the viral protein and form disulphide-linked heterodimers in the PRRS virus[iv,ix]. Deletion of either of these two ORFS from an infectious PRRSV clone led to a failure to produce viral particles, while deletion of the minor envelope proteins did not have an effect on viral production. From sequence-based topology prediction (TMHMM and HMMTOP), the non-glycosylated 174 residue M protein (173 for type 1) contains a short 16-residue N-terminal ectodomain followed by three transmembrane (TM) segments and an 84-residue C-terminal endodomain as shown in FIG. 1b. The M is the most highly conserved structural protein of PRRSV.

The glycosylated 200-residue (201 for type I) GP5 protein is the most variable protein of PRRSV, with only 51-55% sequence identity between the European and American subtypes. Hyper-variability in GP5 is responsible for the lack of immunological cross-reaction between viruses. Sequence analysis (SignalP 3.0, http://www.cbs.dtu.dk/services/SignalP-3.0/) have indicated that residues 1-31 constitute an N-terminal signal sequence, which is followed by a predicted ectodomain that is glycosylated on Asn 44 and Asn 51 (Asn 46 and Asn 53 in type I).

Residues 60-125 of GP5 comprise a hydrophobic region that includes either one or three transmembrane (TM) helices [iv, D.van Aken et al., Proteolytic maturation of replicase polyprotein pp1a by the nsp4 main proteinase is essential for equine arteritis virus replication and includes internal cleavage of nsp7 J. Gen. Virol. 2006,vol. 87, pp. 3473-3482.16]. Analysis of the PRRSV type 2 GP5 protein by TMHMM and HMMTOP predicts clearly only the last TM helix, between residues 107 and 125 as shown in FIG. 1b. A possible second TM helix is predicted between 63 and 82 in type 2 and, more strongly, between 68 and 90 in type 1. However, a second TM helix in this location would place the glycosylation sites of the ectodomain on the inside of the virus, an implausible arrangement. While the evidence is not conclusive, this comparison suggests that three TM helices are present in PRRSV as well. In this case, the PRRSV GP5 ectodomain is only about 30 residues long, which would explain the very smooth appearance of PRRSV virions by EM.

Given the impact of PRRSV on the porcine industry, the challenge at present is to detect airborne PRRS viruses or to generate highly potent prophylactic tools that can be used to prevent PRRSV infection in subjects that are at considerable risk of infection such as pregnant sows and young piglets.

Detecting the PRRS Virus

Detection of PRRSV is typically performed by genetic sequence analysis methods[x]. These methods employ a variety of techniques, such as reverse transcriptase-polymerase chain reaction (RT-PCR) assays, restriction fragment length polymorphism (RFLP), reverse transcription loop-mediated isothermal amplification (RT-LAMP), or sequence analysis[xi]. However, most of the existing genome-based detection methods are limited by their high cost, time-consuming procedures, and reliance on expensive and complicated equipment. Other methods have been developed on the basis of detection and quantitative analysis of antibodies against PRRSV using serological tests, including the indirect fluorescent antibody (IFA) test, the indirect enzyme immunoassay (EIA), and the serum virus neutralization (SVN) test[xii] However, these tests detect antibodies, and thus, they are unable to detect the PRRSV antigen itself. This means that these tests are not a direct measure of the infection level, because immunity to make antibodies against PRRSV infection typically takes several weeks and is undistinguishable from vaccination. In addition, the SVN test is expensive and time-consuming to perform. Therefore, such methods are not amenable to the early detection or control of PRRSV.

Aptamers are specific oligonucleotides composed of single stranded DNA (ssDNA) or RNA that bind to a wide range of targets specifically. Aptamers can be obtained using an in vitro selection procedure called Systematic Evolution of Ligands by EXponential enrichment (SELEX), that starts with the incubation of random oligonucleotide libraries with the desired target molecules, followed by the separation and amplification of bound oligonucleotides[xiii]. The production of aptamers is not costly, and they are very low in batch-to-batch variation compared to the antibodies produced in vivo. In addition, aptamers can be chemically synthesized, are thermally stable, and are suitable for long-term storage[xiv]. With these advantages, aptamers with high specificity and affinity have been developed for a variety of targets, including proteins, small molecules, whole cells, and viruses. Aptamers have now been widely used in diverse fields, such as diagnostics[xv], therapeutics[xvi], and biosensors[xvii], as an alternative to antibodies.

Previously, several aptamers against viral pathogens were developed for therapeutic purposes and pathogen detection. Viral pathogen-binding aptamers have been used in the molecular analysis of virus replication or the development of antiviral agents; these aptamers showed the efficient binding affinity or antiviral ability. To develop virus-binding aptamers, viral proteins rather than whole virus particles should be primarily used for aptamer screening[xviii]. In addition, several previous studies have used RNA aptamers, which have limited use due to rapid degradation while requiring chemical modifications (such as 2'-amino- and 2' fluoropyrimidine nucleotide) in the SELEX procedure. Chemical modifications can be introduced after the SELEX procedure only if there is no effect on the conformational structure[xix].

Development of Anti-PRRSV Agents

Modified live PRRSV vaccines (MLV) are the most effective option currently available for the control of the disease. Modified live PRRSV vaccines can confer solid protection against homologous reinfection and have significant effects in reducing viral shedding[xx]. But the vaccine efficacy varies upon heterologous challenge[xxi]. None of the current vaccines is able to completely prevent respiratory infection, transplacental transmission, as well as pig-to-pig transmission of the virus. More importantly, the intrinsic risk of MLV vaccine to revert to virulent virus under farm conditions poses a great safety concern. The lack of efficacy and safety of current PRRSV vaccines has been driven the continuous efforts of developing a new generation of vaccines.

The new experimental PRRSV vaccines that have been reported in the recent years include (a) live attenuated vaccines, (b) recombinant vectors expressing PRRSV viral proteins, (c) DNA vaccines, and (d) plant-made subunit vaccines. In parallel new aptamer-based sandwich type assays have been developed for quick detection of the PRRS viruses.

DNA Vaccines—

This approach involves the topical administration or administration via injection of plasmid DNA encoding one or more PRRSV proteins[xxii]. DNA vaccines are another strategy for PRRSV vaccine development[xxiii]. In all cases, GP5 was selected as a candidate for subunit vaccines and the efficacy of DNA vaccination by immunizing pigs with a plasmid encoding GP5 was tested. DNA-vaccinated pigs were protected from generalized viremia and typical macroscopic lung lesions. The severity of interstitial pneumonitis and broncho-alveolitis were also found to be reduced. Similar to recombinant vector-based PRRSV vaccine development, the strategy of co-expressing several viral proteins was also used to enhance the immunogenicity of the DNA vaccine candidates[xxiv]. It was reported that a DNA vaccine expressing GP5 and M proteins simultaneously could form GP5/M hetero-dimeric complex in transfected cells. The DNA vaccine induced significantly higher neutralization antibody titres and lymphocyte proliferation responses than those by DNA vaccines expressing GP5 or M individually.

Adjuvants for PRRSV Vaccines—

To date, adjuvants including cytokines, chemical reagents and bacterial products have all been examined to potentiate the immune response conferred by PRRS killed vaccines, modified live attenuated vaccines, DNA vaccines, recombinant vector-based vaccines and synthetic peptide vaccines. Some of them do increase the immunogenicity of the adjuvanted PRRS vaccines, but to date, only few of them received appreciative results of enhanced immune response or increased vaccine efficacy.

SUMMARY

Despite overall advantages, the widespread use of currently available antiviral agents is limited by concerns over side effects, and the possible emergence of drug-resistant variants. It would be highly advantageous to have compositions, which can be used to diagnose and treat PRRSV infection devoid of the above limitations. The ideal therapeutically safe and effective antiviral drugs would selectively affect specific processes of the target virus with minimal side effects on normal cellular pathways.

Thus it is an object of the present invention to provide nucleic acid compounds which are useful for detecting PRRSV type I and type II.

A further object of the present invention is to provide nucleic acid molecules which have an antiviral effect to both types of PRRSV.

A third object of the present invention is to provide compounds useful for vaccination against both types of PRRSV.

A fourth object of the present invention is to provide methods for generating a method for generating nucleic acid compounds having diagnostic and therapeutic capability relative to both types of PRRSV.

A fifth object of the present invention is to provide pharmaceutical compositions useful for treatment of subjects infect with at least one of both types of PRRSV.

According to one aspect of the present invention there are provided for each type of PRRSV, at least three nucleic acid molecules comprising polynucleotide sequences capable of specifically binding a polypeptidic complex participating in the PRRSV infection of cells.

According to further features in preferred embodiments of the invention described below, the polynucleotide sequence is selected from the group consisting of A505, A507, and A508 for type 2 PRRSV, and consisting of PEU-499, PEU-842, PEU-852, PEU-424, AND PEU-962 for type 1 PRRSV.

According to still further features in the described preferred embodiments the polypeptide in the polypeptidic complex is a PRRSV polypeptide.

According to still further features in the described preferred embodiments, the polynucleotide sequence is capable of binding a region of the M-S-S-GP5 surface proteins of the PRRSV that control binding of the virus unto the PAM, and defined by amino acid coordinates 1-16 of the M protein and 31 to 54 of the GP5 protein. M and GP5 are disulphide linked between Cys 9 of M and Cys 48 of GP5 for type 2 strains and between Cys 8 and Cys 50 in type 1 strains.

According to still further features in the described preferred embodiments, the M-S-S-GP5 polypeptide is a host cell polypeptide.

According to still further features in the described preferred embodiments the host cell polypeptide is a heparin sulphate/sialoadhesin receptor.

According to another aspect of the present invention there is provided a method of generating a molecule capable of inhibiting PRRSV infection, the method comprising: (a) provision of the glycosylated M-S-S-GP5 complex that controls PRRSV infection of cells; (b) contacting a plurality of nucleic acid molecules with the polypeptide complex; (c) identifying at least one nucleic acid molecule from the plurality of nucleic acid molecules capable of specifically binding the polypeptide complex; and (d) isolating the at least one nucleic acid molecule capable of binding the polypeptide complex, thereby generating the molecule capable of inhibiting PRRSV infection.

According to still further features in the described preferred embodiments the method further comprising generating the plurality of nucleic acid molecules using a combinatorial synthesis approach prior to (b).

According to still further features in the described preferred embodiments the method further comprising modifying the plurality of nucleic acid molecules prior to (b) or following (d).

According to still further features in the described preferred embodiments the method further comprising repeating steps (b) to (d).

According to yet another aspect of the present invention there is provided a pharmaceutical composition comprising a nucleic acid molecule including a polynucleotide sequence capable of specifically binding a polypeptide participating in PRRSV infection of cells and a physiologically acceptable carrier.

According to still another aspect of the present invention there is provided an article-of-manufacture comprising packaging material and a pharmaceutical composition identified for treating or preventing PRRSV infection being contained within the packaging material, the pharmaceutical composition including, as an active ingredient, a nucleic acid molecule including a polynucleotide sequence capable of specifically binding a polypeptide participating in PRRSV infection of cells.

According to an additional aspect of the present invention there is provided a method of treating or preventing PRRSV infection comprising providing to a subject in need thereof, a therapeutically effective amount of a nucleic acid molecule including a polynucleotide sequence capable of specifically binding a polypeptide participating in PRRSV infection of cells, thereby treating or preventing the PRRSV infection.

According to still further features in the described preferred embodiments the providing is implemented by: (i) administering of the nucleic acid molecule; and/or (ii) administering a polynucleotide expressing the nucleic acid molecule.

According to yet an additional aspect of the present invention there is provided a method of identifying PRRSV in a biological sample, the method comprising: (a) contacting the biological sample with a nucleic acid molecule including a polynucleotide sequence capable of specifically binding an PRRSV polypeptide; and (b) detecting the nucleic acid molecule bound to the PRRSV polypeptide in the biological sample, to thereby identify the PRRS infection.

According to still an additional aspect of the present invention there is provided a method of targeting an antiviral agent to a PRRSV infected tissue, the method comprising administering to a subject in need thereof a therapeutic effective amount of the antiviral agent conjugated to a nucleic acid molecule including a polynucleotide sequence capable of specifically binding a PRRSV polypeptide, thereby targeting the antiviral agent to the PRRSV infected tissue.

According to a further aspect of the present invention there is provided a composition of matter comprising an antiviral agent conjugated to a nucleic acid molecule including a polynucleotide sequence capable of specifically binding a polypeptide participating in PRRSV infection of cells.

According to still further features in the described preferred embodiments wherein the polypeptide is a PRRSV polypeptide.

According to still further features in the described preferred embodiments the polypeptide is selected from the group consisting of $M_{1-16}$-S-S-GP$5_{31-61}$, DNA-directed DNA polymerase core proteins, M structural matrix protein, and GP5 structural matrix proteins.

According to still further features in the described preferred embodiments the polynucleotide sequence is capable of binding a region of M-S-S-GP5 complex defined by amino acid coordinates $M_{1-16}$-S-S-GP$^5_{31-61}$.

According to still further features in the described preferred embodiments the polypeptide is a host cell polypeptide.

According to still further features in the described preferred embodiments the host cell polypeptide is a heparin sulphate/sialoadhesin receptor.

According to still further features in the described preferred embodiments the polynucleotide sequence is single stranded.

According to still further features in the described preferred embodiments the polynucleotide sequence is ssDNA.

According to still further features in the described preferred embodiments the nucleic acid molecule further comprises a detectable label.

According to still further features in the described preferred embodiments the polynucleotide sequence include FDG ([$^{18}$F]-2-fluoro-2-deoxy-D-glucose) and/or PEG modified nucleotides.

According to still further features in the described preferred embodiments the polynucleotide sequence is selected having a length between 10 to 45 nucleotides.

According to still further features in the described preferred embodiments the pharmaceutical composition further includes an agent.

According to still further features in the described preferred embodiments agent is selected from the group consisting of an immunomodulatory agent, an antiviral agent, an antisense molecule, and a ribozyme.

According to still further features in the described preferred embodiments the polynucleotide is as set forth in A505, A507, and A508 for type 2 PRRSV, and is as set forth in PEU-499, PEU-842, PEU-852, PEU-424, PEU-962 for type 1 PRRSV.

According to still further features in the described preferred embodiments the nucleic acid sequence is as set forth in A505, A507, and A508 for type 2 PRRSV, and PEU-499, PEU-842, PEU-852, PEU-424, and PEU-962 for type 1 PRRSV.

According to still further features in the described preferred embodiments the amino acid sequence is defined by amino acid coordinates 1-174 of the M protein and amino acid coordinates 1-128 of the GP5 protein.

According to still further features in the described preferred embodiments the amino acid sequence is defined by amino acid coordinates 1-96 of the M protein and amino acid coordinates 1-108 of the GP5 protein.

According to still further features in the described preferred embodiments the amino acid sequence is defined by amino acid coordinates 1-16 of the M protein and amino acid coordinates 31-61 of the GP5 protein for the corresponding aptamers; namely A505, A507, and A508 for type 2 PRRSV, and PEU-499, PEU-842, PEU-852, PEU-424, PEU-962 for type 1 PRRSV.

According to still further features in the described preferred embodiments the detecting the immuno complexes is implemented by quantifying intensity of the label following (b).

According to still a further aspect of the present invention there is provided a nucleic acid molecule as set forth in A505, A508, A507 for type 2 PRRSV, and PEU-499, PEU-842, PEU-852, PEU-424, PEU-962 for type 1 PRRSV.

The present invention has the general objective of addressing shortcomings of the presently known configurations by providing nucleic acid molecules, polynucleotides, synthetic antibodies generated there against and compositions containing the same that can be used to detect, diagnose, and treat PRRSV infection. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 1. Schematics showing the topology of the PRRSV envelope proteins.

FIGS. 5A-5J show 10 possible secondary structures as generated by QuickFold 3.0 software[xxv] of the candidate aptamers to neutralize type 2 PRRSv. These aptamers are A501 (SEQ ID NO. 5) (shown in FIG. 5A); A502 (SEQ ID No. 6) (shown in FIG. 5B); A503 (SEQ ID NO. 7) (shown in FIG. 5C); A504 (SEQ ID NO. 8) (shown in FIG. 5D); A505 (SEQ ID NO. 9) (shown in FIG. 5E); A506 (SEQ ID NO. 10) (shown in FIG. 5F); A507 (SEQ ID NO. 11) (shown in FIG. 5G); A508 (SEQ ID NO. 12) (shown in FIG. 5H), A509 (SEQ ID NO. 13) (shown in FIG. 5I); and A510 (SEQ ID NO. 14) (shown in FIG. 5J). Three of them, respectively A505, A508, A507, have been found to bind the M-S-S-GP5 heterodimer that controls the binding of the PRRSv on to the PAMs.

FIGS. 6A-6J show 10 possible secondary structures of candidate aptamers, as generated by QuickFold 3.0 software[xxvi], that neutralize type 1 (Lelystad) PRRSv. These aptamers are: PEU-499 (SEQ ID NO. 15) (shown in FIG. 6A); PEU-842 (SEQ ID No. 16) (shown in FIG. 6B); PEU-852 (SEQ ID NO. 17) (shown in FIG. 6C); PEU-424 (SEQ ID NO. 18) (shown in FIG. 6D); PEU-962 (SEQ ID NO. 19) (shown in FIG. 6E); PEU-957 (SEQ ID NO. 20) (shown in FIG. 6F); PEU-621 (SEQ ID NO. 21) (shown in FIG. 6G); PEU-261 (SEQ ID NO. 22) (shown in FIG. 6H); PEU-902 (SEQ ID NO. 23) (shown in FIG. 6I); and PEU-001 (SEQ ID NO. 24) (shown in FIG. 6J). Five of them, respectively PEU-499, PEU-842, PEU-852, PEU-424, PEU-962 have been found to bind the M-S-S-GP5 heterodimer that controls the binding of the PRRSv on to the PAMs.

FIGS. 7 a-c are schematic illustrations depicting nucleic acid modifications, which can be incorporated in the nucleic acid molecules of the present invention.

FIGS. 10 a-c are light microscope images of PAMs and MARC-145 cells following infection with PRRSV (FIG. 10a), following pre-treatment with A505 (FIG. 10b) or non-infected PAMs/MARC-145 cells. FIGS. 10 d-f are immunofluorescence images of PAMs and MARC-145 cells following two days of incubation with PRRS virus (FIG. 10d), PRRS virus and A505 (FIG. 10e), or A505 alone (FIG. 10f).

FIG. 11 illustrates strain-specific immune response induced by the intact type-2 VR2332, LHVA-93-3, NVSL-93-2335. Note that A505 has not effect on type-1 Lelystad PRRS virus.

DESCRIPTION OF THE PREFERRED EMBODIMENTS

Figure 1A:
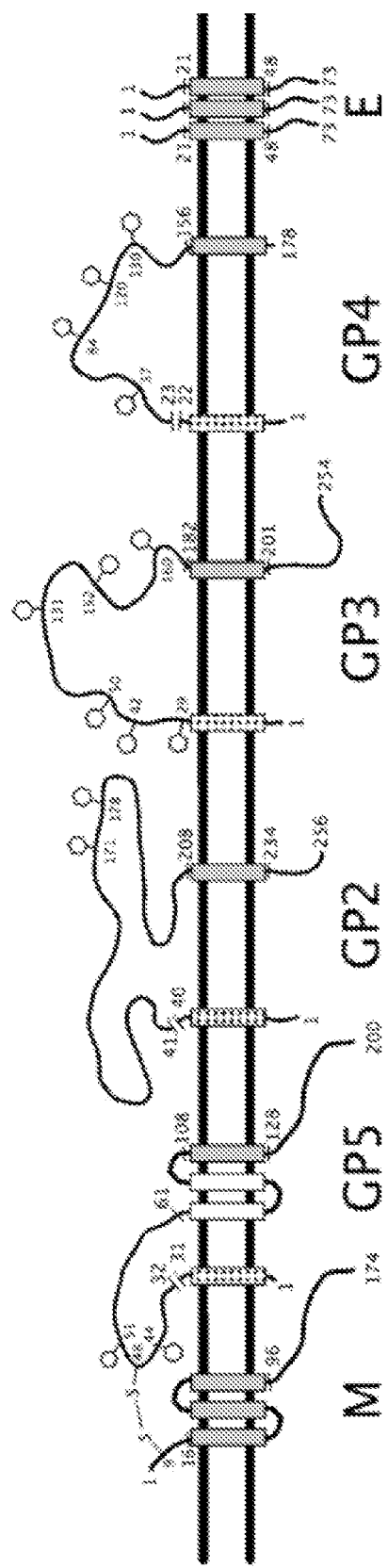
FIG. 1a shows the residue numbering is according to VR-2332 (type 2 strain). Transmembrane domains are shown as rectangles crossing the lipid bilayer. The stippled boxes represent predicted signal peptides while the broken lines indicate the cleavage sites. Glycosylation is indicated by hexagons with the corresponding residues numbered. The disulphide link between M and GP5 is also indicated. The protein E forms a homo-oligomer and is shown as a trimmer.
Figure 1B:
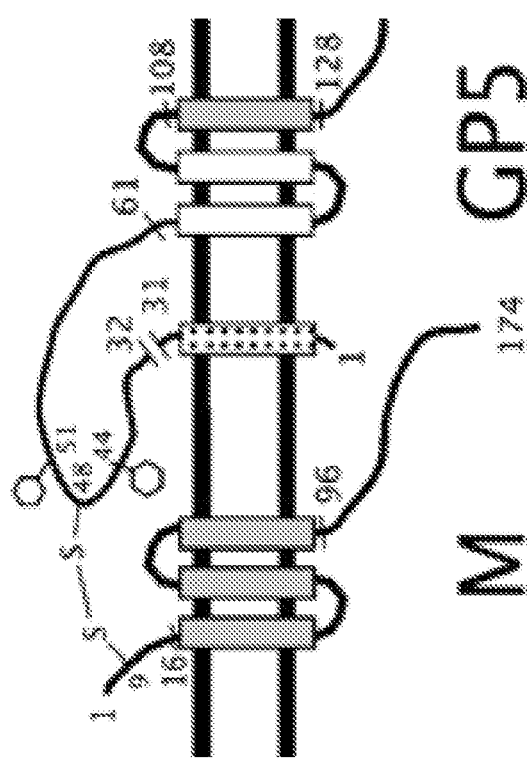
FIG. 1b shows a closer view of the binding domain for the PRRS virus (type 2 strains).

The present invention is of nucleic acid molecules, polynucleotides, synthetic antibodies, and pharmaceutical compositions that can be used for detecting and treating PRRS virus (PRRSV) infection in swine.

The principles and operation of the present invention may be better understood with reference to the drawings and accompanying descriptions. The invention is not limited in its application to the details set forth in the following description or exemplified by the Examples. It is only defined by the appended claims. Also, it is to be understood that the phraseology and terminology employed herein is for the purpose of description and should not be regarded as limiting.

The "Targeted Binding Site"

To produce the "targeted binding site" (i.e. the polypeptidic complex) that is needed for the determination (SELEX) of the aptamer for the PRRSV, we first proceed with synthesizing the {1-16} segment of the M protein, and the {31-61} segment of the GP5 protein. Note that the complete GP5 (SEQ ID NO: 1) envelope protein amino acids sequence is:

MLEKCLTAGCCSRLLSLWCIVPFCFAVLANASNDSSSHLQLIVNLTLCEL

NGTDWLANKFDWAVESFVIFPVLTHIVSYGALTTSHFLDTVALVTVSTAG

FVHGRYVLSSIYAVCALAALTCFVIRFAKNCMSWRYACTRYTNFLLDTKG

RLYRWRSPVIIEKRGKVEVEGHLIDLKRVVLDGSVATPITRVSAEQWGRP while the complete M matrix protein (SEQ ID NO: 2) amino acids sequence is:

MGSSLDDFCHDSTAPQKVLLAFSITYTPVMIYALKVSRGRLLGLLHLLIF

LNCAFTFGYMTFAHFQSTKVALTMGAVVALLWGVYSAIETWKFITSRCRL

CLLGRKYILAPAHHVESAARFHPIAANDNHAFVVRRPGSTTVNGTLVPGL

KSLVLGGRKAVKQGVVNLVKYAK

Note that the two former sequences do include the endo- and the ecto-domains of the protein.

Hence, the amino acids "binding sequence" of M protein (the ectodomain, SEQ ID NO: 3) is:

MGSSLDDFCHDSTAPQ
1...............16
Met Gly Ser Ser Leu Asp Asp Phe Cys His Asp Ser
Thr Ala Pro Gln while the corresponding amino acids binding sequences of the GP5 protein ectodomain (SEQ ID NO: 4) is:

ASNDSSSHLQLIYNLTLCELNGTDWLANKFD
31...........................61
Ala Ser Asn Asp Ser Ser Ser His Leu Gln Leu
Ile Tyr Asn Leu Thr Leu Cys Glu Leu Asn Gly
Thr Asp Trp Leu Ala Asn Lys Phe Asp

Various technologies are currently available to produce these two peptides.

The GP5$_{\{31-61\}}$ is glycosylated to maximise binding efficiency of the aptamer against the PRRSV. For the glycosylation, it is most important that Asn at position {44} be properly glycosylated while glycosylation of Asn at position {51} is a feature that is now deemed essential[xxvii]. Note that glycosylation takes place on the GP5 segment before the formation of the disulphide binding with the M segment[xxviii-xxix]. The glycans are N-linked complex glycans[xxx-xxxi]. This was deduced from the fact that the actual glycans at the virion's surface were affected by endoglycosidase F/N-glycosidase F (glyco F). Finally, we are proceeding with the oxidation and formation of a disulphide bond between the Cys at $M_{\{9\}}$ and Cys at $GP5_{\{48\}}$.

The oxidation of the Cys occurs in two steps[xxxii]. A variety of oxidants promote this reaction including air and hydrogen peroxide. Such reactions are thought to proceed via sulfonic acid as intermediate. In the laboratory, iodine in the presence of base is commonly employed to oxidize thiols to disulphides. Several metals, such as $Cu^{+2}$ (copper II) and $Fe^{+3}$ (iron III) complexes) effect this reaction.

Alternatively, disulphide bonds in proteins are often formed by thiol-disulphide exchange, i.e.: RS—SR+ R'SH⇌R'S—SR+RSH. Such reactions are mediated by enzymes in some cases and in other cases are under equilibrium control, especially in the presence of catalytic amount of base. The alkylation of alkali metal di- and polysulphides gives disulphides. "Thiokol" polymers arise when sodium polysulfide is treated with an alkyl dihalide. In the converse reaction, carbanionic reagents react with elemental sulphur to afford mixtures of the thioether, disulphide, and higher polysulphides. These reactions are often unselective but can be optimized for specific applications. A specialized method was developed for forming disulphide bond between the M and GP5 segments[xxxiii].

Determination of the ssDNA Aptamers for the PRRS Viruses

Figure 2:
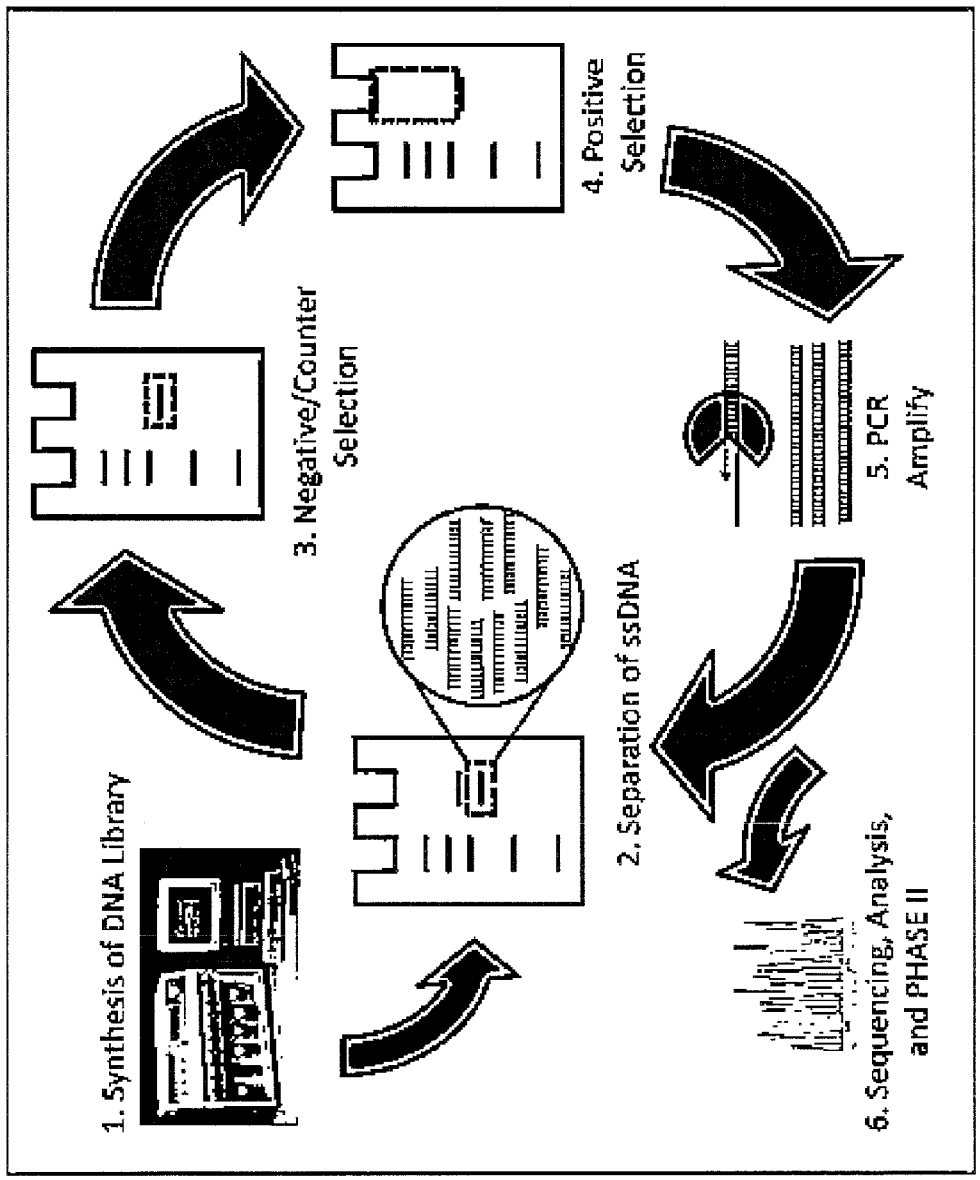
FIG. 2 gives a schematic illustration of the aptamer selection strategy

Using the glycosylated $M_{\{1-16\}}$-S-S-$GP5_{\{31-61\}}$ polypeptidic complex, the corresponding binding aptamers were identified using the SELEX procedure. FIG. 2 shows the overall procedures that were used to identify the aptamers for the targeted peptides.

Figure 3:
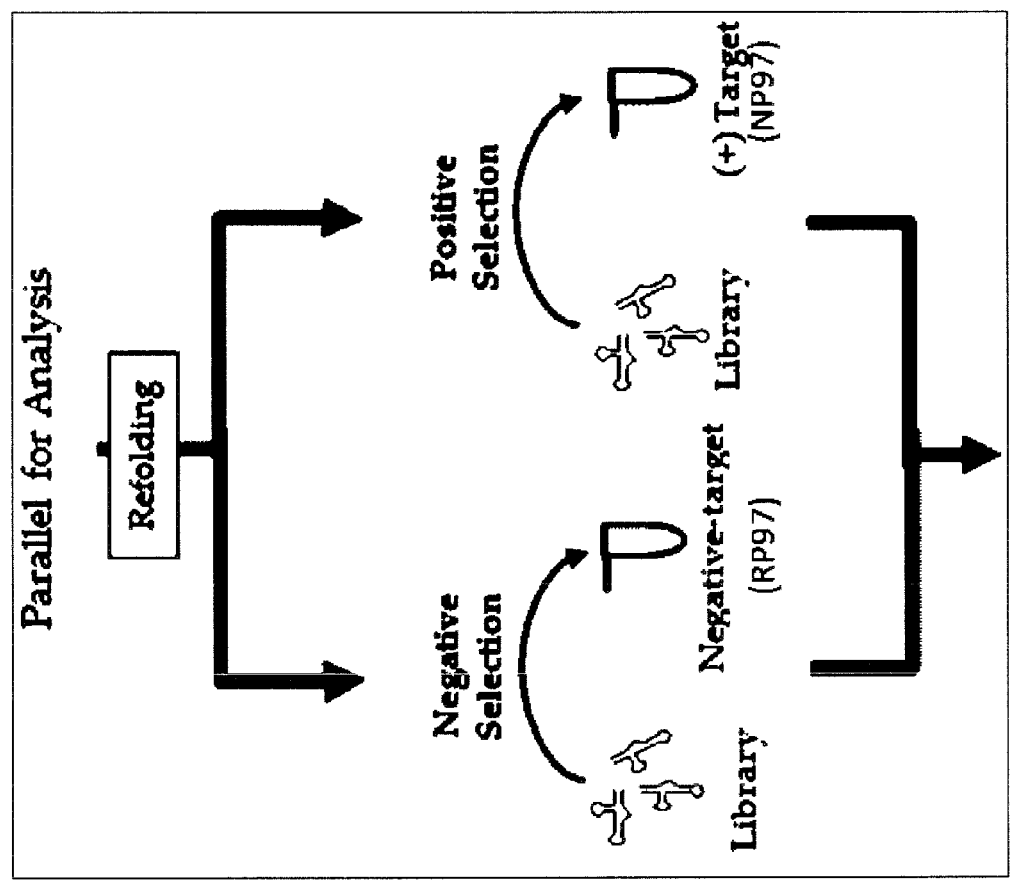
FIG. 3 explains that parallel assessment of the enriched aptamer library

Electrophoretic Mobility Shift Assays (EMSAs) were used to separate portions of the aptamer library that bind to a given target and fail to bind to a counter target in a buffer consisting of 1×DPBS (26.67 mM KCl, 14.71 mM $KH_2PO_4$, 1.38 M NaCl, and 80.60 mM $Na_2HPO_4$-$7H_2O$) with 10 mM $MgCl_2$ (pH 7.4). One round of selection consisted of enriching for unbound, non-shifted DNA material in the presence of the counter target followed by the isolation of bound and shifted DNA after exposure to the target molecule. Each selection round was followed by library amplification through PCR and purification of the DNA Sense strand. After subjecting the initial library of diverse random sequences to three consecutive rounds of selection, the enriched library was divided into two fractions to perform the parallel assessment as shown in FIG. 3.

Figure 4:
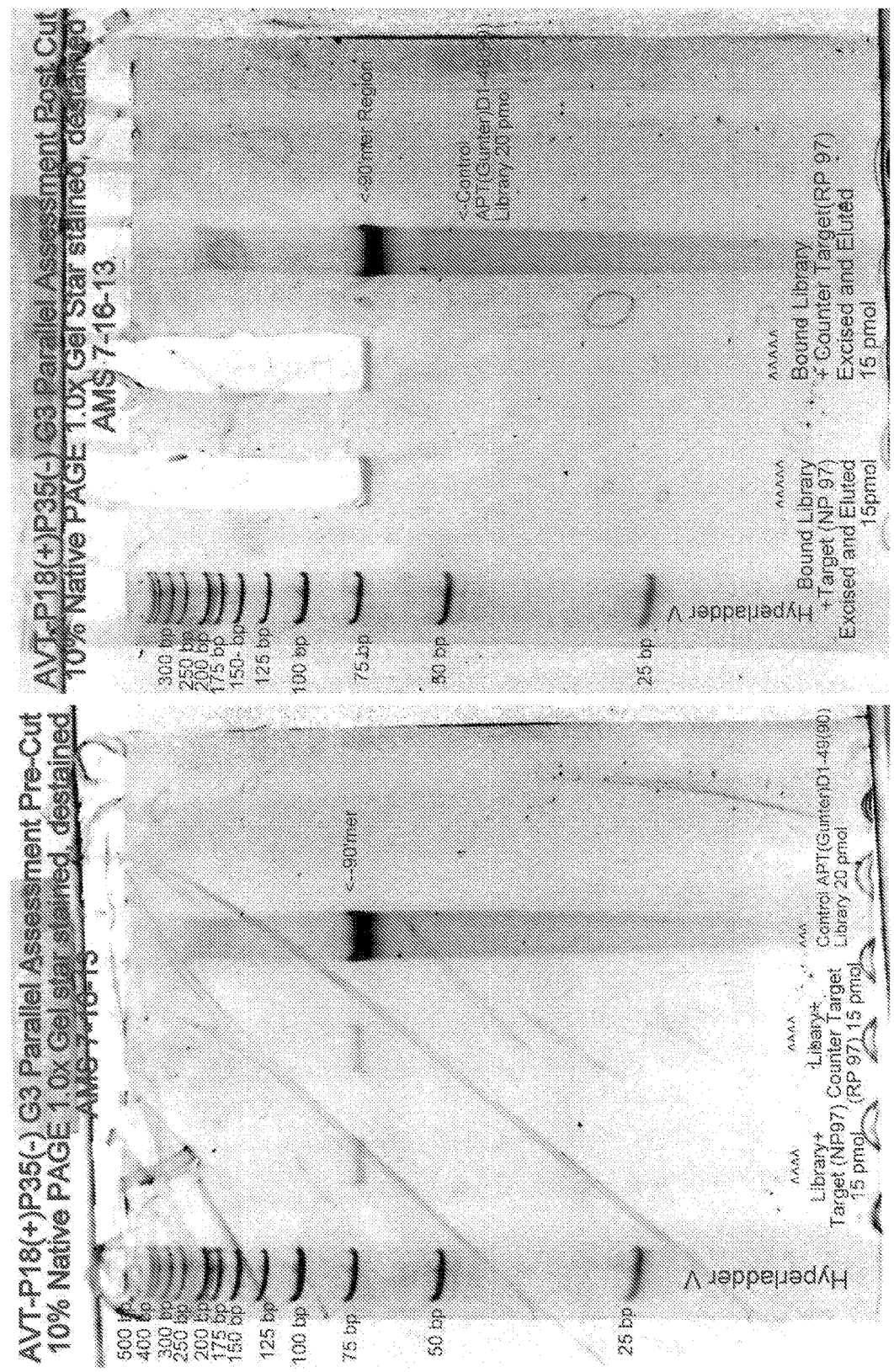
FIG. 4 is one result of the PAGE purification process of bound libraries

After parallel assessment PAGE purifications of bound libraries were performed. 15 pmoles of enriched library was exposed separately to either the target or counter target in selection buffer. After a 60-minute incubation at 37° C., bound DNA material was separated from unbound material using 10% non-denaturing PAGE. Presumably bound material was excised, eluted from the gel, and used as template in PCR amplification in preparation for sequencing. Gel images were taken before and after excision. Hyperladder V (Bioline; Randolph, Mass.) was used as a molecular weight standard. The gels were stained with GelStar Nucleic Acid Stain (Lonza; Walkersville, Md.). Typical results are shown in FIG. 4.

Primary and Secondary Structures of the Aptamers

The initial library containing a large number of random sequences was subjected to three rounds of polyacrylamide gel-based SELEX. The SELEX process is designed to enrich for sequences that bind to the target molecule and eliminate sequences that bind to the counter target molecule over multiple rounds of selection (FIG. 2). As a result, the population to be sequenced is expected to contain multiple copies of potential aptamer candidates; largely homologous sequences representing a library of aptamer candidates[xxxiv]. The selection strategy employed in the present project was designed to identify aptamers that bind to the target peptide, what has been determine to be a region of protein vital for the pathogenicity of the PRRS virus, but fail to bind to a randomized version of that same region. Three rounds of positive and negative selections were conducted. The resultant enriched library was PCR amplified and then divided into two samples, with one exposed to the target in binding buffer and the other exposed to the counter-target (negative-target) in binding buffer (FIG. 3). The parallel assessment is designed to identify DNA molecules that bind indiscriminately to both target and counter target molecules. These promiscuous aptamers are discarded during the bioinformatics analysis portion of the selection project. After partitioning through non-denaturing polyacrylamide gel electrophoresis (non-denaturing PAGE), the regions of gel containing presumably bound material were excised for nucleic acid elution (FIG. 4). DNA collected from the elution was PCR amplified in preparation for sequencing.

Illumina (San Diego, USA)-based technology was implemented to sequence the aptamers after the selections. Subsequent bioinformatics analysis of the sequencing data identified candidate aptamer molecules. Deep sequencing and subsequent data analysis eliminated the traditional approach of performing a large number of selections, which may introduce error and bias due to the screening process. A "good sequence" was assessed as one that contained the full forward and reverse primers (or their complements), as well as a variable region between 44 and 54 nucleotides long to account for minor insertions or deletions of bases. The data was analyzed using proprietary algorithms to identify candidate sequences.

For the aptamer candidate selection the analysis ranked sequences according to a variety of categories, including frequency of homologous sequences, frequency based on motif presence, and presence of multiple motifs. A motif is a smaller segment of bases conserved between sequences, most likely because the segment contributes to the aptamer's binding ability. For the selection of ten candidate sequences to test, the presence of multiple motifs in a sequence was weighted more heavily than the frequency of homologous sequences. However, the relative complexity of a candidate's secondary structure weighed heavily in its ranking. This was primarily determined by the number of stems on the predicted secondary structure (as described below) that are coming-out of the central junction. Thus, while A504 (see FIG. 5.*d*) was determined through the co-occurrence method[xxxv], the fact that there is only 1 stem coming from the central junction makes it one of the less likely candidates. Despite this, there was no large difference in the rankings of the candidates, and they were all worth examining for characterization.

In addition to sequence and motif analysis, secondary structure prediction of the candidate sequences was carried out using the Mfold Web Server[xxxvi]. By inputting the full sequence as well as folding temperature and salt conditions, it is possible to make an informed prediction about what structures an aptamer candidate may take (FIG. 5). The parameters used for the analysis of the selected sequences were matched as closely to selection parameters as possible (e.g. 1.5 M NaCl, 0.01 M $MgCl_2$).

The selected aptamer candidates were then synthesized using phosphoramidite chemistry, and used for affinity binding studies and $K_d$ measurements.

Ten (10) aptamers corresponding to the M-S-S-GP5 polypeptic complex target of the PRRSV LHVA-3 virus (type 2) have been determined. These are:

A501 (CoocSeq1_HistoSeq4, SEQ ID NO: 5):
5'GGGCGACCCTGAAGAGAAAGGTGAGTTTATTGCGGGGGTTATTTATT
GCTTCGAAACGGTGAAAGCCGTAGGTTGCCC-3'

A502 (CoocSeq2_HistoSeq5, SEQ ID NO: 6):
5'GGGCGACCCTGAAGAGTTTTATGATGTGTTGGTTAGTATATGTTATT
CTCCGAAACGGTGAAAGCCGTAGGTTGCCC-3'

A503 (CoocSeq3_HistoSeq5, SEQ ID NO: 7):
5'GGGCGACCCTGAAGAGAGGTGTACATCTAATGCTCGGGTCCTCAGCA
GTGTCGAAACGGTGAAAGCCGTAGGTTGCCC-3'

A504 (CoocSeq4_HistoSeq6, SEQ ID NO: 8):
5'GGGCGACCCTGAAGAGATGTTCGTITTCTATGATATTTCTTGGGATC
GTATCGAAACGGTGAAAGCCGTAGCTTGCCC-3'

A505 (CoocSeq5, SEQ ID NO: 9):
5'GGGCGACCCTGAAGAGTTTGTAATCTGCGATTTTAAAGTTGAGTCGT
CGCGAAACGGTGAAAGCCGTAGGTTGCCC-3'

A506 (CoocSeq6_HistoSeq39, SEQ ID NO: 10):
5'GGGCGACCCTGAAGAGGCGGATGGTGGTTAGTATGCTGCGCCTGTAC
GAAACGGTGAAAGCCGTAGGTTGCCC-3'

A507 (CoocSeq7_HistoSeq14, SEQ ID NO: 11):
5'GGGCGACCCTGAAGAGGTTTGCATATTATAGTTATAGGAGGTGTGTA
ATGGACGAAACGGTGAAAGCCGTAGGTTGCCC-3'

A508 (CoocSeq8, SEQ ID NO: 12):
5'GGGCGACCCTGAAGAGACTGGTGAGTTAATGTTTTTTCTTAGCCTTG
TATCGAAACGGTGAAAGCCGTAGGTTGCCC-3'

A509 (HistoSeq1, SEQ ID NO: 13):
5'GGGCGACCCTGAAGAGATGCGGTGCTTGCCAAGATGGATAGGATAT
GGCTCGAAACGGTGAAAGCCGTAGGTTGCCC-3'

A510 (HistoSeq2, SEQ ID NO: 14):
5'GGGCGACCCTGAAGAGTACATATTGTGAAGATTTCGGCGGGACACC
GTTAACGAAACGGTGAAAGCCGTAGGTTGCCC-3'

Proposed secondary structures of these candidate aptamers are shown in FIG. 5.

Concurrently, ten (10) aptamers corresponding to the M-S-S-GP5 polypeptic complex target of the European PRRSV Lelystad virus (type 1) have been determined. These are:

PEU-499
(SEQ ID NO: 15)
5'GGGCGACCCTGAAGAGTACACACGGGACACACACACACTCACTAGAC
GAAACGGTGAAAGCCGTAGGTTGCCC-3'

PEU-842
(SEQ ID NO: 16)
5'GGGCGACCCTGAAGAGGACCAGAAGCACGGACCACACACAGCGTATCG
AAACGGTGAAAGCCGTAGGTTGCCC-3'

PEU-852
(SEQ ID NO: 17)
5'GGGCGACCCTGAAGAGGACACTGCACGTACACAACGAGGATGAACAC
GAAACGGTGAAAGCCGTAGGTTGCCC-3'

PEU-424
(SEQ ID NO: 18)
5'GGGCGACCCTGAAGAGGATGTTGATAGAGCGCCGACCACACACGCAC
GAAACGGTGAAAGCCGTAGGTTGCCC-3'

PEU-962
(SEQ ID NO: 19)
5'GGGCGACCCTGAAGAGGATAGACAATAGCACACCACGCCCCTGCCACG
AAACGGTGAAAGCCGTAGGTTGCCC-3'

PEU-957
(SEQ ID NO: 20)
5'GGGCGACCCTGAAGAGAACAGGCGCAGTGCAGCACACACCCACACCCG
AAACGGTGAAAGCCGTAGGTTGCCC-3'

PEU-621
(SEQ ID NO: 21)
5'GGGCGACCCTGAAGAGTAACCTGCACACCACGCACGCCATTGTACACG
AAACGGTGAAAGCCGTAGGTTGCCC-3'

PEU-261
(SEQ ID NO: 22)
5'GGGCGACCCTGAAGAGCAGCGTCACCACCCACGCCACCCACAGCCACG
AAACGGTGAAAGCCGTAGGTTGCCC-3'

PEU-002
(SEQ ID NO: 23)
5'GGGCGACCCTGAAGAGTAACGATGAACACAGGACCTCCTCTACACACG
AAACGGTGAAAGCCGTAGGTTGCCC-3'

PEU-001
(SEQ ID NO: 24)
5'GGGCGACCCTGAAGAGTAACGATGAACACAGGACCTCCTCTACACAC
GAAACGGTGAAAGCCGTAGGTTGCCC-3'

Proposed secondary structures of these candidate aptamers are shown in FIG. 6.

Figure 8A:
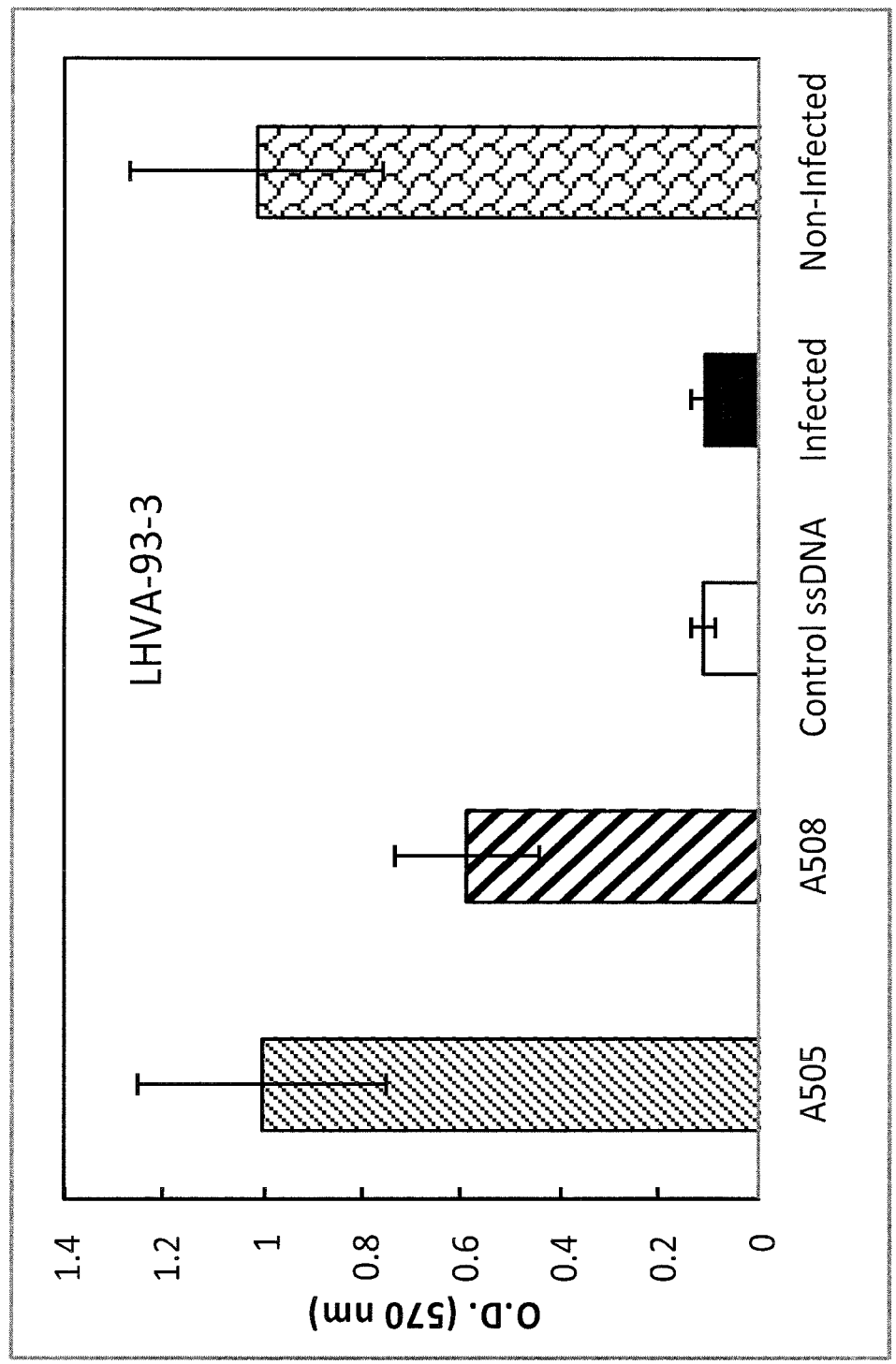
FIGS. 8 a-b are histograms depicting binding levels of PRRSV specific aptamers generated according to the teachings of the present invention (A505 and A508) and control single stranded aptamer to an intact PRRS virus or the $M_{1-16}$-S-S-GP5$_{31-61}$ peptidic complex as determined by ELISA. Note a significant binding of A505 and A508 to the intact virus as compared to control nucleic acid is notable (p=0.042 and v0.0008, respectively), and a significant reduction in A505 binding to the intact virus as compared to the A508 aptamer (p=0.017).
Figure 8B:
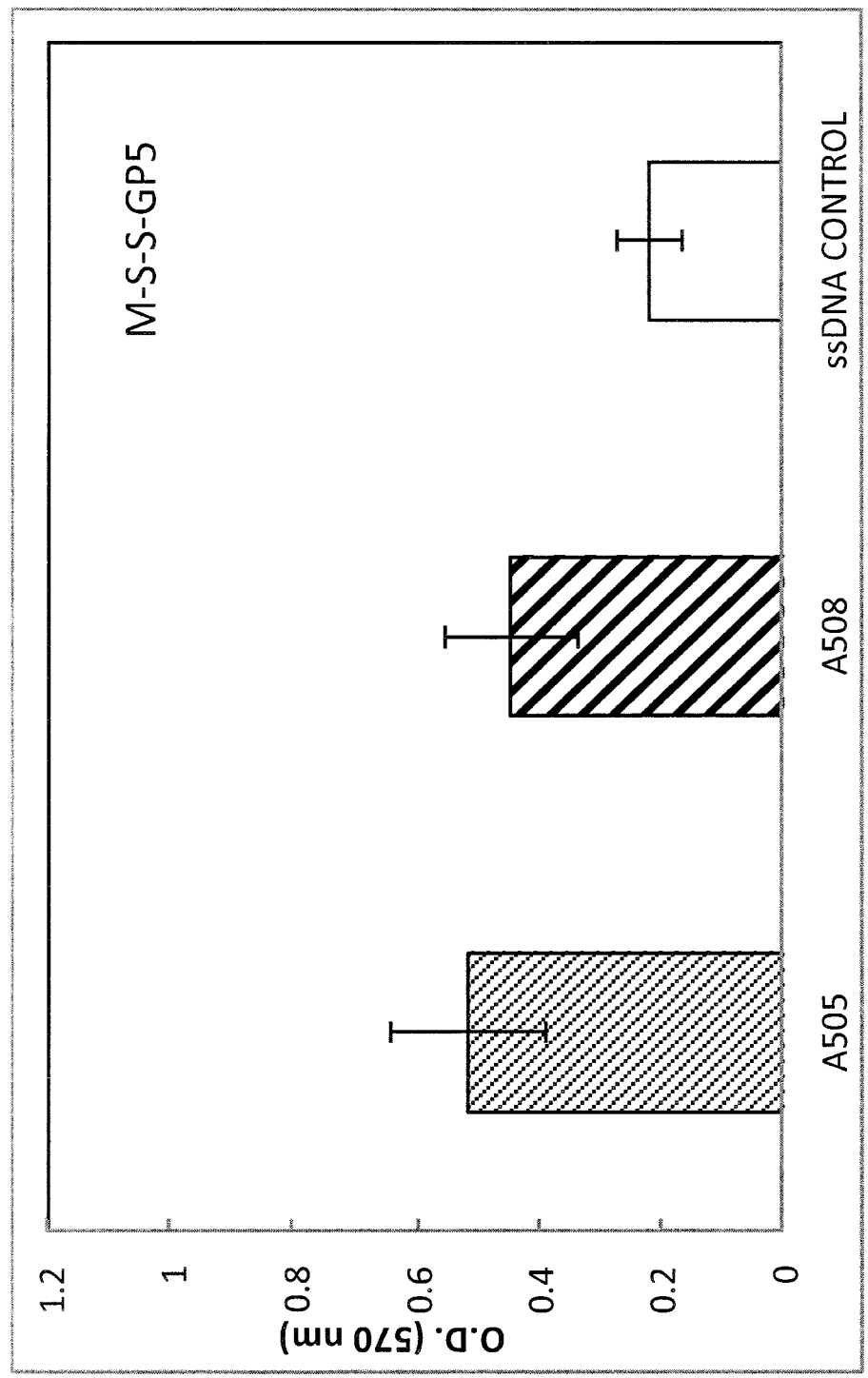

Using various tetrazolium (MTT) colorimetric assay procedures[xxxvi], these aptamers have been "screened" to identify the ones having the highest and fastest binding capabilities for detection and therapeutics purposes for both types of PRRSV. It should be pointed out that the aptamer having the quickest binding efficiency but not necessarily the highest binding strength is the most suitable one for the biosensor. After screening is was found for type 2 PRRSV that the A505, A507, and A508 aptamers have the highest binding capabilities from biosensing and therapeutic perspectives. FIG. 8 illustrates the binding levels of A5050 and A508 unto LHVA-93-3 virus and unto the M-S-S-GP5 peptide. The binding levels of A505 and A508 to the M-S-S-GP5 heterodimer are similar and showed highly significant differences from the control ssDNA (FIG. 8b). On the other hand, there is a significant difference between A505 and A508 in binding to the intact virus, where A505 showed higher binding than A508 (p=0.017), and both showed significant binding compared with the control (FIG. 8.a). For type 1 (Lelystad) is was found that PEU-499, PEU-842, PEU-852, PEU-424, and PEU-962 show good binding capabilities from biosensing and therapeutic perspectives.

While reducing the present invention to practice, the present inventors have uncovered that oligonucleotides (e.g., aptamers) designed to bind conserved sequences in the M-S-S-GP5 polypeptic complex can be utilized to prevent virus binding to host cells. As is illustrated in the examples section that follows, the present inventors have provided aptamer nucleic acid molecules, which can be used to diagnose and treat PRRS virus infection. Such aptamer molecules exhibit viral cross-reactivity and as such can be used as vaccines against the PRRSV.

Assessing the Binding Capabilities of the Selected Aptamers

Thus, according to one aspect of the present invention there is provided a nucleic acid molecule including a polynucleotide sequence that is capable of specifically binding a polypeptic complex participating in the PRRS virus infection of cells.

The ability of the nucleic acid molecules of this aspect of the present invention to specifically bind a polypeptic complex that participates in the PRRS virus infection of cells allows the use thereof in PRRSV infection therapy and diagnostics.

As used herein "a polypeptide which participates in PRRS virus infection of cells" refers to a polypeptide that is encoded by an Arteriviridae virus including type I and II PRRS virus strains, a host cell polypeptide or a peptide fragment thereof.

Examples of PRRS virus polypeptides that participate in virus infection of cells include the European, or type I virus, also known as Lelystad virus (LV), and the American, or type II virus, the RNA-directed RNA polymerase core proteins including GP5 and M proteins.

Examples of host cell polypeptides which participate in PRRS virus infection include but are not limited to heparan sulphate GAG (O-glycosylated proteins), sialoadhesin, CD163 receptors, and aspartic protease cathepsin E.

It will be appreciated that polypeptide targets of this aspect of the present invention are preferably viral, to maximize specificity of the nucleic acid molecules of the present invention and reduce cytotoxicity thereof. Accordingly, preferred polypeptide target sequences include conserved amino acid sequences, which are shared by various strands of PRRS viruses.

Few examples of conserved viral peptide targets for PRRSV are provided in Table 1.

TABLE 1

| Viral peptide targets | Peptide sequence (type 2 PRRSV) | SEQ ID NO | Reference |
| --- | --- | --- | --- |
| GP5 | MLEKCLTAGCCSRLLSLWCIVPFCFAVLANASNDSSS HLQLIYNLTLCELNGTDWLANKFDWAVESFVIFPVLT HIVSYGALTTSHFLDTVALVTVSTAGFVHGRYVLSSIY AVCALAALTCFVIRFAKNCMSWRYACTRYTNFLLDT KGRLYRWRSPVIIEKRGKVEVEGHLIDLKRVVLDGSV ATPITRVSAEQWGRP | 1 | GenBank: AAD12129.1 |
| M | MGSSLDDFCHDSTAPQKVLLAFSITYTPVMIYALKVSR GRLLGLLHLLIFLNCAFTFGYMTFAHFQSTKVALTMG AVVALLWGVYSAIETWKFITSRCRLCLLGRKYILAPA HHVESAARFHPIAANDNHAFVVRRPGSTTVNGTLVPG LKSLVLGGRKAVKQGVVNLVKYAK | 2 | GenBank: AAD12130.1 |

The nucleic acid molecules of this aspect of the present invention refer to single stranded or double stranded DNA or RNA molecules or any modifications thereof, which are capable of specifically binding the polypeptide-targets described hereinabove. The nucleic acid molecules of this aspect of the present invention are interchangeably referred to as "aptamers".

Typically, the nucleic acid molecules according to this aspect of the present invention are of varying length, such as 10-100 bases. It will be appreciated, though, that short nucleic acid molecules (e.g., 10-45 bases) are preferably used for economical, manufacturing and therapeutic considerations, such as bioavailability (i.e., resistance to degradation and increased cellular uptake).

According to presently known embodiments of this aspect of the present invention, the nucleic acid molecules are preferably those set forth in A505, A507, A508 for type 2 PRRSV, and PEU-499, PEU-842, PEU-852, PEU-424, and PEU-962 for type 1 European PRRSV strains.

Modified Nucleic Acid Molecules

As mentioned hereinabove, the nucleic acid molecules of this aspect of the present invention are preferably modified to obtain enhanced bioavailability and improved efficacy to the target polypeptide. Modifications include but are not limited to chemical groups that incorporate additional charge, polarizability, hydrogen bonding, electrostatic interaction and fluxionality to the nucleic acid bases or to the entire molecule. Added or modified chemical groups are selected to include conformationally flexible linkages, which conform to the topology of the polypeptide target. Additionally, measures are taken that the chemistry for the modification of the nucleic acid molecules of this aspect of the present invention allows for either trisphosphate (NTP) or phosphoramidite synthesis.

Thus, for example, nucleic acid molecules of this aspect of the present invention preferably include modifications that allow specific cross-linking to the target polypeptide to thereby form high affinity compounds.

Figure 7A:
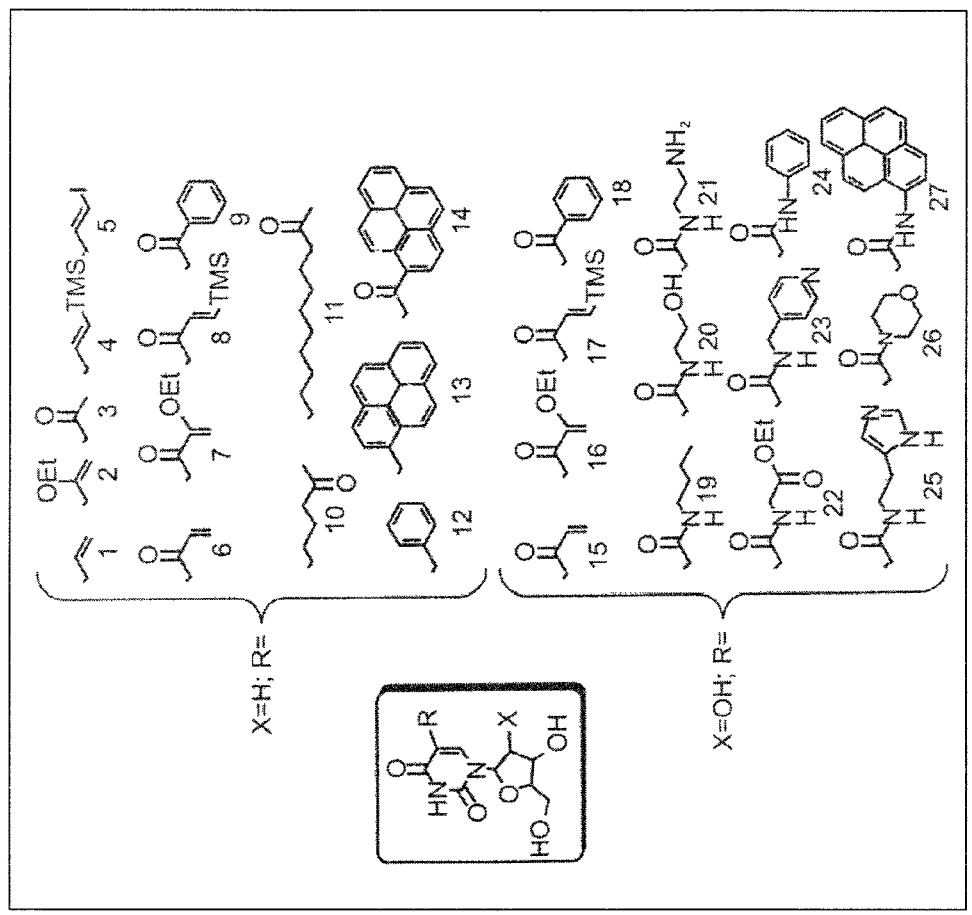
FIG. 7a shows 2'-deoxyuridines and uridines modified at position 5.

Appended cross-linking groups can contain hydrophobic, hydrophilic or charged functionality. Cross-linking may be accomplished by the formation of imine, acetal, ester and disulfide linkages as well as by conjugate addition to α, β-unsaturated carbonyl linkers. Examples of 2'-deoxyuridine nucleosides which are suitable for phosphoramidite synthesis are shown in FIG. 7a including small hydrophobic functional groups such as vinyl (group 1, FIG. 7a), large hydrophobic functional groups such as pyrenyl (groups 13-14, FIG. 7a) and carbonyl compounds with varying degrees of side chain hydrophobicity (groups 3, 6-11, FIG. 7a).

Pyrimidine base modifications, such as RNA uridine nucleoside modifications at position 5, can include hydrophobic groups which can be conjugated in the form of ketones (ex. groups 17, 18 FIG. 7a), amides (groups, 24, 27, FIG. 7a) and the like, which can be attached to either DNA or RNA nucleic acid molecules[xxxvii]. It will be appreciated that amides can impart hydrogen-bonding capabilities to the aptamer. in any case, as described hereinabove, cross-linking carbonyl groups can be attached to the 5-position of uridine (groups 15-18, FIG. 7a). It will be appreciated, though, that the expected reactivity of carbonyl linkers can differ significantly depending on the interface of the target polypeptide.

Figure 7B:
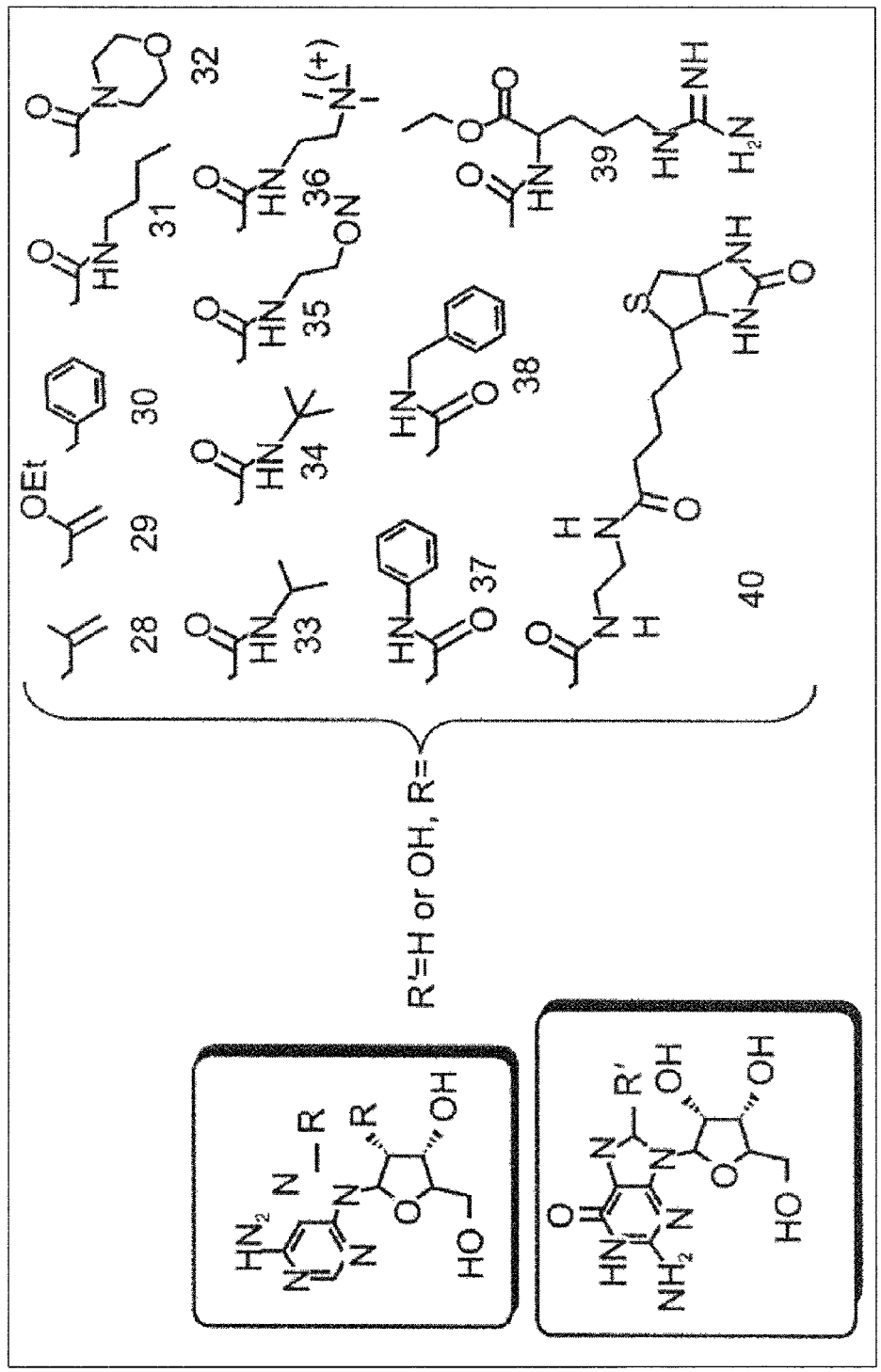
FIG. 7b shows 2'-deoxyadenines, adenines and guanosines modified at position 8.

Examples of purine modifications are shown in FIG. 7b. For example hydrophobic substituents can be attached at the 8-position of RNA or DNA purine nucleosides (groups 28-30, FIG. 7b). The degree of steric hindrance can be varied via amide linkages (groups 31, 33, 34, 37 and 38, FIG. 7b). Hydrophilic (group 35, FIG. 7b) and charged (groups 36 and 39, FIG. 7b) groups may be appended to the 8 position of purine nucleosides. It will be appreciated that functional groups with known affinity to the target polypeptide can be attached to the 8 position of the purine base, such as a biotinylated nucleoside (group 40, FIG. 7b).

Figure 7C:
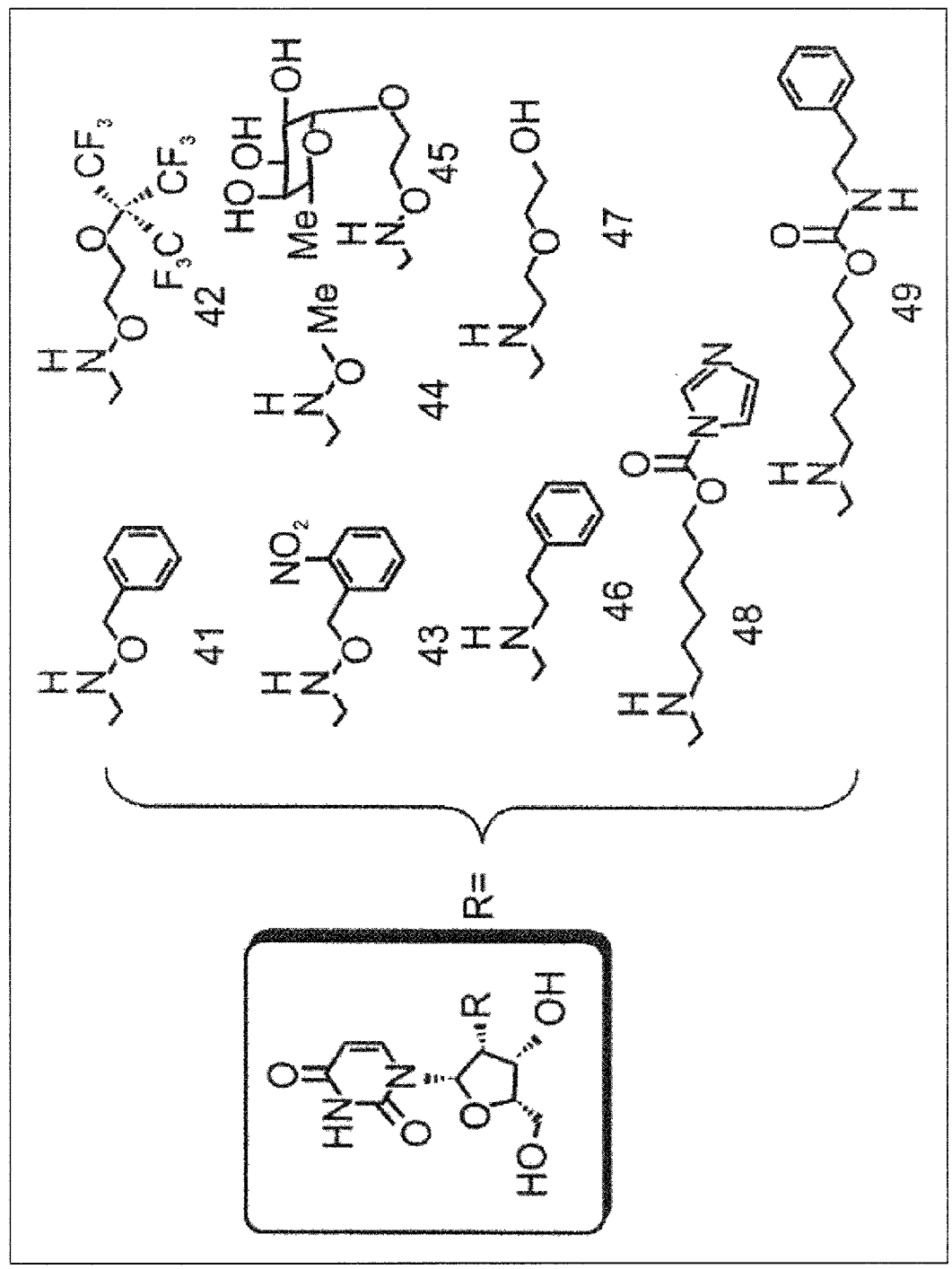
FIG. 7c shows 2'-modified uridines.

Additional sites for modifications include but are not limited to the 2'-position of RNA and the phosphodiester oxygens of RNA and DNA. A 2'-position pyrimidine nucleoside modification can be implemented. Essentially, amine linkers, such as hydroxyl amine linkers can be used to attach hydrophobic groups with different topologies (groups 41-43, 46 and 49, FIG. 7c), hydrophilic groups (45 and 47, FIG. 7c) and groups exhibiting specific affinity to the target polypeptide (group 45, FIG. 7c).

As mentioned hereinabove, the nucleic acid molecules of this aspect of the present invention can also be modified to increase bioavailability thereof. The following illustrates non-limiting examples for such modifications.

The nucleic acid molecules of this aspect of the present invention may comprise heterocyclic nucleosides consisting of purines and the pyrimidines bases, bonded in a 3' to 5' phosphodiester linkage.

Preferably used nucleic acid molecules are those modified in either backbone, internucleoside linkages or bases, as is broadly described hereinunder. Such modifications can oftentimes facilitate oligonucleotide uptake and resistance to intracellular conditions.

Specific examples of nucleic acid molecules useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 687, 808; 4,469,863; 4,476,301; 5,023,243; 5,177,196; 5,188, 897; 5,264,423; 5,276,019; 5,278,302; 5,286,717; 5,321, 131; 5,399,676; 5,405,939; 5,453,496; 5,455,233; 5,466, 677; 5,476,925; 5,519,126; 5,536,821; 5,541,306; 5,550, 111; 5,563,253; 5,571,799; 5,587,361; 5,625,050.

Preferred modified nucleic acid backbones include, for example, phosphorothioates, chiral phosphorothioates, phosphorodithioates, phosphotriesters, amino alkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyiphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439.

Other nucleic acid molecules which can be used according to the present invention, are those modified in both sugar and the internucleoside linkage, i.e., the backbone, of the nucleotide units are replaced with novel groups. The base units are maintained for complementation with the appropriate polynucleotide target. An example for such a nucleic acid sequence mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Nucleic acid molecules of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in the opened literature Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C.[xxxix] and are presently preferred base substitutions, even more particularly when combined with 2'-O-methoxyethyl sugar modifications.

Another modification of the nucleic acid molecules of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-Tritylthiol, a thiocholesterol, an aliphatic chain, e.g., dodecandiol or undecyl residues, a phospholipid, e.g., di-hexadecyl-racglycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety[xi].

It is not necessary for all positions in a given oligonucleotide molecule to be uniformly modified, and in fact more than one of the aforementioned modifications may be incorporated in a single compound or even at a single nucleoside within an oligonucleotide.

Antivirus Effects of Aptamers

As is illustrated in the following examples, the present inventors have conclusively shown that the nucleic acid molecules of the present invention are capable of preventing PRRS virus infection of cells in vitro and in vivo. Furthermore, the ability of the nucleic acid molecules of the present invention to inhibit viral spread following viral challenging, suggests the use of the nucleic acid molecules of the present invention in anti-PRRSV prophylactic and therapeutic applications.

Thus, according to another aspect of the present invention there is provided a method of treating PRRS virus infection.

As used herein the term "treating" refers to preventing PRRS virus infection or substantially reducing (i.e., alleviating or diminishing) symptoms associated with PRRS virus infection.

The method is implemented by providing to a subject in need thereof, a therapeutically effective amount of the nucleic acid molecule of the present invention described hereinabove.

As used herein "a subject in need thereof" refers to a subject suffering from PRRS-virus associated symptoms or at risk of contracting PRRS. Examples of such subjects include but are not limited to piglets aged 6 weeks or less; mature pigs 12 weeks or more, pigs suffering from chronic diseases such as *Mycoplasma* Hyopneumoniae infection, pregnant sows, and pigs in close or frequent contact with anyone at high risk.

Preferably, the nucleic acid molecules of the present invention are provided at a concentration of between, 0.1-150 µg/Kg body weight, preferably 1-100 µg/Kg body weight, more preferably 1-50 µg/Kg body weight and even more preferably 1-15 µg/Kg body weight.

The nucleic acid molecule (i.e., active ingredient) of the present invention can be provided to the subject per se, or as part of a pharmaceutical composition where it is mixed with a pharmaceutically acceptable carrier.

Pharmaceutical Compositions

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. The term "adjuvant" is included under these phrases.

Since activity of aptamers is directly correlated with a molecular weight thereof, measures are taken to conjugate the nucleic acid molecules of the present invention to high molecular weight carriers. Such high molecular weight carriers include, but are not limited to, polyalkylene glycol and polyethylene glycol (PEG), which are biocompatible polymers with a wide range of solubility in both organic and aqueous media[xxxvii].

Alternatively, microparticles such as microcapsules or cationic lipids can serve as the pharmaceutically acceptable carriers of this aspect of the present invention. As used herein, microparticles include liposomes, virosomes, microspheres and microcapsules formed of synthetic and/or natural polymers[xlii]. Methods for making microcapsules and microspheres are known to the skilled in the art and include solvent evaporation, solvent casting, spray drying and solvent extension. Examples of useful polymers that can be incorporated into various microparticles include polysaccharides, polyanhydrides, polyorthoesters, polyhydroxides and proteins and peptides.

Liposomes can be generated by methods well known in the art[xlii]. Alternatively, the nucleic acid molecules of this aspect of the present invention can be incorporated within microparticles, or bound to the outside of the microparticles, either ionically or covalently Cationic liposomes or microcapsules are microparticles that are particularly useful for delivering negatively charged compounds such as the nucleic acid molecules of this aspect of the present invention, which can bind ionically to the positively charged outer surface of these liposomes. Various cationic liposomes are known to be very effective at delivering nucleic acids or nucleic acid-protein complexes to cells both in vitro and in vivo, as reported[xliii].

Cationic liposomes or microcapsules can be generated using mixtures including one or more lipids containing a cationic side group in a sufficient quantity such that the liposomes or microcapsules formed from the mixture possess a net positive charge which will ionically bind negatively charged compounds. Examples of positively charged lipids which may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium (DOTMA).

As mentioned hereinabove the pharmaceutical compositions of this aspect of the present invention may further include excipients. The term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Various techniques for formulation and administration of drugs may be found in the opened literature[xliv]. Suitable routes of administration may, for example, include oral, transmucosal, especially transnasal, parenteral delivery, including intramuscular, subcutaneous and intramedullary injections as well as intranasal, or intraocular injections. Alternately, one may administer a preparation in a local rather than systemic manner, for example, via injection of the preparation directly into the chest of the swine.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. The "proper" formulation is dependent upon the route of administration chosen.

For injection, the active ingredients of the invention may be foi mlated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can also be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses. Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., carbon dioxide, or dichlorodifluoromethane, trichlorofluoromethane, or dichloro-tetrafluoroethane. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents that increase the solubility of the active ingredients to allow for the preparation of highly concentrated solutions.

Alternatively, the active ingredient may be in powder form for constitution with a suitable vehicle, e.g., sterile, pyrogen-free water based solution, before use[xiv].

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art. For any preparation used in the methods of the invention, the therapeutically effective amount or dose can be estimated initially from in vitro assays. For example, a dose can be formlated in animal models and such information can be used to more accurately determine useful doses in herds.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in herds. The dosage may vary depending upon the dosage form employed and the route of administration utilized.

Depending on the severity and responsiveness of the condition to be treated, dosing can be of a single or a plurality of administrations, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing veterinarian, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be a labeling approved by the U.S. Food and Drug Administration for veterinary prescription drugs or of an approved product insert.

Detection of PRRSV

According to yet another aspect of the present invention there is provided a method of identifying PRRS virus in a biological sample.

As used herein a biological sample refers to any body sample such as blood, pleural fluid, respiratory fluids and nasal aspirates. Methods of obtaining body fluids from vertebrates are well known in the art.

The method is implemented by contacting the biological sample with a nucleic acid molecule according to the invention.

The nucleic acid molecules of the present invention can be attached to a solid substrate, such as described herein below.

Contacting is carried-out under conditions that allow the formation of a polypeptide-nucleic acid molecule duplex. Duplexes are preferably washed to remove any non-specifically bound polypeptides allowing only those nucleic acid molecules specifically bound within the complexes to be detected.

Polypeptide-bound nucleic acid molecules in the biological sample are detected to thereby identify the PRRS infection.

In general monitoring of polypeptide-nucleic acid molecule complexes is well known in the art and may be carried-out as described hereinabove. These approaches are generally based on the detection of a label or marker, such as described herein below. Preferably, detection of an infected sample is effected by comparison to a normal sample, which is not infected with the PRRS virus.

Generation of Nucleic Acid Molecules

To generate the nucleic acid molecules of the present invention, a robust selection approach is preferably employed.

Thus, according to an additional aspect of the present invention there is provided a method of generating a nucleic acid molecule, which is capable of specifically binding a polypeptidic complex participating in the PRRS virus infection of cells, thereby inhibiting PRRS virus infection of cells.

The method is implemented as follows. First, a plurality of nucleic acid molecules are contacted with a polypeptide target, which participates in PRRS virus infection of cells as described hereinabove. Following duplex formation (i.e., a non-Watson Crick complementation between the polypeptide target and the nucleic acid molecules), at least one nucleic acid molecule of the plurality of nucleic acid molecules that is capable of specifically binding the polypeptide is identified. Finally, polypeptide bound nucleic acid molecules are isolated to thereby generate the molecule that is capable of inhibiting PRRS virus infection.

Single-stranded DNA molecules can be generated from a library of oligonucleotide sequences including a randomized polynucleotide sequence flanked by two defined nucleotide sequences that can be used for polymerase chain reaction (PCR) primer binding. The library is amplified to yield double-stranded PCR products. The randomized sequences can be completely randomized (i.e., the probability of finding a base at any position being 1:4) or partially randomized (i.e., the probability of finding a base at any position is selected at any level between 0-100%).

For preparation of single stranded aptamers, the downstream primer is biotinylated at the 5' end and PCR products are applied to an avidin agarose column. Single stranded DNA sequences are recovered by elution with a weakly basic buffer. Single stranded RNA molecules can be generated from an oligonucleotide sequence library, which is amplified to yield double-stranded PCR products containing a T7 bacteriophage polymerase promoter site. RNA molecules can then be produced by in vitro transcription using T7 RNA polymerase.

The nucleic acid molecules of this aspect of the present invention can be generated from naturally-occurring nucleic acids or fragments thereof, chemically synthesized nucleic acids, enzymatically synthesized nucleic acids or nucleic acid molecules made by a combination of the foregoing techniques The library of this aspect of the present invention is generated sufficiently large to provide structural and chemical coverage of selected nucleic acid modifications described hereinabove.

Typically, a randomized nucleic acid sequence library according to this aspect of the present invention includes at least $10^{16}$ sequence variants.

Nucleic acid modifications can be effected prior to incubation with the target polypeptide. In this case, although screening is implemented on the final modified aptamer, modification is restricted not to interfere with any process, such as an enzymatic process (e.g., transcription), which takes place during the screening.

Alternatively, a nucleic acid molecule can be modified following selection (i.e., isolation of a polypeptide bound nucleic acid molecule). Thus, a wide range of functional groups can be used simultaneously. In this case, electrospray ionization mass spectrometry (ESI-MS) can be used to elucidate the right functional group.

In any case, once nucleic acid molecules are obtained they are contacted with the polypeptide target, as mentioned hereinabove.

Incubation of the nucleic acid molecules with the target polypeptide of this aspect of the present invention is preferably implemented under physiological conditions. As used herein the phrase "physiological conditions" refers to salt concentration and ionic strength in an aqueous solution, which characterize fluids found in the metabolism of vertebrate animal subjects which can be infected with PRRS virus, also referred to as physiological buffer or physiological saline. For example physiological fluids of swine are represented by an intracellular pH of 7.1 and salt concentrations (in mM) of sodium 3-15; potassium 140; magnesium 6.3; Calcium 10-4; Chloride 3-15, and an extracellular pH of 7.4 and salt concentrations (in mM) of sodium 145; potassium 3; Magnesium 1-2; Calcium 1-2; and Chloride 110.

The nucleic acid molecules can be incubated with the target polypeptide either in solution or when bound to a solid substrate.

It will be appreciated that some of the above-described base modifications can be used as intermediates for attaching the nucleic acid molecule to a solid substrate. For example, the modified uridine shown in group 48 of FIG. 7c, can serve as a common intermediate which may be further modified by substitution of the imidazole with a wide variety of hydrophobic, hydrophilic, charged and cross linking groups, prior to activation as the phosphoramidite reagent used in solid phase synthesis Methods for attaching nucleic acid molecules to solid substrates are known in the art including but not limited to glass printing, photolithographic techniques, inkjet printing, masking and the like.

Typically, a control sample is included to select against nucleic acid molecules that bind to non-target substances such as the solid support and/or non-target peptides/proteins.

Separation of unbound nucleic acid sequences and identification of bound nucleic acid sequences can be effected using methods well known in the art. Examples include, but are not limited to, selective elution, filtration, electrophoresis and the like.

Alternatively, imaging can identify bound aptameric molecules. For example, optical microscopy using bright field, cpifluorescence or confocal methods, or scanning probe microscopy can be used to identify a polypeptide bound nucleic acid molecule. To facilitate visualization, nucleic acid molecules or polypeptides are preferably labeled using any radioactive, fluorescent, biological or enzymatic tags or labels of standard use in the art.

The following illustrates a number of labeling methods suitable for use in the present invention. For example, nucleic acid molecules of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, fluorescent moieties are used, including but not limited to fluorescein, lissarine, phycoerythrin, rhodamine, Cy2, Cy3, Cy3.5, Cy5, Cy5.5, Cy7, FluorX and others.

It will be appreciated that the intensity of signal produced in any of the detection methods described hereinabove may be analyzed manually or using a software application and hardware suited for such purposes.

Isolation of an aptamer sequence (i.e., polypeptide-bounding nucleic acid) typically involves sequence amplification such as by PCR. Amplification may be conducted prior to, concomitant with or following separation from the target polypeptide. The PCR method is well known in the art[xlvi]. It will be appreciated that if RNA molecules are used, the amplified DNA sequences are transcribed into RNA.

Other methods of amplification may be employed including standard cloning, ligase chain reaction and the like [L. M. Khachigian. DNAzymes: cutting a path to a new class of therapeutics. Curr. Opin. Mol. Ther., 2002, vol. 4, pp. 119-121]. For example, once an aptamer is identified, linkers may be attached to each side to facilitate cloning into standard vectors. Single stranded or double stranded aptamers, may be cloned and recovered.

The recovered nucleic acid molecule, in the original single-stranded or duplex form, can then be used for iterative rounds of selection and amplification (i.e., target polypeptide binding). Typically, following three to six rounds of selection/amplification, nucleic acid molecules that bind with a preferred affinity of nM to M range can be obtained.

It will be appreciated that methods for identifying nucleic acid molecules capable of specifically binding polypeptide targets are known in the art. For example, U.S. Pat. No. 5,270,163 discloses the SELEX method for the identification of nucleic acid ligands as follows. A candidate mixture of single-stranded nucleic acids having regions of randomized sequence is contacted with a target compound and those nucleic acids having an increased affinity to the target are partitioned from the remainder of the candidate mixture. The partitioned nucleic acids are amplified to yield a ligand-enriched mixture. The target-oligonucleotide complexes are then separated from the support and the uncomplexed oligonucleotides, and the complexed oligonucleotides are recovered and subsequently amplified using PCR. The recovered oligonucleotides may be sequenced and subjected to successive rounds of selection using complexation, separation, amplification and recovery.

Alternatively, the nucleic acid sequences of the present invention can be generated by rational drug design. Rational drug design is the inventive process of finding new medications based on the knowledge of a biological target[xlvii]. The drug is most commonly an organic small molecule that activates or inhibits the function of a biomolecule such as a protein, which in turn results in a therapeutic benefit. Thus, rational drug design is a potent means of identifying small molecules that are complementary in shape and charge to the biomolecular target with which they interact and therefore will bind to it.

Drug design frequently but not necessarily relies on computer modeling techniques. This type of modeling is often referred to as computer-aided drug design. Finally, drug design that relies on the knowledge of the three-dimensional structure of the biomolecular target is known as structure-based drug design. To identify a putative aptamer sequence via rational drug design by screening a nucleic acid sequence structure database ("3D database"), software employing "scanner" type algorithms employ atomic coordinates defining the three-dimensional structure of a binding pocket of a molecule or molecular complex, such as the M-S-S-GP5 binding pocket of the PRRS virus, and of a nucleic acid sequence structure stored in the database to computationally model the "docking" of the screened aptamer structure with the binding pocket so as to qualify the binding of the binding pocket with the aptamer structure. Iterating this process with each of a plurality of putative aptamer structures stored in the database therefore enables computational screening of such a plurality to identify a chemical structure potentially having a desired binding interaction with the binding pocket, and hence the putative inhibitor.

Examples of nucleic acid structure database for identifying the nucleic acid molecule of the present invention include the nuclei acid database/NDB (http://ndbserver.rutgers.edu).

Alternatively, a refined aptamer sequence can be elucidated by modifying a known aptamer structure (e.g. A505 (CooqSeq5)) using a software comprising "builder" type algorithms which utilizes a set of atomic coordinates defining a three dimensional structure of the binding pocket and the three-dimensional structures of the basic aptamcr to computationally assemble a refined aptamer. Ample guidance for performing rational drug design via software employing such "scanner" and "builder" type algorithms is available in the literature of the art[xlviii].

Criteria employed by software programs used in rational drug design to qualify the binding of screened aptamer structures with binding pockets include gap space, hydrogen bonding, electrostatic interactions, van der Waals forces, hydrophilicity/hydrophobicity, etc[xlix]. Generally, the greater the contact area between the screened molecule and the polypeptide binding region, the lower the steric hindrance, the lower the "gap space", the greater the number of hydrogen bonds, and the greater the sum total of the van der Waals forces between the screened molecule and the polypeptide binding region of, the greater will be the capacity of the screened molecule to bind with the target polypeptide. The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked molecule, with a user-defined grid spacing, and represents volume that could advantageously be occupied by a modifying the docked aptamer positioned within the binding region of the polypeptide target. Contact area between compounds may be directly calculated from the coordinates of the compounds in docked conformation using various commercially available Molecular Structure (MS) software packages.

In any case, once putative aptamer sequences are identified they are examined for specific binding to the target polypeptide, which can be implemented using a number of biochemical methods known in the art[*l*].

Alternatively or additionally, the nucleic acid sequences of the present invention are tested for inhibiting PRRS virus infection in vitro such as in PAMs or MARC-145 cultured cell line, or in vivo as further described in Example 2 (in vitro) and Example 3 (in vivo) of the Examples section.

The Polypeptide Target

As described hereinabove, an important constituent in aptamer design is selection of the polypeptide target. It is appreciated that peptides used for selecting the aptamer molecules of the present invention can be used as potent tools in PRRS related therapeutic and diagnostic applications. Thus, according to yet an additional aspect of the present invention there is provided a polypeptide useful for vaccination against a PRRS virus (i.e. Arteriviridae).

Preferably, the polypeptide of the present invention includes a complex amino acid sequence defined by amino acid coordinates $M_{1-173}$-S-S-$GP5_{1-128}$ that encompass the globular region of the PRRS which mediates binding to host cell determinants such as the sialoadhesin receptors.

More preferably the polypeptide of the present invention includes an amino acid sequence defined by amino acid coordinates $M_{1-174}$-S-S-$GP5_{1-108}$ that encompass a further minimal region of the PRRSV.

Since the receptor binding pocket of the PRRS polypeptide is mostly unexposed to the immune system due to conformational restrictions, the polypeptide of this aspect of the present invention, preferably further includes additional antigenic epitopes such as defined by amino acid coordinates $M_{1-16}$-S-S-$GP5_{31-61}$.

It will be appreciated that other antigenic surface proteins (GP3, GP4, etc), that are preferably conserved can be included in the polypeptide of the present invention.

The term "polypeptide" as used herein encompasses native peptides (either degradation products, synthetically synthesized peptides or recombinant peptides) and peptidomimetics (typically, synthetically synthesized peptides), as well as as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification.

Methods for preparing peptidomimetic compounds are well known in the art[*li*]. Further details in this respect are provided hereinunder.

Peptide bonds (—CO—NH—) within the peptide may be substituted, for example, by N-methylated bonds (—N(CH$_3$)—CO—), ester bonds (—C(R)H—C—O-O—C(R)—N—), ketomethylen bonds (—CO—$CH_2$), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition, the peptides of the present invention may also include one or more modified amino acids or one or more non-amino acid monomers (e.g. fatty acids, complex carbohydrates etc.).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the present invention are preferably utilized in a linear form, although it will be appreciated that in cases where "cyclization" does not severely interfere with peptide characteristics, cyclic forms of the peptide can also be utilized. The present inventors have conclusively shown that polypeptides generated according to the teachings of the present invention are capable of triggering a partial cellular immune responses (this was also demonstrated by several authors that show that GPS, GP4, GP3, and M can trigger an immune response.

Treating of Subjects Infected with PRRSV

As mentioned hereinabove, the polypeptides and nucleic acid sequences of the present invention can be used for treating PRRSV infection.

Thus according to yet a further aspect of the present invention there is provided a method of treating PRRS virus infection.

The method is implemented by providing to a subject in need thereof, a therapeutically effective amount of the polynucleotide of the present invention, described hereinabove.

Preferred administration routes and pharmaceutical compositions are described hereinabove.

It will be appreciated that immunocomplex (virus+aptamers) generated according to the teachings of the present invention can be used also for identifying PRRS virus in a biological sample.

Preferably, immunocomplexes are washed prior to detection to remove any non-specifically bound viruses, allowing only those viruses specifically bound within the primary immune complexes to be detected.

In general detection of immunocomplex formation is well known in the art and may be achieved by any one of several approaches. These approaches are generally based on the detection of a label or marker, such as described hereinabove.

The nucleic acid molecules, conjugates thereof, polynucleotides, polypeptides and antibodies generated according to the teachings of the present invention can be included in a biodetection device or a diagnostic kit or therapeutic kit. These reagents can be packaged in one or more containers with appropriate buffers and preservatives and used for diagnosis or for directing therapeutic treatment.

Thus, nucleic acid molecules and conjugates thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The nucleic acid molecules and conjugates thereof of such kits can also be attached to a solid support, as described and used for diagnostic purposes.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature[lii]. The procedures therein are believed to be well known in the art and are provided for the convenience of the reader. All the information contained therein is incorporated herein by reference.

Example 1 the Peptidic M-S-S-GP5 Complex Specific Aptamers Rationale and Design

Systematic Evolution of Ligands by Exponential Enrichment (SELEX) was implemented in order to identify aptamer oligonucleotides that bind the PRRS virus.
Materials and Experimental Procedures
Library Generation—
The aptamer library containing a central randomized sequence of 30 nucleotides flanked by a common 5' sequence (i.e. 5'-GGGCGACCCTGAAGAG-) denoted as T3 (SEQ ID NO: 25), and a common 3' sequence (i.e. -CGAAACGGTGAAAGCCGTAGGTTGCCC-3') (SEQ ID NO: 26), was synthesized in a 380B DNA synthesizer. The library included a 30 nucleotides random segment, over all $10^{16}$ molecules and generated according to manufacturer's instructions.
SELEX—
ssDNA aptamers were denatured at 80° C. for 10 min and then cooled on ice for 10 min. Aptamers (30 nmole) were mixed with 25 µg of M-S-S-GP5 peptidic complex (further described in Example 6 below) in 500 µl selection buffer (50 mM Tris-HCl; pH 7.4, 5 mM KCl, 100 mM NaCl, 1 mM MgCl2 tRNA, 0.2% BSA) at 37° C. for 30 min. Aptamer-peptide complex was purified by adding the 25 µl Ni-NTA superflow and amplified by PCR using primers directed to the common T3 sequences in the aptamer library, and 3'-primer (i.e. -CGAAACGGT-GAAAGCCGTAGGTTGCCC-3'). SELEX was repeated 3 times, following which amplified nucleotides were transformed into E. coli. PCR conditions for SELEX included 5 min 95° C./1 min 95° C./1 min 55° C./1 min 72° C./10 min 72° C. and 100 pmole of each primer.

Reverse Screening of Aptamer—
Selected ssDNA molecules from each individual clone were biotinylated using the B-T3 which is same sequence with 5' primer (T3 primer), and Klenow fragment (2 unit/ml). To prepare single stranded biotin conjugated CoocSeq5 aptamer for the reverse screening, T3 Primer was Biotin labelled. A 96-well flat bottom ELISA plate was prepared by coating each well with 100 µl of streptavidin (100 µg/ml) diluted in 0.1 M NaHCO$_3$ following by a 37° C. overnight incubation. Following several washings with PBS, wells were blocked with 200 µl of PBS containing 1% BSA for 2 hours at room temperature and subsequent washing three times with PBS-T (10 mM PBS containing 0.05% (v/v) Tween-20). Thereafter, 100 µl of 2.5 pmole/100 µl biotinylated-ssDNA were added to the wells and incubated at 37° C. for 2 hours followed by washing four times with PBS-T. T3 primer was used as negative control. Following washing, 100 µl of fluid containing 2 µg histidine labelled M-S-S-GP5 peptidic complex were added to the indicated wells and incubated at 37° C. for 2 hours. The wells were then washed for 4 times with PBS-T. The reverse screening assay was completed by ELISA.

Enzyme-Linked Immunosorbent Assay (ELISA)—
High binding capacity ELISA plates (Immunoplate, Nunc) were coated with 100 µl allantoic fluid containing 500 TCID$_{50}$ of various PRRS virus strains diluted in phosphate buffered saline (PBS) by incubating at 4° C. overnight. Following several washing steps with PBS, wells were blocked with 200 µl of PBS containing 1% bovine serum albumin (BSA) and incubated for 90 min at room temperature. Plates were then washed three times with PBS containing 0.05% (v/v) Tween-20 (PBS-T). Each well was then supplemented with 100 µl serial diluted serum samples and incubated at 37° C. for 2 hours. Following this incubation period, plates were washed five times in PBS-T and bound antibodies were detected using horseradish peroxidase labelled goat anti-mouse IgG conjugates (HRP). Immunocomplexes were visualized by incubating with 3,3',5,5'-Tetramethyl benzidine solution (TMB) for 30 min at room temperature. Reaction was terminated with 50 µl of 2M H$_2$SO$_4$, plates were read with a multichannel spectrophotometer at 570 nm.

Results—
As explained hereinabove, in order to identify oligonucleotides that bind to the peptidic complex M-S-S-GP5, a nucleotide library containing random 30 nucleotides between conserved linkers, was synthesized. The library included $10^{16}$ types of different ssDNA, which were hybridized to the M-S-S-GP5 peptidic complex and purified by Ni-NTA resin. Following purification, ssDNAs were amplified by PCR using the linker sequences. The process was 4 times repeated, and re-screening of the M-S-S-GP5 complex was implemented by ELISA. The reverse-screening processes resulted in three oligonucleotide aptamers, denoted as A505, A507, and A508 for type 2 PRRSV, and in five oligonucleotide aptamers, denoted PEU-499, PEU-842, PEU-852, PEU-424, and PEU-962 for type 1 PRRSV. All these aptamers showed binding capacity to the M-S-S-GP5 complex of either type 1 or type 2 PRRSV. However a significant difference in binding the intact virus was evident (FIGS. 8 a-b). Therefore, structural and functional analysis of the A505 and A508 oligonucleotides only was further implemented for type 2 PRRSV, while all five selected aptamers were retained for type 1 PRRSV. Proposed secondary structures using DNAdraw program for A505 and A508, as well as a control oligonucleotide are shown in FIGS. 5e-5h.

Example 2 In-Vitro Aptamer Protection from PRRSV Infection

The protective effect of the A505 aptamer against PRRSV infection (the LHVA-93-3 virulent strain) was investigated in vitro using PAMs and MARC-145 cells.

Materials and Experimental Procedures

Viruses—

The LHVA-93-3, VR-2332, and NVSL 97-7895 strains were grown by seeding PAMs cells or MARC-145 cells. Virus growth, purification, and titration were performed according to standard methods described in the OIE Terrestrial Manual—May 2015, Chapter 2.8.7—Porcine Reproductive and Respiratory Syndrome, section 1.1.3 (see http://www.oie.int/fileadmin/Home/eng/Health_standards/tahm/2.08.07_PRRS.pdf).

Cells—

PAMs or MARC-145 cells (MARC-145, ATCC #CCL 34) were maintained in Dulbecco's modified Eagle's medium (DMEM) supplemented with heat inactivated 10% fetal calf serum (FCS). PAM were also produced[liii] and used for the aptaneutralization (MTT) tests.

MTT Assay—

PAMs or MARC-145 cells were plated in 96 well plates ($7 \times 10^4$/well) one day prior to the assay. Cells were washed twice with Dulbecco's phosphate buffered saline (DPBS) prior to an one (1) hour incubation with Hank's balanced salt solution (HBSS) supplemented with 25 mM HEPES and 4 mM sodium bicarbonate (pH 7.3) including 500TCID$_{50}$ of LHVA-3 or 500TCID$_{50}$ of NVSL in the presence or absence of the indicated aptamer concentration. Following infection, cells were incubated in growth medium at 37° C. for 72 hours. MTT assay was performed by adding 4 mg/ml MTT (3-[4,5-Dimethylthiazol-2-yl]-2,5-diphenyltetrazolium bromide dissolved in PBS to the cell cultures and incubation at 37° C. for 3 hours. Plates were then centrifuged at 800×g for 10 min. Supernatants were aspirated and the formazan dye was dissolved in 150 µl/well of isopropyl alcohol, and O.D. values were determined with an ELISA reader at 570 nm.

In Vitro Viral Protection Prior to Viral Infection PAMs or MARC-145 cells were plated on 96 well plates ($7 \times 10^4$/well) 24 hours prior to the experiment. Each well was washed twice with DPBS prior to treating the cells with various amounts of A505 (12.5 to 2000 pmole) at 37° C. for the indicated time points. Cells were then washed twice with DPBS and infected with 500 TCID$_{50}$ LHVA-3 (or NVSL or VR-2332 or Lelystad) for 1 hour in enriched HBSS. Following incubation, cells were transferred to growth medium and incubated at 37° C. for 72 hours. Thereafter an MTT assay was implemented as described.

In Vitro Viral Protection Following Viral Infection— PAMs or MARC-145 cells were plated on 96 well plates ($7 \times 10^4$/well) 24 hours prior to viral infection. Viral infection was effected as described above. Infected cells were gently washed with DPBS for 3 times. Cells were then treated with various amounts of A505 (12.5 to 2000 pmole) for 1 hour at 37° C. Following incubation, cells were transferred to growth medium and incubated at 37° C. for 72 hours. Thereafter an MTT assay was implemented as described.

Immunostaining—

$5 \times 10^5$ PAMs or MARC-145 cells were laid on glass cover slips. Following 24 hr, LHVA-93-3 PRRS virus was added with or without 1 hr pre-incubation with A505. Following another 48 hrs, cells were permeabilized with 3% paraformaldehyde containing 0.5% Triton X-100 and subsequently fixed with freshly prepared 3% paraformaldehyde. Influenza surface antigen hemagglutinin was detected by incubating the cultures with a swine monoclonal antibody specific for PRRSV (diluted 1:100). All antibody incubations were effected for 1 hr at room temperature in a humidified chamber, followed by three washes in PBS. Primary antibodies were detected with Cy3 conjugated goat anti-swine immunoglobulin secondary antibodies. Nuclei were visualized by staining with 2 µg/ml 4',6-diamidino-2-phenylindole (DAPI). Immunofluorescence microscopy was performed using a Nikon Eclipse E600 microscope.

Results—

Figure 9A:
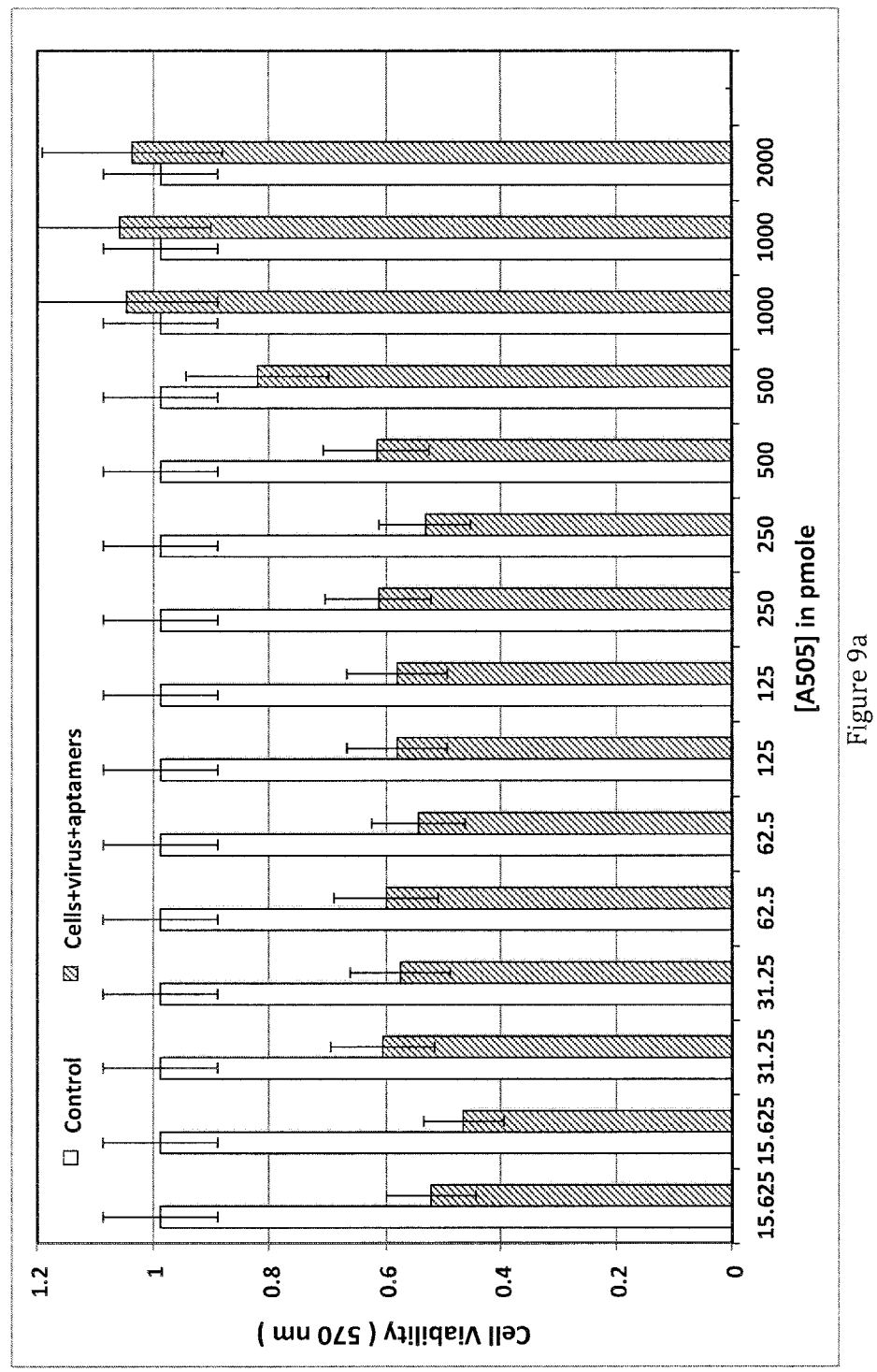
FIG. 9a is a dose response curve showing the effect of A505 aptamer of the present invention on viability of PRRS virus treated PAMs or MARC-185 cells as determined using the 3-(4,5-dimethylthiazol-2-yl)-2,5-diphenyltetrazolium bromide (MTT) assay. Note the highest protective effect was achieved using A505 at the concentration range of 1000 to 2000 pmole.
Figure 9B:
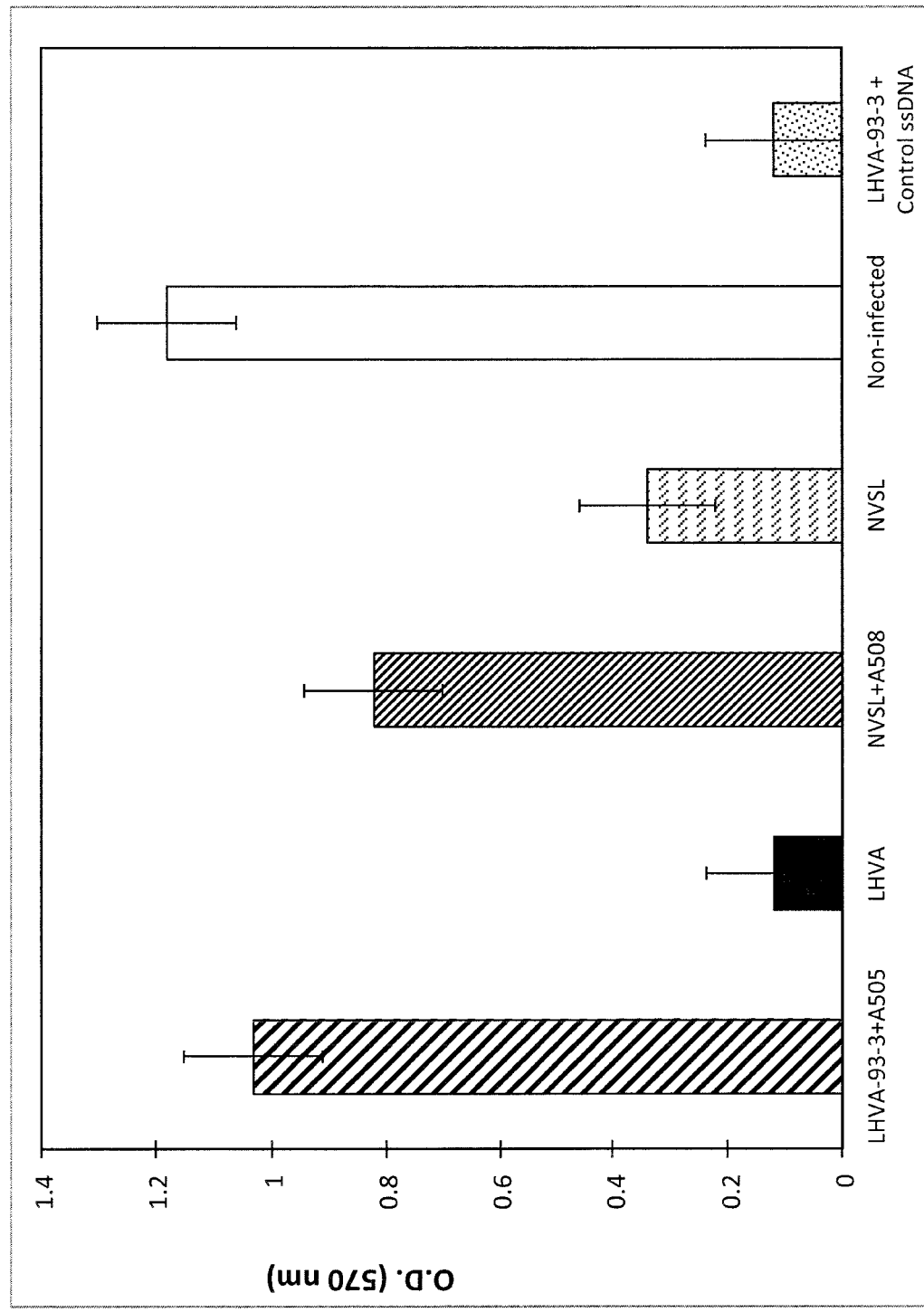
FIG. 9b is a histogram presentation depicting the protective effects of the A505 and A508 aptamers (each at 500 pmole) of the present invention on PRRSV infected PAMs or MARC-145 cells.

Aptamer ability to in-vitro protect cells from PRRSV infection was tested. As shown in FIG. 9a, cells treated with aptamer A505 prior to viral infection demonstrated a significant reduction in virus-associated cell-death. The protective effect peaked at a concentration between 1000 and 2000 pmole of A505. Accordingly, the effect of 500 pmole A505 on the infection of an additional viral strain NVSL was studied. As shown in FIG. 9b, this resulted in an approximate protection of 60% and 70% against infection of the cells with LHVA-3 and NVSL, respectively, when compared to non-infected MARC-145 cells. Interestingly, as also shown in FIG. 9b, A508 aptamer was also capable of reducing the in-vitro infectivity of the viruses, as compared to a non-relevant oligonucleotide control, which did not reduce cell mortality at all.

Figure 9C:
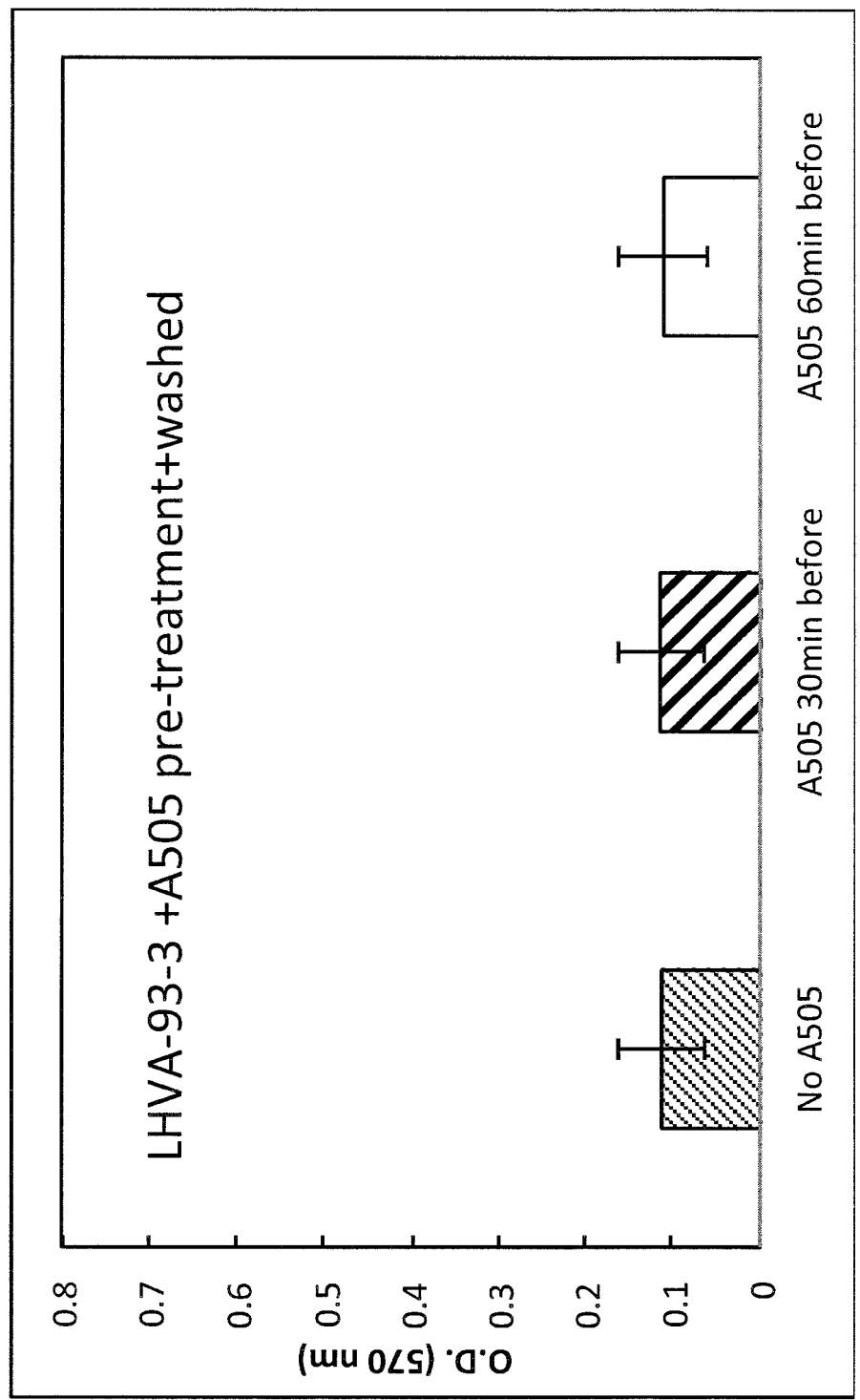
FIG. 9c is a histogram presentation illustrating a cell protective effect of A505 independent of the host cell proteins as determined by an MTT assay. PAMs or MARC-145 cells were incubated with PRRS virus 60 minutes following treatment for the indicated time periods with 50 pmole of A505. Note the insignificant difference between treated and control groups (p=0.237 for 30 minutes and p=0.09 for 60 minutes). Likewise, no significant difference in cell viability was evident between the two incubation times (p>0.05).
Figure 9D:
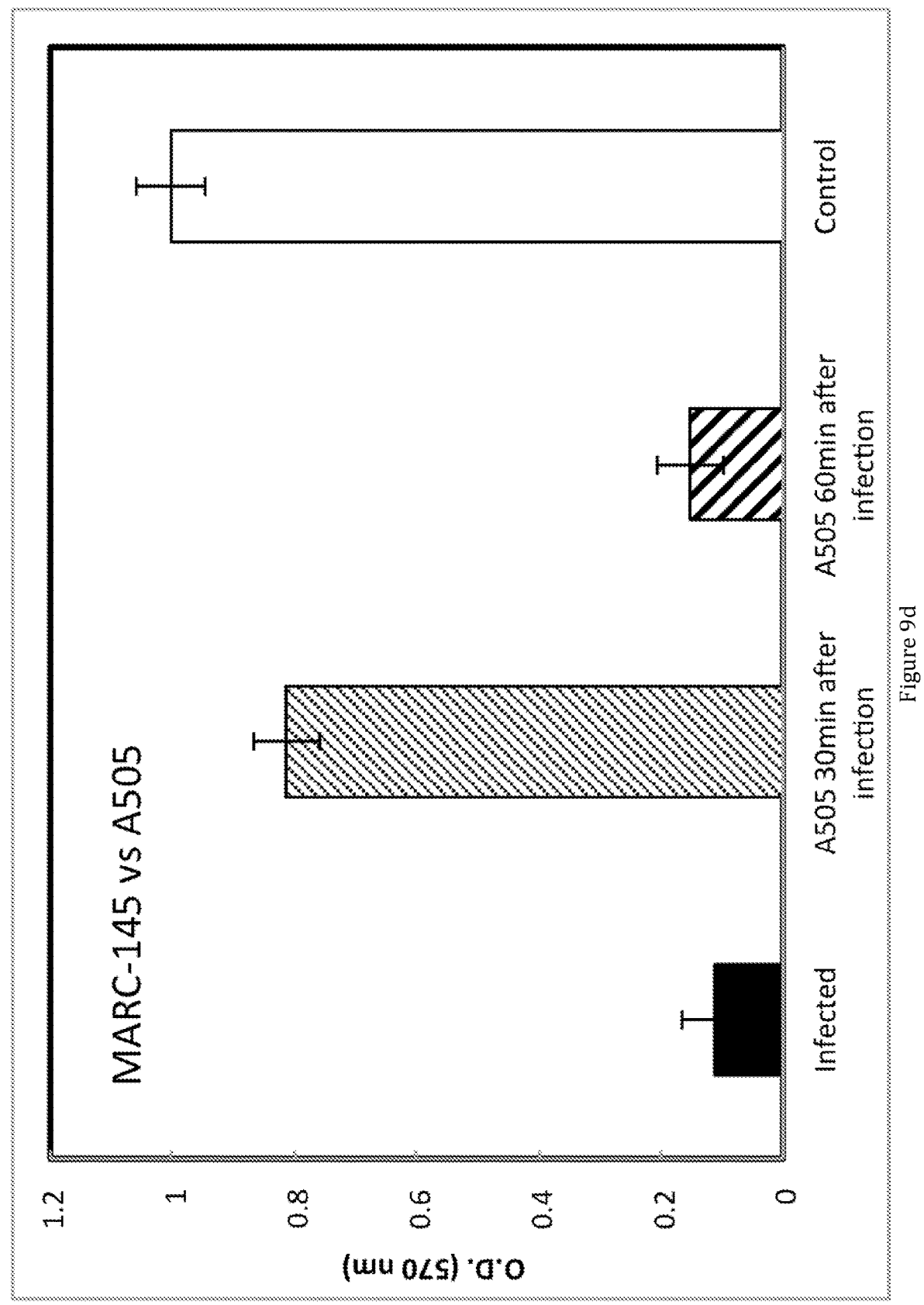
FIG. 9d is a histogram illustrating the protective effect of A505 on infected PAMs and MARC-145 cells as determined by an MTT assay. The PAMS and the MARC-145 cells were incubated with PRRS virus for 30 min or 60 min prior to treatment with 500 pmole A505 for 60 min. Note that although an insignificant effect of A505 on 60 minutes virus treated PAMs and MARC-145 cells was evident, a significant protective effect of A505 on 30 minutes virus treated PAMs and MARC-145 cells was seen as compared to non-infected cells.

The ability of the A505 aptamer to bind host proteins was then determined. Prior to viral infection, cells were incubated with A505 (500 pmole) for 30 min or 60 min, followed by repeated washing. As shown in FIG. 9c, no significant difference between the survival rate of non-treated and treated cells was evident, nor any difference between two exposures of the cells to A505 (i.e., prior to and following viral infection) could be detected. These results suggest that the inhibitory activity of A505 is not due to direct blocking the sialoadhesin containing receptors on host cells. In order to examine whether A505 is still protective if added following binding of the virus to the host cell receptors, MARC-145 cells were incubated with 500 TCID$_{50}$ LHVA-93-3 viruses for 30 min or 60 min prior to the treatment with 500 pmole A505 As shown in FIG. 9d, following 60 minutes incubation with the virus the effect of A505 was not significant. In contrast, the difference between non-infected cells and cells incubated with virus for 60 minutes was significant (p=0.0028). Notably, a highly significant difference was observed between the infected cells and those incubated with the virus for only 30 min prior to treatment with A505. Thus, these results suggest A505 cannot prevent cell-death once virus-host cell receptor interaction has reached its optimum.

Figure 10A:
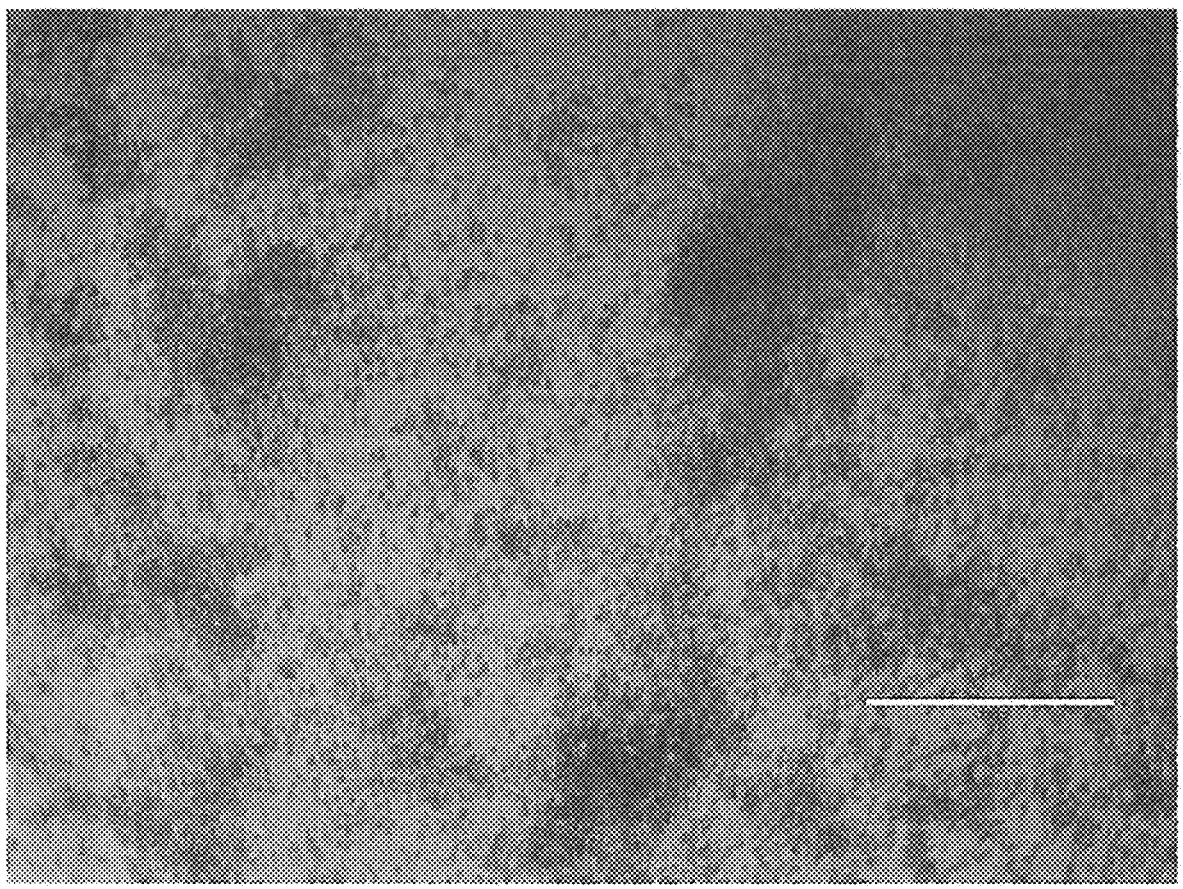
FIGS. 10a-f are photomicrographs depicting the effect of A505 on infection of cells with PRRSV.
Figure 10B:
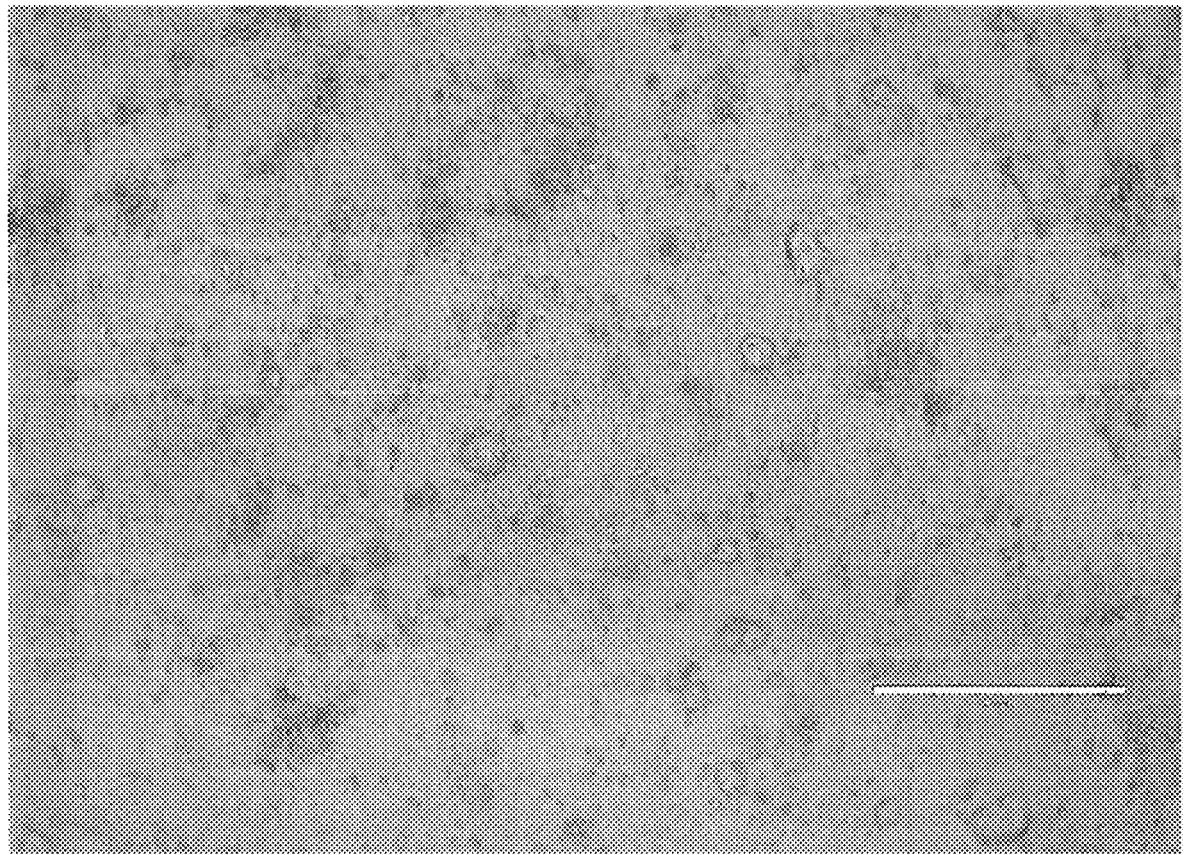
Figure 10C:
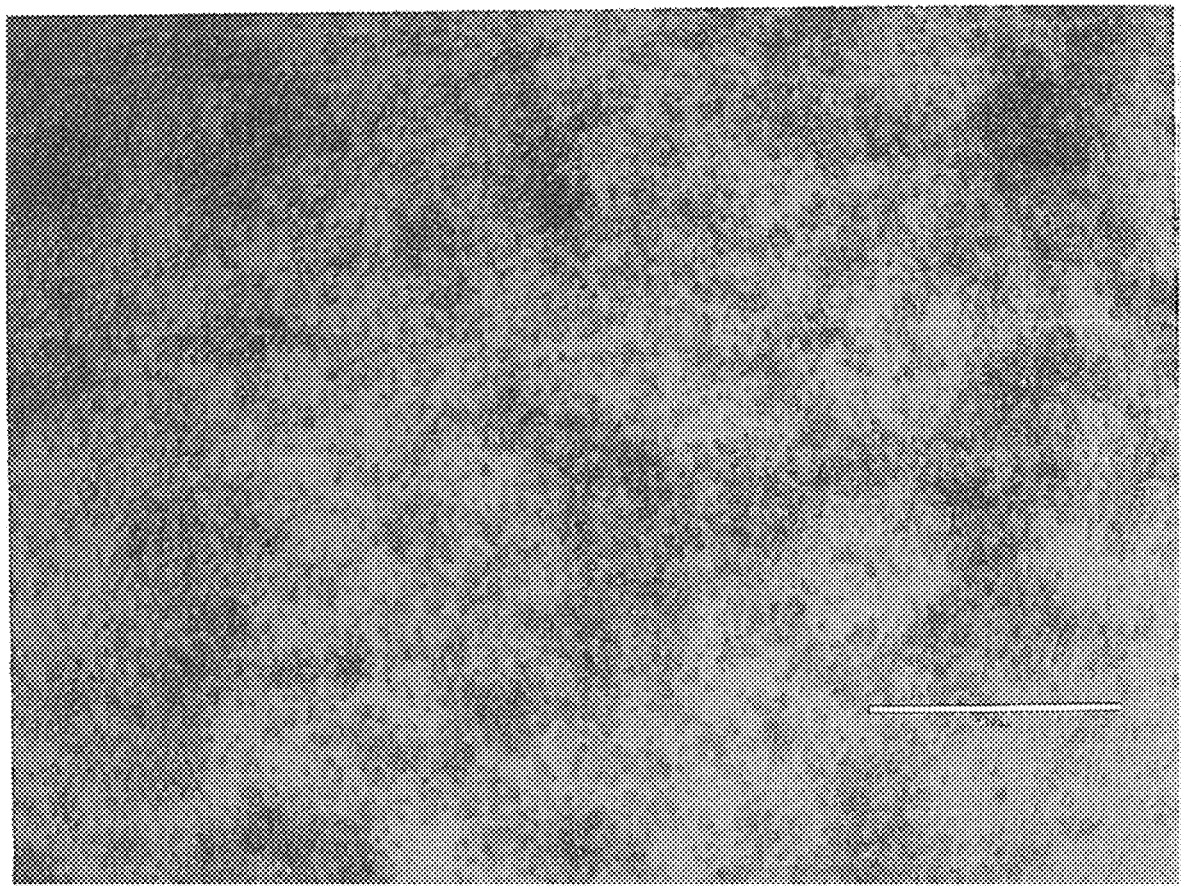
Figure 10D:
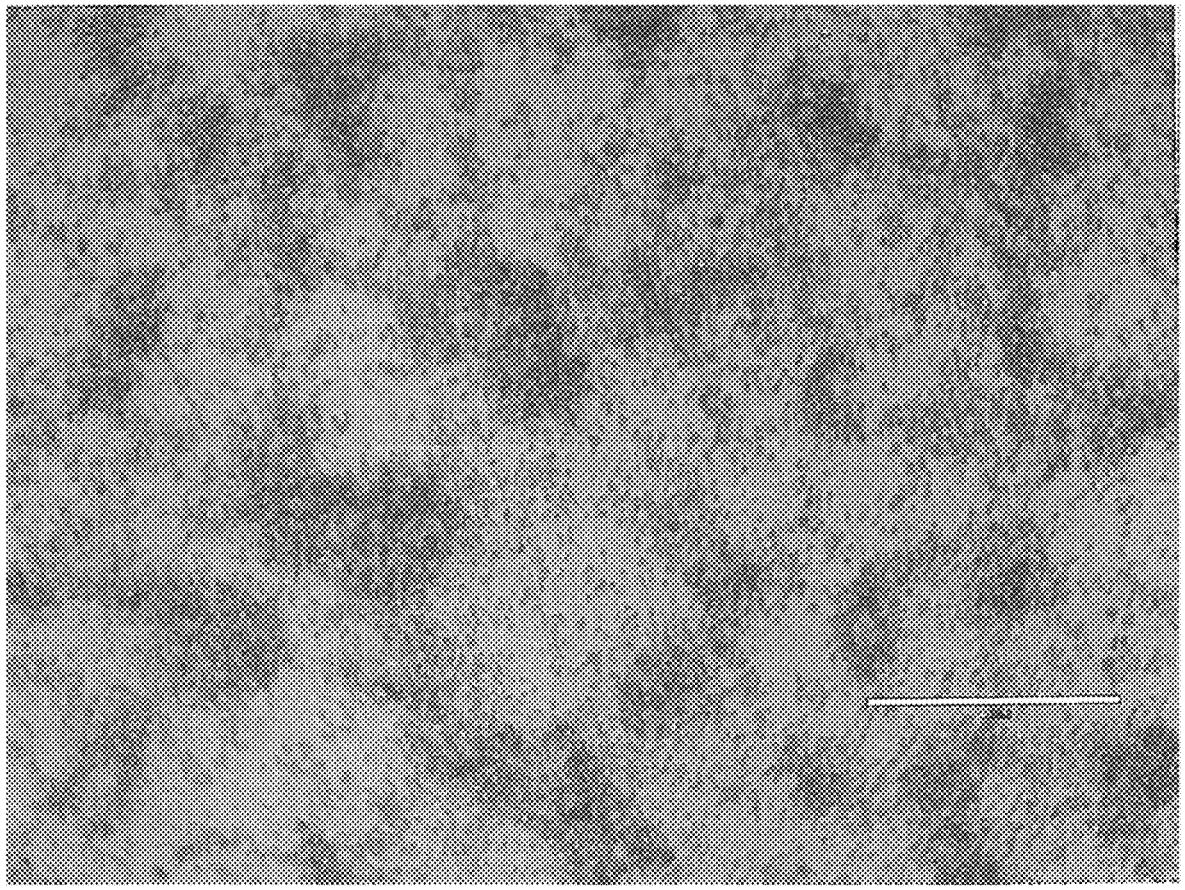
Figure 10E:
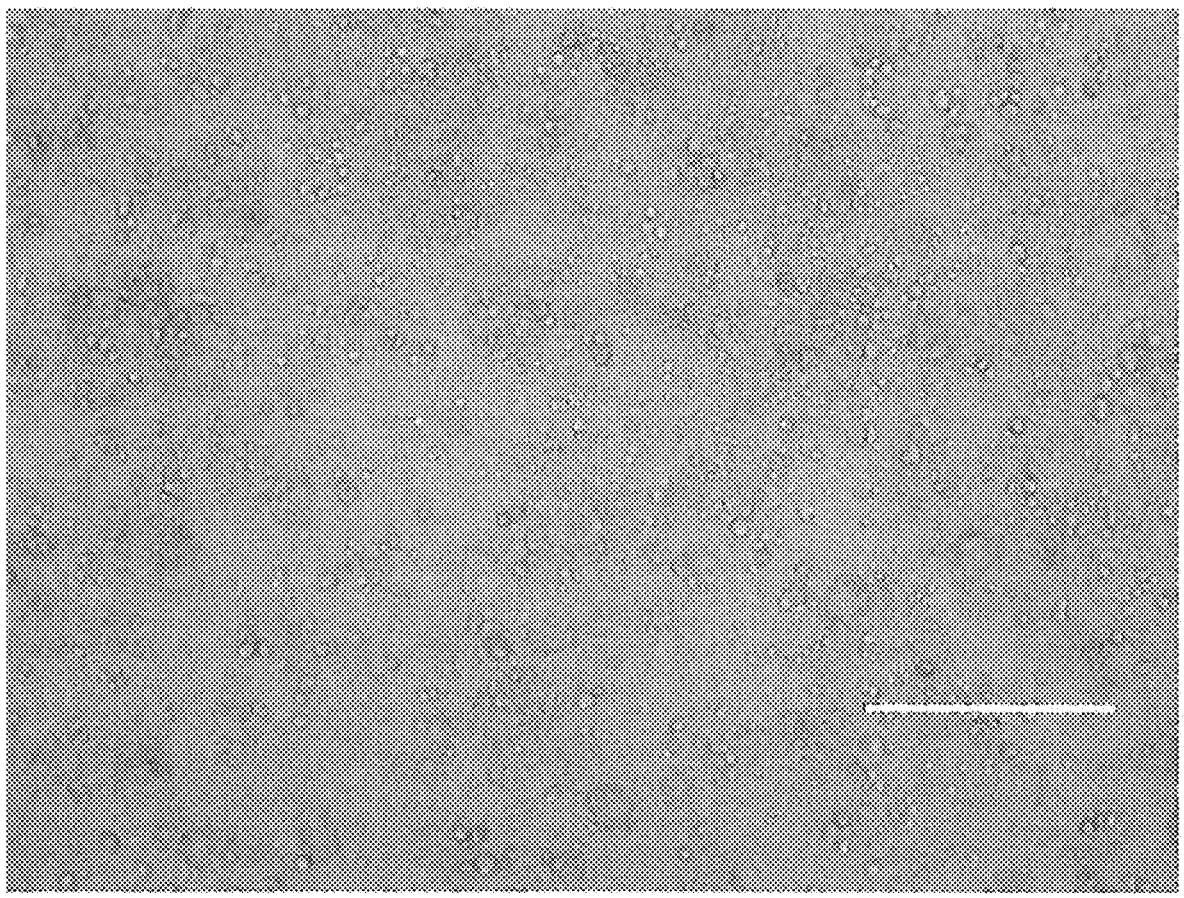
Figure 10F:
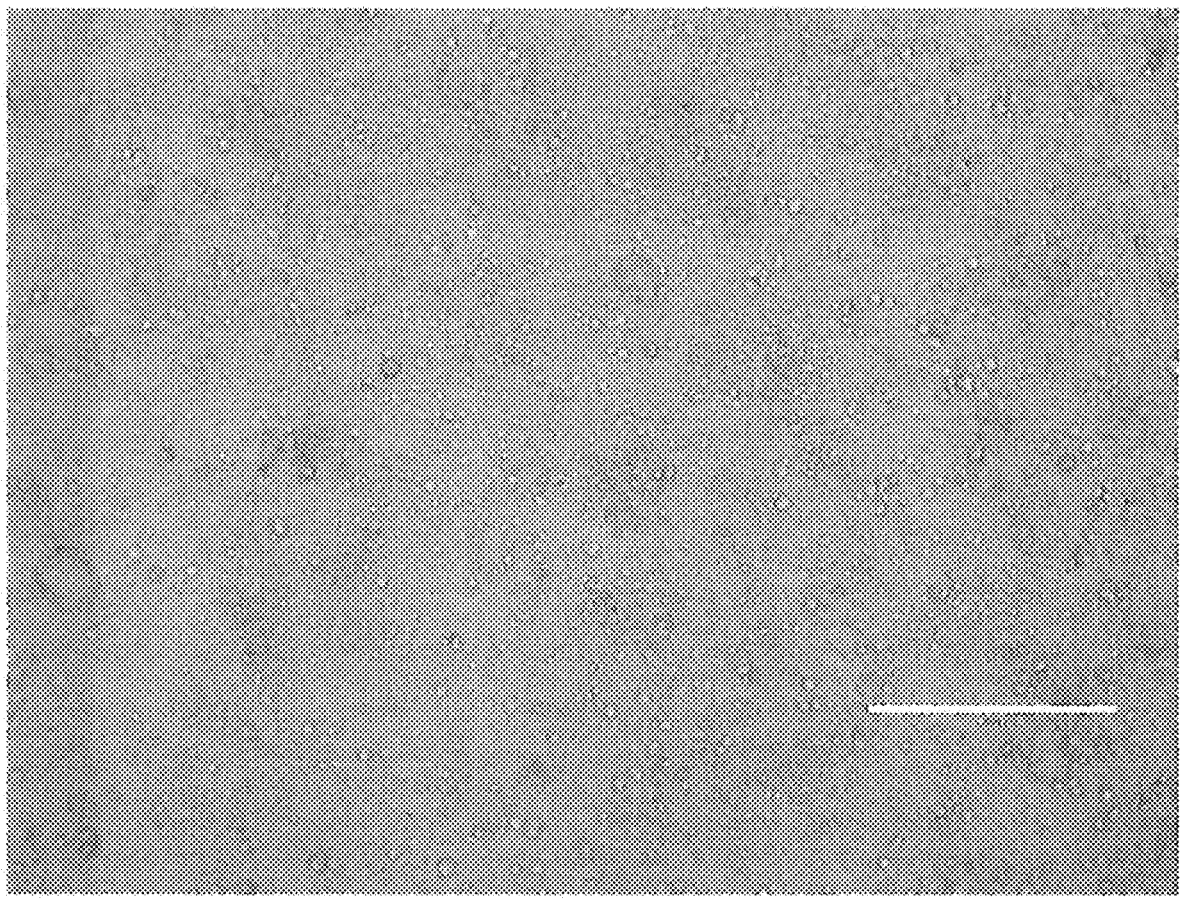
Figure 11:
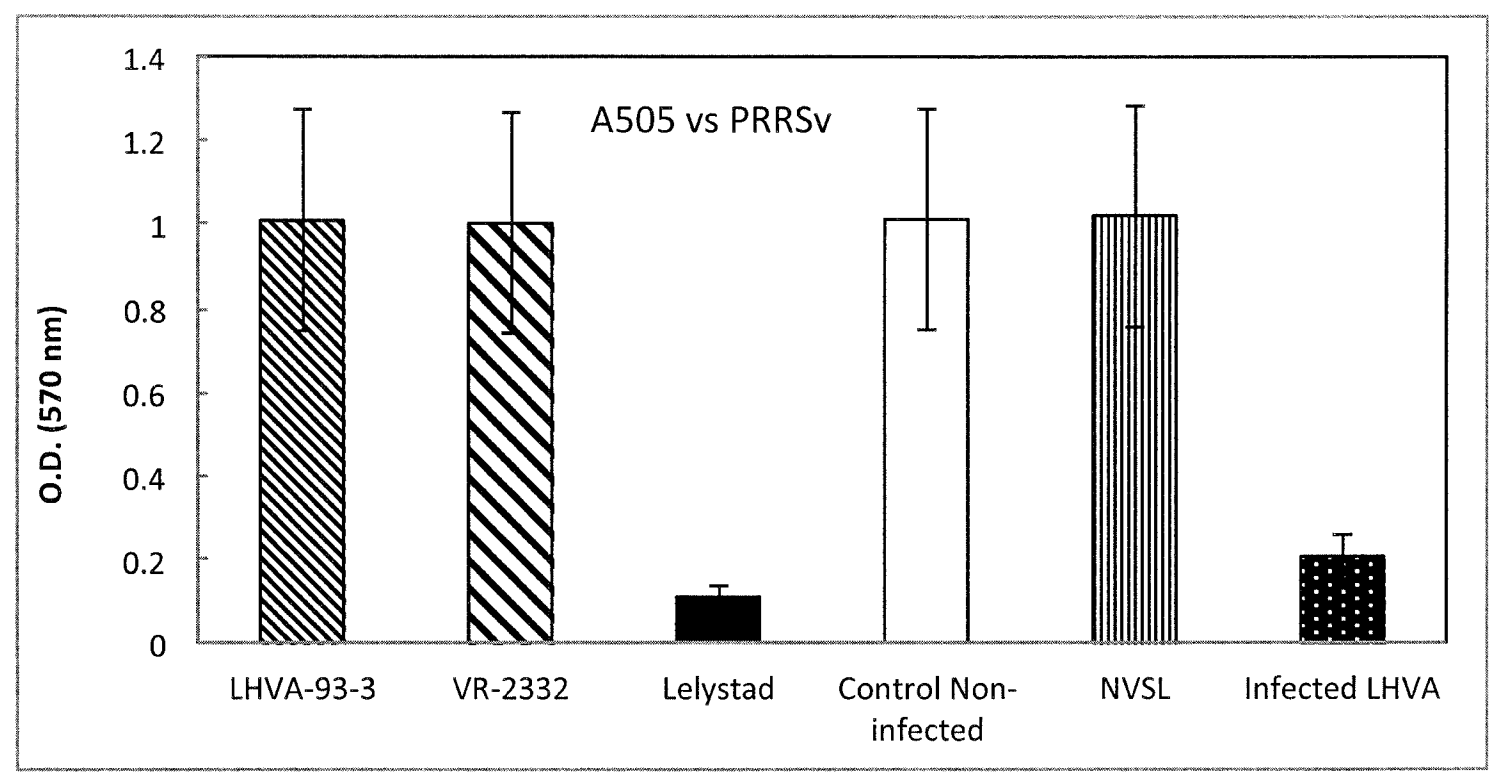

The effect of A505 in preventing viral binding and entry to cells was also demonstrated by microscopy analysis. As seen in FIGS. 10a-c, using light microscopy, the whole morphology of the MARC-145 cells was damaged by the viral infection (FIG. 10a). In comparison, in the presence of A505, destruction was inhibited and the cell morphology was largely conserved (FIG. 10b). Furthermore, the mere treatment with A505 did not affect the morphology of the cells (FIG. 10c), indicating that the damage was caused only by the PRRSV. These findings were further substantiated by immunofluorescence monitoring the viral presence using labeled specific monoclonal antibodies SWC3 (74-22-15) and CAM36A (detection of CD172a and CD14 respectively) both from VMRD (Pullman, Wash.). As shown, whereas viral presence is clearly manifested in the infected cells (FIG. 10d), it is almost entirely prevented by addition of A505 (FIG. 10e). Untreated cells appeared identical to the cells treated with A505 (FIG. 10f). Finally FIG. 11 shows the strain-specific immune response induced by the intact VS-232, LHVA-93-3, NVSL-93-2335, and Lelystad PRRS viruses. Here only the type 2 PRRSV have been neutralized by the A505 aptamer.

Example 3 In-Vivo Aptamer Protection from PRRSV Infection

The protective effect of the A505 aptamer against PRRSV infection (the LHVA-93-3 strain) was investigated in infected swine.

Materials and Experimental Procedures

Swine—SPF American Yorkshire swine at the age of 10-12 weeks were purchased. The selected swine were all exempt of PRRSV, SIV, and *Mycoplasma* Hyopneumoniae.

Animal Infection—

Swine were inoculated intranasally with sub-lethal infectious fluid containing 40TCID$_{50}$/ml PRRS virus (LHVA-93-3) with or without 2.5 nmole A505 aptamer for different time intervals. Pig body weight was monitored for 2 weeks. Viral titer in the lungs was determined by the CPE titration method (OIE Terrestrial Manual—May 2015, Chapter 2.8.7—Porcine Reproductive and Respiratory Syndrome, section 1.1.3). Other pigs were sacrificed 6 days following viral inoculation and lungs were removed and homogenized in PBS 0.1% BSA (10% w/v). Following homogenization, samples were centrifuged to remove debris and stored at −80° C.

Cell Viability Tests:

At the day of the experiment, thawed lung homogenates (i.e. the results from the bronchoalvelolar lung lavage) were transferred (100 μl of 10 fold serial dilution) into wells seeded with PAMs or Marc-145 cells; hence, 100 μl of the sample dilutions from the dilution plates to the corresponding wells of the plate with macrophages (first passage). The cells/viruses were incubated for 2-5 days and observe daily for a CPE. At day 2, seed macrophages in new microtitre plates. Fifty (50) μl of the supernatants were transferred from the plates of the first passage to the corresponding wells of the freshly seeded plates (second passage). The wells were incubated for 2-5 days and observed daily for a CPE. The results of the CPE assays were presented as log TCID$_{50}$.

Histology—

For lung histology, pigs were sacrificed at day 7 and lungs were removed into 10% neutral buffered formalin (pH 7.0). Lungs were then sectioned and stained with haemotoxylin and eosin.

Statistical Analyses—

Statistical analysis was performed by using the Student's t-test with p<0.05 considered as statistically significant.

Results—

The antiviral properties of A505 were determined in vivo prior to and following viral infection. Briefly, the swine were divided into four groups designated 'untreated', '0 day', '+1 day' and '+2 day'. Each pig was challenged with 40 TCID$_{50}$/ml of LHVA-93-3 PRRS viruses. Pigs in '0 day' group were inoculated with a mixture of the virus and 2.5 μmole/ml A505, intranasally (i.n.). Pigs in '+1 day' and '+2 day' groups were inoculated with 2.5 μmole/ml A505, in 1 day or 2 days following virus infection, respectively. PRRS infection was monitored by three parameters, including (i) body weight loss during 14 days following virus treatment; (ii) lung virus titre; (iii) histological examination of lungs—sections were taken 7 days following virus inoculation.

Figure 12A:
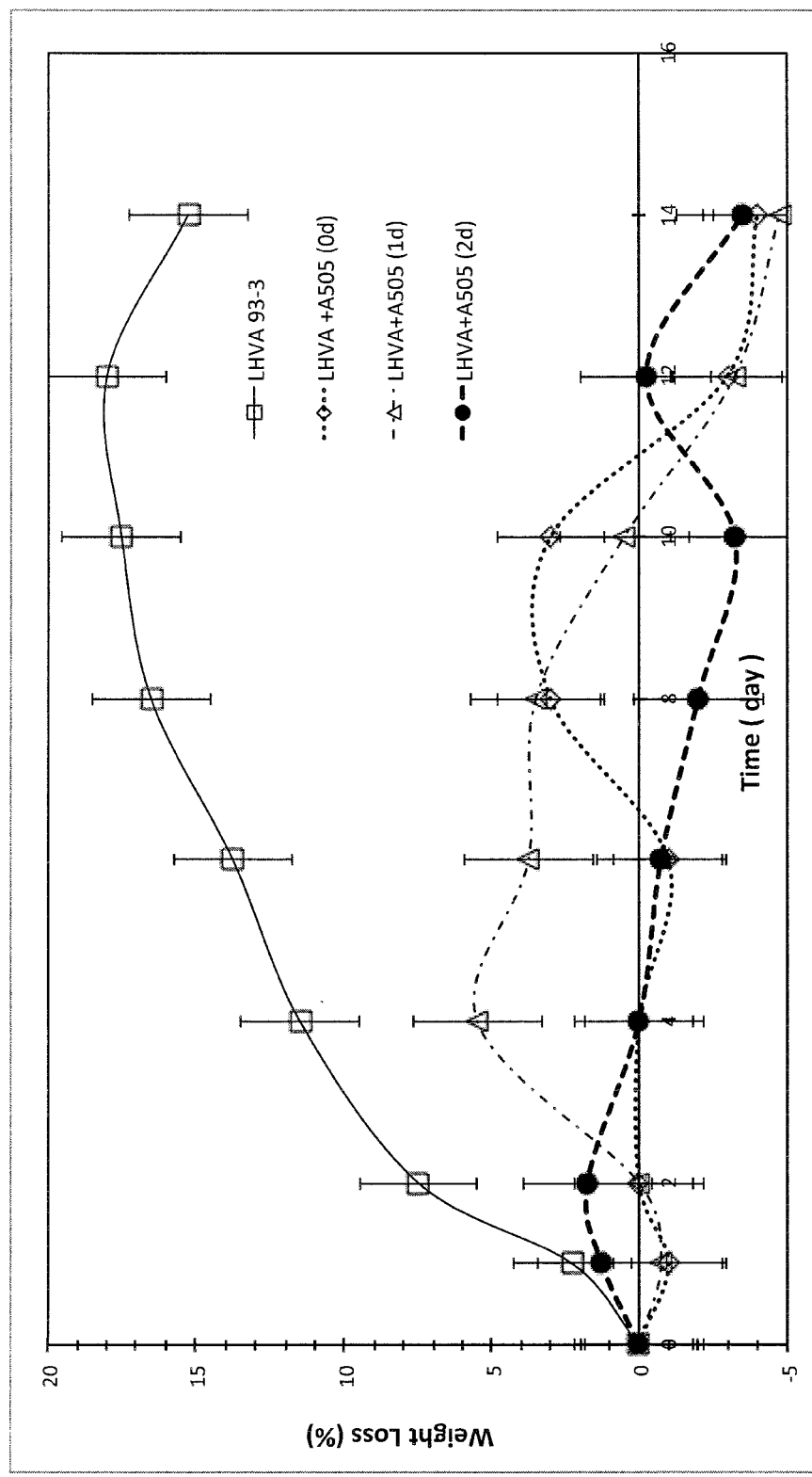
FIG. 12 Inhibition of in-vivo PRRSv infection by A505. (a) The effect of A505 treatment on the body weight loss of the swine infected with LHVA-93-3. In contrast to the control-infected group, A505-treated swine showed significantly lower weight loss and recovered weight much more quickly (p<0.05). (b) The effect of A505 on the viral burden in the lungs of PRRSv-infected swine. All swine were infected with a sublethal dose, namely 40 TCID$_{50}$/ml of LHVA-93-3. The swine were divided into four groups according to the time of their treatment with A505 (1 day after concomitantly, or 2 days after infection). Six days following the infection, the swine were sacrificed, their lung homogenized and assayed for virus level by CPE tests. The results are presented as log infection doses 50% (TCID$_{50}$/ml). The level of reduction of viral load in all three groups of the A505-treated swine is statistically significant when compared with the swine in the infected groups (p<0.05).
Figure 12B:
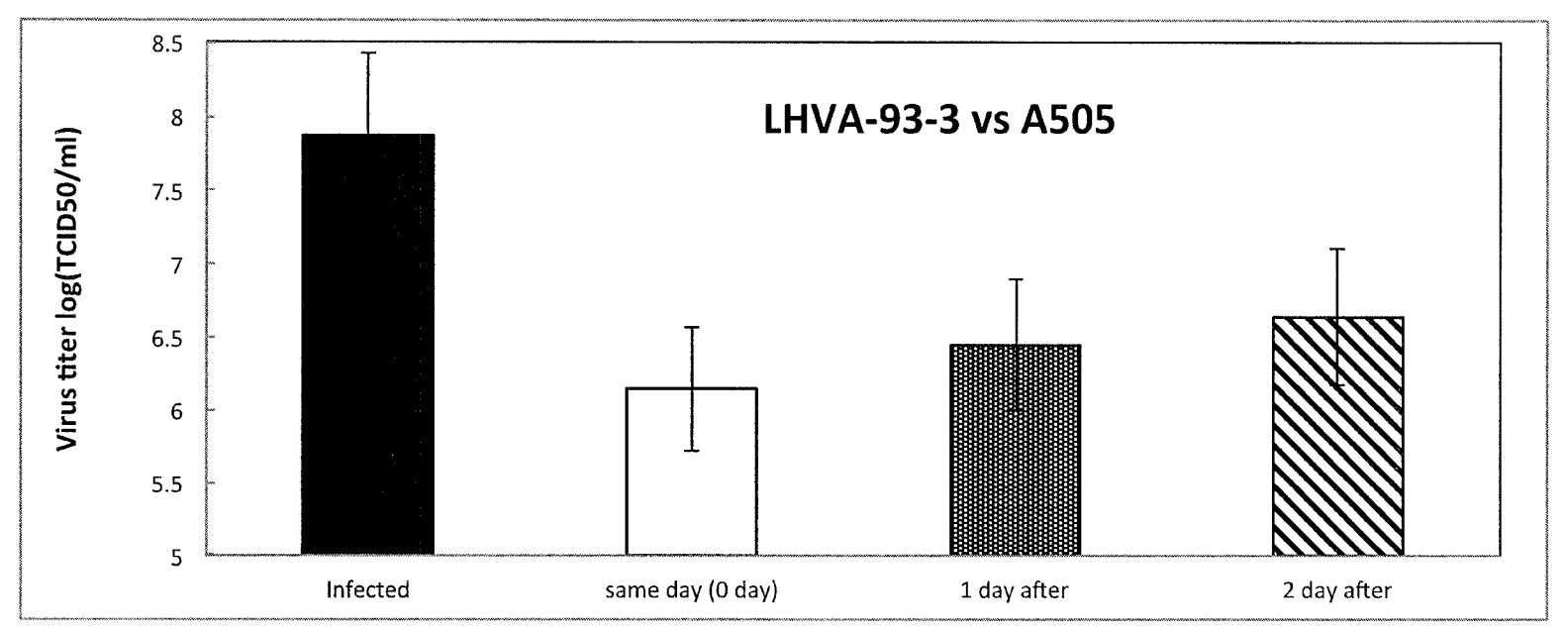

The histological findings suggest that administration of A505 reduces the inflamed areas in lungs. Furthermore, compared to control group, treatment groups (+2 day, 0 day and +1 day) showed significantly lower weight loss and enhanced recovery (FIG. 12a). The protective capacity of A505 was also investigated using the whole CPE titration method (OIE-2015) measuring the viral load in lungs of pigs. As shown in FIG. 12b, pigs treated with 2.5 μmole/ml A505 (125 μmole/pig) for different time intervals demonstrated protective effect against viral challenge as compared to non-treated pigs. The protective effect in the '0 day group' was manifested in more than 2 log difference in lung virus titer compared to the non-treated group (infected), which is equivalent to over 99% protection. Further protection with the A505 was observed between '+1 day' and '+2 day' groups.

These results suggest that A505 is effective before and even several days after the infection. It will be appreciated that since only low concentrations of A505 were used in this protection experiment (μmole/ml concentration), the protective effect of A505 can be further increased by adjusting the dose (mg/Kg) of A505.

Example 4 Aptamer Treatment Confers Protection Against Infection by Various PRRSV Strains Since the receptor-binding region of the peptidic M-S-S-GP5 complex is a highly conserved region, it was of interest to test whether the protective effect of A505 is manifested also towards infection with other PRR virus strains. It was also of interest to compare the effect of the aptamer to that of a currently only available "anti-PRRSV therapy", the antibiotic Tilmicosin[liv].

Materials and Experimental Procedures

Materials—

Tilmicosin (Pulmotil®) was purchased from Eli Lilly (Elanco®), Canada.

Animals and Infection Procedures—

Were implemented as described hereinabove. A dose of 15 ug/Kg of A505 was used.

Results—

Figure 13A:
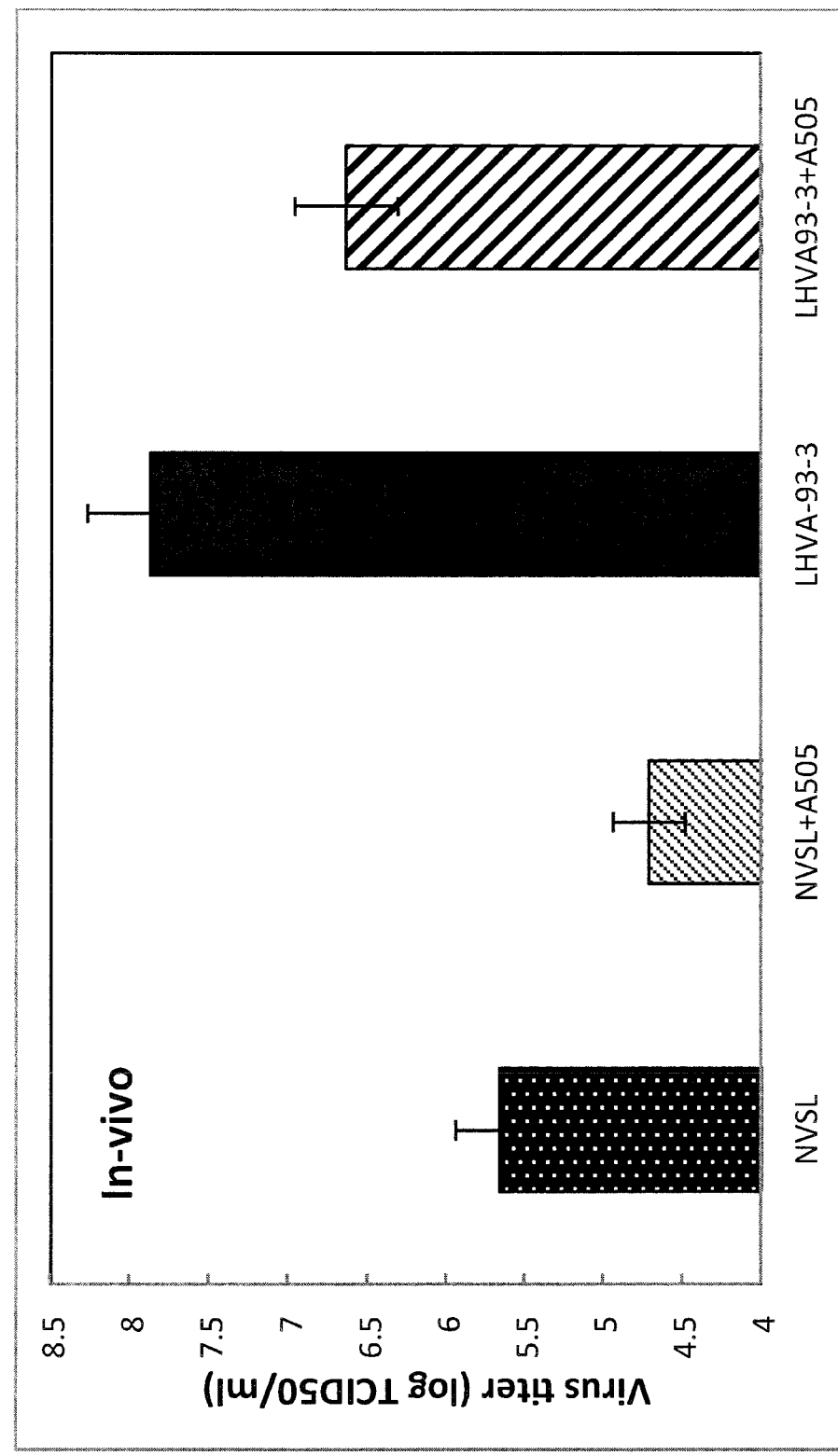
FIG. 13a shows a graph depicting the inhibition of swine infection with several strains of PRRSv (each at 40TCID$_{50}$/ml) using the A505 aptamers.
Figure 13B:
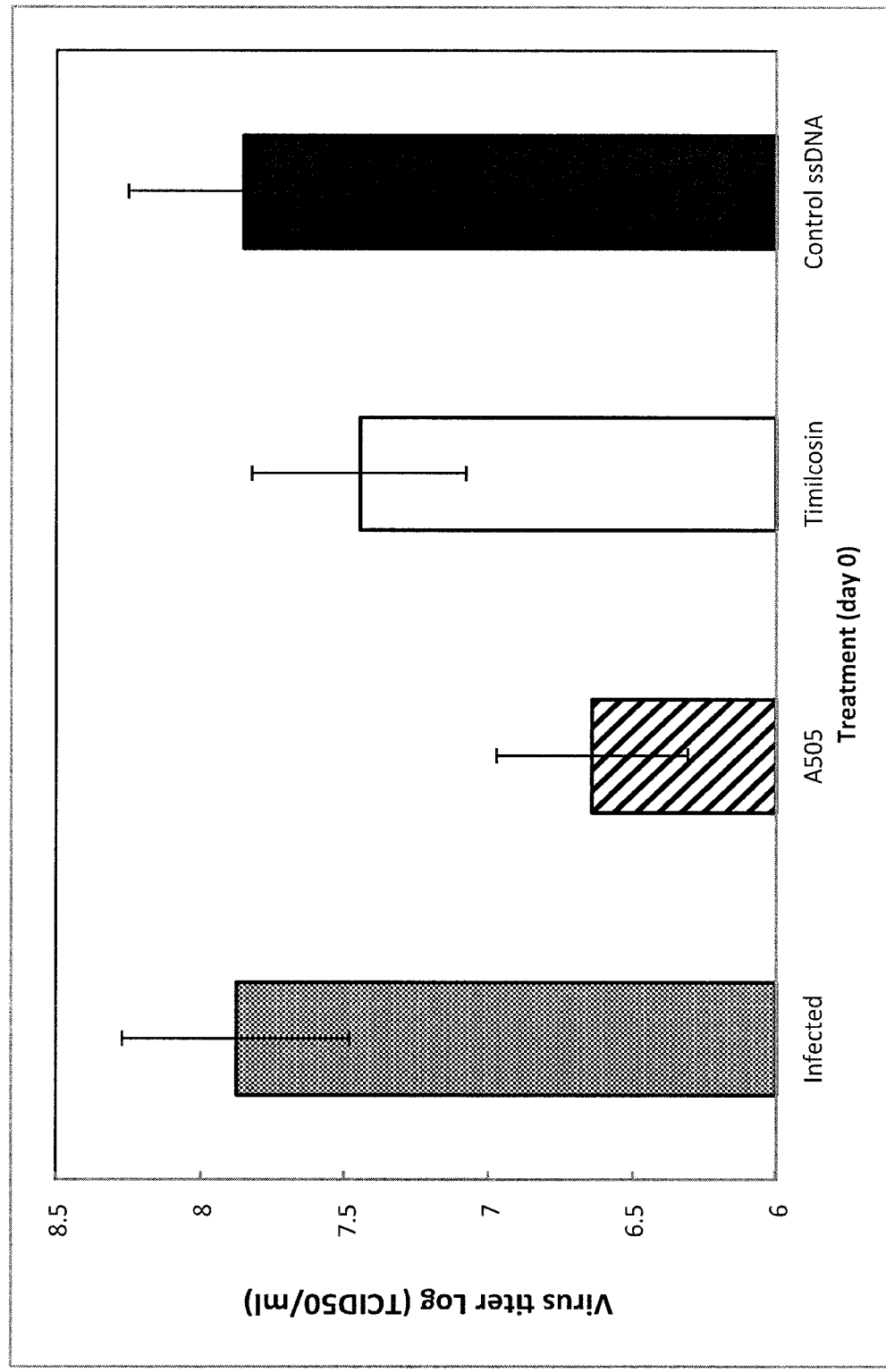
FIG. 13b is a graph depicting inhibition of swine infection with the LHVA-93-3 using the A505 of the present invention, as well as a control oligonucleotide and the antibiotic Tilmicosin.

The results are shown in FIG. 13a, which demonstrates the reduction in the lung virus titer in pigs infected with two strains of PRRSV, as a result of treatment with A505 on the day of infection. It is noteworthy that A505 is efficient in preventing the infection by all tested strains of PRRSV. These findings corroborate the results of the in vitro assay presented in FIG. 13b. In contrast to A505, a control irrelevant nucleotide A501, led to an insignificant change in the viral titer. It is of interest that the aptamer A508, although less effective than A505 was still capable of reducing the lung virus titer of LHVA-93-3 (see FIG. 13b).

The ability of the A505 aptamer to inhibit PRRSV infection was also compared to that of one of the currently available "anti-PRRSV" drugs, the antibiotic Tilmicosin. To this end, both A505 and Tilmicosin were administered once, together with the virus, using the intra-nasal route. As is shown in Table 2 below, a dose of 60 mg/pig of Tilmicosin (1 mg/kg body weight) reduced virus titer by 0.42 log TCID$_{50}$, representing a 2.6-fold reduction in virus burden. This is in comparison to a reduction by 1.21 log TCID$_{50}$ affected by A505 in this particular experiment (over 10 fold reduction in virus burden).

TABLE 2

| Agent | Δ (log TCID$_{50}$) | Reduction Factor |
| --- | --- | --- |
| A505 | 1.23 | 17.1 |
| Tilmicosin | 0.42 | 2.6 |

Altogether these results suggest a mechanism of action for the aptamer sequences of the present invention, essentially, direct binding to the receptor binding region of the PRRS virus surface, thereby preventing attachment of the virus to the host cell and consequently viral entry to the host cell.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCE LIST

[i] B. Mole, Deadly pig virus slips through US borders. Nature, 2013, vol. 499, pp. 388. Also D. J. Holtkampetal et al., Assessment of the economic impact of PRRSV on the United States Pork Producers, J. of Swine Health & Prod., 2013, vol. 21, pp. 72-84. Also, R. B. Baker, Exploring the Science behind the Biosecurity and PRRSV, in National Hog Farmer, 2012, April 18th. Also P. Yeske, Cost of eradicating diseases according to method, in Proc. of the Annual Meeting of the Am. Asso. of Swine Veterinarians. 2010, pp. 15-18. Also E. J. Neumann et al., Assessment of the economic impact of porcine reproductive and respiratory syndrome on swine production in the United States. J. of Am. Vete. Med. Asso., 2005, vol. 227, pp. 385-392. Also X. de Paz, PRRS cost for the European Industry, in Pigg333, Aug. 17, 2015

[ii] S. Dee, et al., Evidence of long distance airborne transport of porcine reproductive and respiratory syndrome virus and Mycoplasma Hyopneumoniae. Vet. Res., 2009, vol. 40, 13 pages. Also see S. Otake et al, Long distance airborne transport of infectious PRRSV and Mycoplasma Hyopneumoniae from a swine population infected with multiple viral variants Vet. Microbial, 2010, vol. 145, pp. 198-208. Also Also, H. Zhang et al., Airborne spread and infection of a novel swine-origin A (H1N1) virus. Virology Journal, 2013, vol. 10, pp 204.

K. Han et al., Effects of North American PRRSV-based Modified Live Vaccines on Pre-immunized Sows Artificially Inseminated with European PRRSV-spiked Semen. Clinical Vaccine Immunology, 2012, vol. 19, no. 3, pp. 319-324. Also C. Klopfenstein et al., Regional PRRS control with an autogenous vaccination strategy. Proceedings of Journées Recherche Porcine—Aug. 16, 2012, vol. 44, pp. 93-94. Also J. E. Abrahante et al., Efficacy of PRRSV vaccines against homologous and heterologous strain challenge. Proceedings of the 2010 Int. PRRS Symposium, Dec. 3-4, 2010, Chicago. Paper #51. Also E. Pileri et al. Quantification of PRRSV transmission: Effect of pig vaccination. Proceedings of the 2013 Int. PRRS Symposium, May 20-22, 2013, Beijing, paper #38. Also T. G. Kinman et al. Challenges for porcine reproductive and respiratory syndrome virus (PRRSV) vaccinology. Vaccine, 2009, vol. 27, pp. 3704-3718.

[iv] T. Dokland, The structural biology of PRRSV, Virus Research, 2010, vol. 154, pp. 86-97. Also W. van Breedam et al., Porcine reproductive and respiratory syndrome virus entry into porcine macrophage: A Review. J. of Gen. Virol, 2010, vol. 91, pp. 1659-1667. Also N. Music and C. A. Gagnon, The role of porcine reproductive and respiratory (PRRS) virus structural and non-structural proteins in virus pathogenesis. Ani. Health Res. Rev, 2010, vol. 11, pp. 135-163. S. Dea et al., Current knowledge on the structural proteins of porcine reproductive and respiratory syndrome (PRRS) virus: comparison of the North American and European isolates. Arch. Virol. 2000, vol. 145, pp. 659-688.

[v] Y. Du et al. Antiviral Activity of Tilmicosin for Type 1 and Type 2 Porcine Reproductive And Respiratory Syndrome Virus In Cultured Porcine Alveolar Macrophages. J. of Antivirals & Antiretrovirals, 2011, vol. 3, pp. 28-33. Also M. Miser et al. Preliminary evaluation of clinical effects and cost-effectiveness of in-feed Pulmotil® (Tilmicosin) and serum inoculation in an outbreak of PRRSV. Proc. of the 19th IPVS Congress, Copenhagen, Denmark, 2006, vol. 2, p. 13.

[vi] Y. Fang et al., 2007. Diversity and evolution of a newly emerged North American Type 1 porcine arterivirus: analysis of isolates collected between 1999 and 2004. Arch. Virol., 2007, vol. 152, pp. 1009-1017. Also E. J. Snijder et J. J. Meulenberg, The molecular biology of arteriviruses. J. of Gen. Virol., 1998, vol. 79, pp. 961-979. E. J. Snijder et al., The coranoviruslike superfamily. Adv. Exp. Med. Biol., 1993, vol. 342, pp 235-244.

[vii] E. Nam et al., Complete genomic characterization of a European type 1 porcine reproductive and respiratory syndrom virus isolate in Korea. Arch. Virol., 2009, vol. 154, pp. 629-638.

[viii] M. S. Spilman et al. Cryo-electron tomographyof porcine reproductive and respiratory syndrome virus: organization of the nucleocapsid. J. Gen. Virol. 2009, vol. 90, pp. 527-535. Also M. Barcena et al., Cryo-electron tomography of mouse hepatitis virus: Insights into the structure of the coronavirion. PNAS, 2009, vol. 106, pp. 582-587.

[ix] W. van Breedam et al., The M/GP5 Glycoprotein Complex of Porcine Reproductive and Respiratory Syndrome Virus Binds the Sialoadhesin Receptor in a Sialic Acid-Dependent Manner. PLoS Patho., 2010, vol. 6, p 1000730. Also E. J. J. Wissink et al., Envelop protein requirements for the assembly of infectious virions or porcine reproductive and respiratory syndrome virus. J. of Virol., 2005, pp. 79, pp. 12495-12506. Also S. Dea et al., Ultrastructural characteristics and morphogenesis of porcine reproductive and respiratory syndrome virus propagated in the highly permissive MARC-145 cell clone, in Corona- and related viruses. Ed. by, P. J. Talbot and G. A. Levy. Plenum Press, N Y, 1995, pp. 95-98.

[x] OIE Terrestrial Manual—May 2015, Chapter 2.8.7—Porcine Reproductive and Respiratory Syndrome, section 1.1.3 (http://www.oie.int/fileadmin/Home/eng/Health_standards/tahm/2.08.07_PRRS.pdf). Also G. Nodelijk, Porcine reproductive and respiratory syndrome (PRRS) with special reference to clinical aspects and diagnosis: A Review. Veterinary Quarterly, 2002, vol. 24, pp. 95-100.

[xi] Q. Li et al. Rapid detection of porcine reproductive and respiratory syndrome virus by reverse transcription loop-mediated isothermal amplification assay. *J. Virol. Methods,* 2009, vol. 155, pp. 55-60. Also H. K. Chung et al. Detection and differentiation of North American and European genotypes of porcine reproductive and respiratory syndrome virus in formalin-fixed, paraffin-embedded tissues by multiplex reverse transcription-nested polymerase chain reaction. *J. Vet. Diagn. Invest.,* 2002, vol. 14, pp. 56-60.

[xii] J. Christopher-Hennings et al. Porcine reproductive and respiratory syndrome (PRRS) diagnostics: Interpretation and limitations. *J. of Swine Health & Prod.* 2002, vol. 10, pp. 213-218.

[xiii] D. S. Wilson & J. W. Szostak. In vitro selection of functional nucleic acids. *Annual Rev. Biochem.,* 1999, vol. 68, pp. 611-647. Also A. Cibiel et al. Methods to identify aptamers against cell surface biomarkers. *Pharmaceuticals,* 2011, vol. 4, pp. 1216-1235. Also B. Hall et al. Design, synthesis, and amplification of DNA pools for in vitro selection. *Current Protocols in Molecular Biology,* 2009, vol. 88, pp. 24.2.1-24.2.27. Also S. Chandra & B. Gopinath. Methods developed for SELEX. *Anal. Bioanal. Chem.,* 2007, vol. 387, pp. 171-182.

[xiv] G. Mayer. The chemical biology of aptamers: A Review. *Angew. Chem. Int. Ed.,* 2009, vol. 48, pp. 2672-2689. Also A. D. Keefe et al, Aptamers as therapeutics, *Nature Reviews: Drug discoveries,* 2010, vol. 9 pp. 537-550.

[xv] S. Balamuragan et al. Surface immobilisation methods for aptamer diagnostic applications. *Anal. Bioanal. Chem.,* 2008, vol. 390, pp. 1009-1021.

[xvi] Y. Zhang et al. Tumor-targeted drug delivery with aptamers. *Curr. Med. Chem.,* 2011, vol. 18, pp. 4185-4194.

[xvii] K. Sefah et al. Nucleic acid aptamers for biosensors and bio-analytical applications, *Analyst,* 2009, vol. 134, pp. 1765-1775. Also E. Torres-Chavolla & E. C. Alocilja. Aptasensors for detection of microbial and viral pathogens. *Biosensors & Bioelect,* 2009, vol. 24, pp. 3175-3182. Also Y. Xiao et al. Preparation of electrode-immobilized, redox-modified oligonucleotides for electrochemical DNA and aptamer-based sensing. *Nature Protocols,* 2007, vol. 2, pp. 2875-2880. I. Willner and M. Zayats. Electronic Aptamer-Based Sensors. *Angew. Chem., Int. Ed.,* 2007, vol. 46, pp. 6408-6418. Also M. Labib et al. Aptamer-based viability impedimetric sensors for viruses. *Anal. Chem.,* 2012, vol. 84, pp. 1813-1816.

[xviii] T. Misono et al. Selection of RNA aptamers against human PRRS virus hemagglutinin using surface plasmon resonance. *Anal. Biochem.,* 2005, vol. 342, pp. 312-317. Also R. Yamamoto et al. Molecular beacon aptamer fluoresces in the presence of Tat protein of HIV-1. *Genes Cells,* 2000, vol. 5, pp. 371-388. Also D. G. Ahn et al. RNA aptamer-based sensitive detection of SARS coronavirus nucleocapsid protein. *Analyst,* 2009, vol. 134, pp. 1896-1901. Also K. J. Jang et al. Isolation of inhibitory RNA aptamers against severe acute respiratory syndrome (SARS) coronavirus NTPase/Helicase. *Biochem. Biophys. Res. Commun.* 2008, vol. 366, pp. 738-744. Also S. H. Jeon et al. A DNA Aptamer Prevents PRRS Infection by Blocking the Receptor Binding Region of the Viral Hemagglutinin. *J. of Biol. Chem.* 2004, vol. 279, pp. 48410-48419. Also S. C. B. Gopinath et al. An Efficient RNA Aptamer against Human PRRS B Virus Hemagglutinin. *J. of Biochem.* 2006, vol. 139, pp. 837-846. Also M. Wongphatcharachai et al. Neutralizing DNA aptamers against Swine Influenza H3N2 viruses. *J. of Clini. Microbial.,* 2013, vol. 51, pp. 46-54. Also S. Sekiya et al. Structure/Function Analysis of an RNA Aptamer for Hepatitis C Virus NS3 Protease. *J. of Biochem.,* 2003, vol. 133, pp. 351-359.

[xix] R. E. Wang et al. Improving the stability of aptamers by chemical modifications. *Curr. Medi. Chem.,* 2011, vol. 18, pp. 4126-4138.

[xx] F. A. Zuckermann et al. Assessment of the efficacy of porcine reproductive and respiratory syndrome virus (PRRSV) vaccines based on measurement of serologic response, frequency of gamma IFN producing cells and virological parameters of protection upon challenge. *Vet. Microbiology,* 2007, vol. 123, pp. 69-85. Also D. Linhares et al. Effect of modified live porcine reproductive and respiratory syndrome (PRRS) vaccine on the shedding of wild-type virus from an endemically infected population of growing pigs. *Vaccine,* 2012, vol. 30, pp. 407-413.

[xxi] P. S. Martelli et al., Efficacy of a modified live porcine reproductive and respiratory syndrome virus (PRRSV) vaccine in pigs naturally exposed to a heterologous European (Italian cluster) field strain: clinical protection and cell-mediated immunity. *Vaccine,* 2009, vol. 27, pp. 3788-3799.

[xxii] see http://en.wikipedia.org/wiki/DNA_vaccination

[xxiii] B. Pirzadeh and S. Dea. Immune response in pigs vaccinated with plasmid DNA encoding ORF5 of porcine reproductive and respiratory syndrome virus. *J. Gen. Viral.,* 1998, vol. 79, pp. 989-999. Also P. W. Jiang et al. Humoral immune response induced by oral administration *S. Typhimurium* containing a DNA vaccine against porcine reproductive and respiratory syndrome virus. *Vet. Immunol. & Immunopathol.* 2004, vol. 102, pp. 321-328. Also B. Li et al. Immunogenicity of the highly pathogenic porcine reproductive and respiratory syndrome virus GP5 protein encoded by synthetic ORF5 gene. *Vaccine,* 2009, vol. 27, pp. 1957-1963. Also L. Fang et al. Enhanced immunogenicity of modified GP5 of porcine reproductive and respiratory syndrome virus. *Virus Genes,* 2006, vol. 32, pp. 5-11.

[xxiv] Y. Jiang et al. DNA vaccines co-expressing GP5 and M proteins of porcine reproductive and respiratory syndrome virus (PRRSV) display enhanced immunogenicity. *Vaccine,* 2006, vol. 24, pp. 2869-2879.

[xxv] O M. Zuker, MFold web server for nucleic acid folding and hybridization prediction. *Nucleic Acid Research,* 2003, vol. 31, pp. 3406-34-15. Available at http://mfolds-na.albany.edu/?q=DINAMelt/Quickfold.

[xxvi] O M. Zuker, MFold web server for nucleic acid folding and hybridization prediction. *Nucleic Acid Research,* 2003, vol. 31, pp. 3406-34-15. Available at http://mfol-d.rna.albany.edu/?q=DINAMelt/Quickfold.

[xxvii] H. L. Xu et al, Immune Evasion of Porcine Reproductive and Respiratory Syndrome Virus through Glycan Shielding Involves both Glycoprotein 5 as Well as Glycoprotein 3. *J. of Virology,* 2011, vol. 85, pp. 5555-556. Also M. Dalziel et al. Emerging Principles for the Therapeutic Exploitation of Glycosylation. *Science,* 2014, vol. 343. DOI: 10.1126/science.1235681.

[xxviii] D. Kolarich et al., Determination of site-specific glycans heterogeneity on glycoproteins, *Nature Protocols,* 2012, vol. 7, pp. 1285-1298. Also P. Jensen et al., Structural analysis of N- and O-glycans released from glycoproteins, *Nature Protocols,* 2012, vol. 7, pp. 1299-1310.

[xxix] A. Bohne-Lang and C-W von der Lieth, GlyProt: In-silico glycosylation of proteins, *Nucleic Acid Research,* 2005, vol. 33, pp. W214-219.

[xxx] I. H. Ansari et al., Influence of N-linked glycosylation of porcine reproductive and respiratory syndrome virus GP5 on virus infectivity, antigenicity, and ability to induce neutralizing antibodies. *J. of Virology*, 2006, vol. 80, pp. 3994-4004.

[xxxi] E. H. J. Wissink et al. Significance of the oligosaccharides of the porcine reproductive and respiratory syndrome virus glycoproteins GP2a and GP5 for infectious virus production. *J. of Gen. Virology,* 2004, vol. 85, pp. 3715-3723.

[xxxii] http://en.wikipedia.org/wiki/Glyceraldehyde_3-phosphate_dehydrogenase

[xxxiii] J. Jamieson, Synthesis of Glycosylated Heterodimer Peptide, Almac Group, Project No. 1844A0003Dv1, April 19th 2012.

[xxxiv] D. Simaeys et al., *Study of the Molecular Recognition of Aptamers Selected through* Ovarian Cancer Cell-SELEX. *PloS-ONE,* 2010, vol. 5 (11), p. e13770.

[xxxv] E. Roulet et al., High-throughput SELEX-SAGE method for quantitative modeling of transcription-factor. *Nature Biotechnology,* 2002, vol. 20, pp. 831-835. Also A. B. Iliuk et al., Aptamer in Bioanalytical Applications. *Anal. Chem.,* 2011, vol. 83, pp. 4440-4452. Also X. Yang et al., Strategies for the discovery of therapeutics aptamers. *Expert Opin. Drug Discov.,* 2011, vol 6, pp. 75-87.

[xxxvi] R. Levi et al. Microculture virus titration—a simple colorimetric assay for PRRS virus titration. J. of Virological Methods, 1995, vol. 52, pp. 55-64.

[xxxvii] A. D. Keefe & S. T. Cload, SELEX with modified nucleotides. *Curr. Opinion in Chem. Biol.,* 2008, vol. 12, pp. 448-456. Also J. Wang & G. Li. Aptamers against cell surface receptors: Selection, modifications and application. *Curr. Medi. Chem.,* 2011, vol. 18, pp. 4107-4116. Also R. E. Wang et al., Improving the stability of aptamers by chemical modifications. *Curr. Medi. Chem.,* 2011, vol. 18, pp. 4126-4138.

[xxxviii] *The Concise Encyclopedia of Polymer Science And Engineering*, pp. 858-859, J. I. Kroschwitz, ed. By John Wiley & Sons, 1990. Also U. Englisch & D. H. Gausset, Chemically Modified Oligonucleotides as Probes and Inhibitors. *Angewandte Chemie* Int. Edition, 1991, vol. 30, pp. 613-722. Also Y. S. Sanghvi, Chapter 15, *Antisense Research and Applications*, pp. 273-288, ed. by S. T. Crooke and B. Lebleu, published by CRC Press, Boca Raton, 1993.

[xxxix] Y. S. Sanghvi, Chapter 15, *Antisense Research and Applications*, see pp. 276-278. Ed. by S. T. Crooke and B. Lebleu, published by CRC Press, Boca Raton, 1993.

[xl] See U.S. Pat. No. 6,303,374 (Antisense modulation of caspase 3 expression).

[xli] J. H. Lin et al., Protective effects of oral microencapsulated *Mycoplasma* Hyopneumoniae vaccine prepared by co-spray drying method. *J. Vet. Med. Sci.,* 2003, vol. 65, pp. 69-74.

[xlii] F. Szoka & D. Papahadjopoulos. Comparative properties and methods of preparation of lipid vesicles (liposomes). *Annual review of biophysics and bioengineering,* 1980, vol. 9, pp. 467-508. Also A. Gomezhens & J. Fernandezromero. Analytical methods for the control of liposomal delivery systems. *TrAC Trends in Analytical Chemistry,* 2006, vol. 25, pp. 167-178. Also M. R.Mozafari. Liposomes: an overview of manufacturing techniques. *Cell Mol Biol Lett.,* 2005, vol. 10, pp. 711-719.

[xliii] A. Jesorka & O. Orwar, Liposomes: Technologies and Analytical Applications. in *Annual Rev. Anal. Chem.,* 2008, vol. 1, pp. 801-832. Also B. Maherani et al. Liposomes: A Review of Manufacturing Techniques and Targeting Strategies, in *Current Nanoscience,* 2011, vol. 7, pp. 436-452.

[xliv] see *Remington's Pharmaceutical Sciences*, Mack Publishing Co., Easton, Pa., latest edition. Also Advanced Drug Delivery: Perspectives and prospects. In *Advanced Drug Delivery Reviews,* 2013, vol. 65, no 1, pp. 1-148. Also see Drug delivery (http://en.wikipedia.org/wiki/Drug_delivery). Also see *Drug Delivery Journal*. Copyright by Informa Healthcare USA, Inc. ISSN 1071-7544 print/ISSN 1521-0464 online. Also J. S. Patil & S. Sarasija. Pulmonary drug delivery strategies: A concise, systematic review. *Lung India,* 2012, vol. 29, pp. 44-49.

[xlv] W. Rojanarat et al. Inhaled pyrazinamide proliposome for targeting alveolar macrophages. *Drug Delivery,* 2012, vol. 19, pp. 334-345.

[xlvi] *PCR Protocols: A Guide to Methods and Applications*. Editors M. A. Innis, D. H. Gelfand, J. J. Sninsky, & T. J. White. Academic Press, 1990.

[xlvii] see *Rational Drug Design: Novel Methodology and Practical Application*, Editors A. L. Parrill & M. R. Reddy, Oxford University Press, 1999. Also *Advances In Antiviral Drug Design*, Editor De Clerq. Elsevier Science & Tech, 2007. Also *Textbook of Drug Design and Discovery*. Editors U. Madsen, P. Krogsgaard-Larsen & T. Liljefors. Taylor & Francis, 2002. ISBN 0-415-28288.

[xlviii] V. Lounnas et al. Current progress in Structure-Based Rational Drug Design marks a new mindset in drug discovery, *Compu. & Struc. Biotech. J.,* 2013, vol. 5, e201302011. Also

[xlix] http://en.wikipedia.org/wiki/Rational-drug-design

[l] X. Yang et al., Strategies for the discovery of therapeutics aptamers. *Expert Opin. Drug. Discov.,* 2011, vol. 6, pp. 75-87. Also Aptamers specific for biomolecules and methods of making (U.S. Pat. No. 5,756,291). Also *Affinity Chromatography*, Editor H. Schott, Marcel Dekker, Inc., New York, 1984.

[li] J. Vagner et al., Peptidomimetics, a synthetic tool of drug discovery. *Curr. Opinion in Chem. Biol.,* 2008, vol. 12, pp. 292-296. Also M. R. Arkin & J. A. Wells, Small-molecule inhibitors of protein-protein interactions: Progressing towards the dream, in *Nature Review* (*Drug Discovery*), 2004, vol. 3, pp. 301-317.

[lii] *Current Protocols in Molecular Biology*, ed. by F. M. Ausubel et al., John Wiley & Sons, 1999-2014 (DOI: 10.1002/0471142727).

[liii] R. Kapetanovic & L. Fairbairn, Macrophages Isolation in Pig (Monocyte, Peritoneal, Alveolar and Bone-Marrow), Testing protocol, *The Roslin Institute*, August 2009. Also Y. J. Lee et al., Generation of a porcine alveolar macrophage cell line for the growth of porcine reproductive and respiratory syndrome virus. *J. of Virol. Methods,* 2009, vol. 163, pp. 410-415.

[liv] Y. Du et al. Antiviral activity of Tilmicosin for Type I and Type II Porcine Reproductive and Respiratory Syndrome virus in cultured porcine alvelolar macrophages. *J. of Antivirals & Antiretrovirals,* 2011, vol. 3, pp. 28-33. Also M. Misener et al. Preliminary evaluation of clinical effects and cost-effectiveness of in-feed Pulmotil® and serum inoculation in an outbreak of PRRS, in the *Proc. of the* 19*th* *IPVS Congress*, Copenhagen, 2006, vol. 2, p. 13. Also J. Eriksen et al., Field evaluation of Pulmotil® in the presence of PRRS virus and mixed respiratory infections, in the *Proc. of the* 16*th* *IPVS Congress*, Melbourne, 2000, vol. 1, p. 525.

The invention claimed is:

1. A nucleic acid molecule comprising a polynucleotide sequence capable of specifically binding a polypeptidic complex participating in the PRRS virus (PRRSV) infection of cells wherein the polynucleotide sequence is selected from the group consisting of A505 (SEQ ID NO: 9), A507 (SEQ ID NO: 11), and A508 (SEQ ID NO: 12) for type 2 PRRSV, and from the group consisting of PEU-499 (SEQ ID NO: 15), PEU-842 (SEQ ID NO: 16), PEU-852 (SEQ ID NO: 17), PEU-424 (SEQ ID NO: 18), and PEU-962 (SEQ ID NO: 19) for type 1 PRRSV.

2. The nucleic acid molecule according to claim 1, wherein the nucleic acid molecule further comprises a detectable label.

3. The nucleic acid molecule according to claim 2, wherein the polynucleotide sequence includes FDG ([$^{18}$F]-2-fluoro-2-deoxy-D-glucose) and/or PEG modified nucleotides.

4. The nucleic acid molecule according to claim 1, wherein the polynucleotide sequence is selected having a length between 10 to 15 nucleotides.

5. A pharmaceutical composition comprising a nucleic acid molecule according to claim 1 and a physiologically acceptable carrier, preferably wherein the nucleic acid molecule is conjugated to an antiviral agent and optionally further including an active pharmaceutical agent.

6. The pharmaceutical composition according to claim 5, wherein the composition includes an active agent selected from the group consisting of an immunomodulatory agent, an antiviral agent, an antisense molecule, and a ribozyme.

7. An article-of-manufacture comprising packaging material and a pharmaceutical composition according to claim 5 being contained within the packaging material.

8. A method of identifying PRRS virus (PRRSV) in a biological sample, the method comprising: (a) contacting the biological sample with a nucleic acid molecule according to claim 1 to form an immune complex; and (b) detecting the nucleic acid molecule bound to the PRRSV polypeptide in the biological sample, to thereby identify the PRRSV infection.

9. The method according to claim 8, wherein the nucleic acid molecule comprises a detectable label and the immune complex comprising the PRRSV is determined by quantifying the intensity of the label following (b).

10. A vaccine for vaccination of pigs, the vaccine comprising the nucleic acid molecule according to claim 1.

11. A method of treating or preventing PRRS virus (PRRSV) infection comprising providing to a subject in need thereof, a therapeutically effective amount of a nucleic acid molecule according to claim 1.

12. A method of targeting an antiviral agent to a PRRS virus infected tissue, the method comprising administering to a subject in need thereof a therapeutic effective amount of the antiviral agent conjugated to a nucleic acid molecule according to claim 1.

* * * * *